United States Patent
Raab et al.

(10) Patent No.: US 11,066,657 B2
(45) Date of Patent: Jul. 20, 2021

(54) METHODS AND COMPOSITIONS FOR STABILIZING TRANS-SPLICING INTEIN MODIFIED PROTEASES

(71) Applicant: AGRIVIDA, INC., Woburn, MA (US)

(72) Inventors: R. Michael Raab, Arlington, MA (US); Binzhang Shen, Boston, MA (US); Gabor Lazar, Belmont, MA (US)

(73) Assignee: AGRIVIDA, INC, Woburn, MA (US)

(*) Notice: Subject to any disclaimer, the term of this patent is extended or adjusted under 35 U.S.C. 154(b) by 0 days.

(21) Appl. No.: 16/899,064

(22) Filed: Jun. 11, 2020

(65) Prior Publication Data

US 2020/0308564 A1 Oct. 1, 2020

Related U.S. Application Data

(63) Continuation of application No. 15/519,602, filed as application No. PCT/US2015/057862 on Oct. 28, 2015, now Pat. No. 10,731,143.

(60) Provisional application No. 62/069,653, filed on Oct. 28, 2014.

(51) Int. Cl.
  *C12N 9/54* (2006.01)
  *C11D 3/386* (2006.01)
  *C07K 14/00* (2006.01)

(52) U.S. Cl.
  CPC .............. *C12N 9/54* (2013.01); *C07K 14/00* (2013.01); *C11D 3/386* (2013.01); *C11D 3/38663* (2013.01); *C07K 2319/00* (2013.01); *C07K 2319/92* (2013.01)

(58) Field of Classification Search
  CPC ................................ C12N 9/54; C11D 3/386
  See application file for complete search history.

(56) References Cited

U.S. PATENT DOCUMENTS

| | | | |
|---|---|---|---|
| 3,332,880 A | 7/1967 | Kessler | |
| 3,664,961 A | 5/1972 | Norris | |
| 3,717,630 A | 2/1973 | Booth | |
| 3,941,710 A | 3/1976 | Gilbert | |
| 4,115,292 A | 9/1978 | Richardson | |
| 5,731,278 A | 3/1998 | Nair | |
| 7,648,953 B2 | 1/2010 | Bastigkeit | |
| 8,530,218 B2 | 9/2013 | Ferrari | |
| 8,808,704 B2 | 8/2014 | Hollingshead | |
| 2002/0182221 A1 | 12/2002 | Bruck | |
| 2007/0066525 A1 | 3/2007 | Lee | |
| 2011/0244518 A1 | 10/2011 | Zheng | |
| 2013/0007919 A1 | 1/2013 | Shen | |
| 2013/0036517 A1 | 2/2013 | Apgar | |
| 2013/0071884 A1 | 3/2013 | Raab | |
| 2014/0106399 A1 | 4/2014 | Lin | |

FOREIGN PATENT DOCUMENTS

| | | |
|---|---|---|
| CN | 103242973 A | 8/2013 |
| EP | 0929642 A | 7/1999 |
| EP | 2126017 A | 12/2009 |
| EP | 2551335 A1 | 1/2013 |
| EP | 2712913 A | 4/2014 |
| EP | 2855408 A1 | 4/2015 |
| WO | 9516044 A2 | 6/1995 |
| WO | 1998013461 A1 | 4/1998 |
| WO | 1999049009 A1 | 9/1999 |
| WO | 2013/045632 A1 | 4/2013 |
| WO | 2013160023 A1 | 10/2013 |
| WO | 2014019903 A1 | 2/2014 |
| WO | 2014/055782 A1 | 4/2014 |
| WO | 2014055782 A1 | 4/2014 |
| WO | 2014190131 A1 | 11/2014 |

OTHER PUBLICATIONS

Aranko AS., Oeemig JS., Iwai H. (2013) Structural basis for protein trans-splicing by a bacterial intein-like domain protein ligation without nucleophilic side chains. FEBS J., 280(14):3256-69.
Besteman K., Zevenbergen M., Heering H. and Lemay S. (2004) Direct Observation of Charge Inversion by Multivalent Ions as a Universal Electrostatic Phenomenon. Phys. Rev. Lett. 93, 170802.
Bonifait et al. (2010) Cell surface characteristics of nontypeable isolates of *Streptococcus suis*, FEMS Microbiol. Lett. 311: 160-166.
Davis et al. (1991) Novel Structure of the recA Locus of *Mycobacterium tuberculosis* Implies Processing of the Gene Product, J Bacteriology, 173(18):5653-5662.
Evans TC., Martin D., Kolly R., Panne D., Sun L, Ghosh I., Chen L., Liu X-Q. and Xu M-Q. (2000) Protein trans-Splicing and Cyclization by a Naturally Split Intein from the dnaE Gene of*Synechocystis* Species PCC6803. J. Biol. Chem. 275, 9091-9094.
Lyklema J. (2009) Quest for ion-ion correlations in electric double layers and overcharging phenomena. Adv. Colloid Interface Sci. 147, 205-213.
Martin-Molina A., Quesada-Pérez M., Galisteo-González F. (2003) Looking into overcharging in model colloids through electrophoresis: asymmetric electrolytes. J. Chem. Phys. 118, 4183-89.
Martin DD., Xu M-Q. and Evans TC. (2001) Characterization of a Naturally Occurring Trans-Splicing Intein from *Synechocystis* sp. PCC6803. Biochemistry, 40, 1393-1402.
Mootz HD., Blum ES., Tyszkiewicz AB. and Muir TW. (2003) Conditional protein splicing: a new tool to control protein structure and function in vitro and in vivo. J.Am.Chem.Soc. 125, 10561-9.
Nichols NM, Benner JS, Martin DD and Evans TC Jr (2003) Zinc ion effects on individulal Ssp DnaE splicing steps: regulating pathway progression. Biochemistry, 42 (18), 5301-11.
Perler FB. (2005) Protein Splicing Mechanisms and Applications. IUBMB Life, 57(7), 469-476.
Selgrade DF., Lohmueller JJ., Lienert F. and Silver P. (2013) Protein scaffold-activated protein trans-splicing in mammalian cells. J.Am. Chem.Soc. 135, 7713-19.
Shah NH., Eryilmaz E., Cowburn D. and Muir TW. (2013) Naturally split inteins assemble through a "capture and collapse" mechanism. J.Am.Chem.Soc. 135, 18673-81.

(Continued)

*Primary Examiner* — Sheridan Swope
(74) *Attorney, Agent, or Firm* — Volpe Koenig

(57) ABSTRACT

Methods for producing a trans-splicing intein-modified protease with enhanced solubility and regulating its activity are described. Intein-modified proteases having enhanced solubility and polynucleotides encoding the same are provided. Methods of storing trans-splicing proteases are also described.

15 Claims, 26 Drawing Sheets

Specification includes a Sequence Listing.

(56) References Cited

OTHER PUBLICATIONS

Shi J. and Muir TWJ. (2005) Development of a tandem protein trans-splicing system based on native and engineered split inteins. J. Am.Chem. Soc. 127, 6198-206.

Smith TF, Waterman MS 1981 "Identification of Common Molecular Subsequences," J Mol Biol 147: 195.

Sun P., Ye S., Ferrandon S., Evans T.C., Xu M-Q., and Rao Z. (2005) Crystal Structures of an Intein from the Split dnaE Gene of *Synechocystis* sp. PCC6803 Reveal the Catalytic Model Without the Penultimate Histidine and the Mechanism of Zinc Ion Inhibition of Protein Splicing. J. Mol. Biol. 353, 1093-1105.

Topilina NI. and Mills KV. (2014) Recent advances in in vivo applications of intein-mediated protein splicing. Mobile DNA, (5) 5.

Trulsson M., Jonsson B., Akesson T. and Forsman J. (2006) Repulsion between Oppositely Charged Surfaces in Multivalent Electrolytes. Phys. Rev. Lett. 97, 068302.

Wu H., Hu Z, and Liu X-Q. (1998) Protein trans-splicing by a split intein encoded in a split DnaE gene of*Synechocystis* sp. PCC6803. Proc.Natl.Acad.Sci USA, 95, 9226-31.

Zhang L., Xiao N.n Pan Y., Zheng Y., Pan Z., Luo Z., Xu X., Liu Y. (2010) Binding and inhibition of copper ions to RecA inteins from *Mycobacterium tuberculosis*. Chemistry, 16(14), 4297-306.

Zhang L, Zheng Y., Callahan B, Bedfort M., Liu Y. (2011) Cisplatin inhibits protein splicing, suggesting inteins as therapeutic targets in mycobacteria. J.Biol.Chem. 286(2), 1277-82.

Zheng Y., Wu Q., Xu M-Q. and Liu Y. (2012) Mutual synergistic protein folding in split intein. Biosci. Rep. 32, 433-442.

International Search Report issued in corresponding International Patent Application No. PCT/US2015/057862 dated Mar. 4, 2016, consisting of 6 pp.

Written Opinion issued in corresponding International Patent Application No. PCT/US2015/057862 dated Mar. 4, 2016, consisting 10 pp.

Wang, et al. Ubiquitin-intein and SUMO2-intein fusion systems for enhanced protein production and purification. Protein Expr Purification. Mar. 2012, vol. 82, No. 1, pp. 174-178.

Sonntag et al. An intein-cassette integration approach used for the generation of a split TEV protease activiated by conditional protein splicing. Mol. BioSyst. 2011, 7, 2031-2039.

Wang et al. Ubiquitin-intein and SUMO2-intein fusion systems for enhanced protein production and purification. Protein Expression and Purification 82 (2012) 174-178.

USPTO in-house alignment of SEQ ID No. 1 with each of SEQ ID No. 2, 6, 14, 15, 51 and 53. Performed Dec. 3, 2018.

USPTO in-house alignment of SEQ ID No. 2 with each of SEQ ID No. 1, 6, 14, 15, 51 and 53. Performed Dec. 3, 2018.

Crasto et al. Linker: a program to generate linker sequences for fusion proteins. Protein Engineering [May 1, 2000, 13(5):309-312].

Du et al. Backbone Dynamics and Global Effects of an Activating Mutation in Minimized Mtu RecA Inteins. J. Mol. Biol. (2010) 400, 755-767.

Shah. Ultrafast Protein Splicing is Common Among Cyanobacterial Split Inteins: Implications for Protein Engineering. J Am Chem Soc. Jul. 18, 2012; 134(28):11338-41.

Xie et al., 2013, Effects of Thioredoxin: SUMO and Intein on Soluble Fusion Expression of an Antimicrobial Peptide OG2 in *Escherichia coli*,Protein & Peptide Letters, 20, 54-60.

Examination Report dated Apr. 20, 2018 for European Application No. 1585457.3.

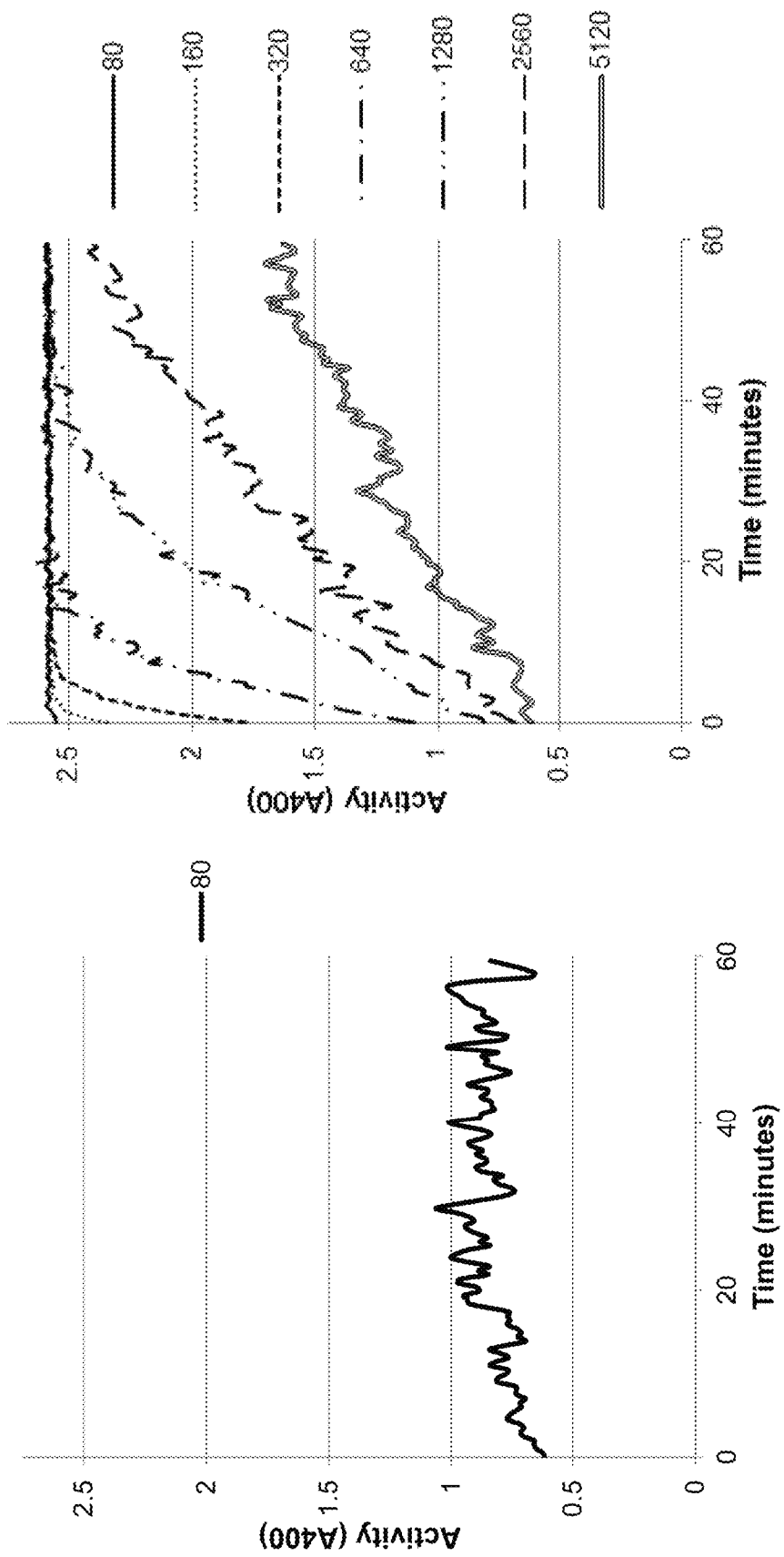

SEQUENCE LISTING

```
<160> NUMBER OF SEQ ID NOS: 59

<210> SEQ ID NO 1
<211> LENGTH: 491
<212> TYPE: PRT
<213> ORGANISM: Artificial Sequence
<220> FEATURE:
<223> OTHER INFORMATION: Synthetic construct, NI-DPNG-TRX

<400> SEQUENCE: 1

Met Ala Glu Glu Ala Lys Glu Lys Tyr Leu Ile Gly Phe Asn Glu Gln
1               5                   10                  15

Glu Ala Val Ser Glu Phe Val Glu Gln Val Glu Ala Asn Asp Glu Val
            20                  25                  30

Ala Ile Leu Ser Glu Glu Glu Val Glu Ile Glu Leu Leu His Glu
        35                  40                  45

Phe Glu Thr Ile Pro Val Leu Ser Val Glu Leu Ser Pro Glu Asp Val
    50                  55                  60

Asp Ala Leu Glu Leu Asp Pro Ala Ile Ser Tyr Ile Glu Glu Asp Ala
65                  70                  75                  80

Glu Val Thr Thr Met Ala Gln Ser Val Pro Trp Gly Ile Ser Arg Val
                85                  90                  95

Gln Ala Pro Ala Ala His Asn Arg Gly Leu Thr Gly Ser Gly Val Lys
            100                 105                 110

Val Ala Val Leu Asp Thr Gly Ile Ser Thr His Pro Asp Leu Asn Ile
        115                 120                 125

Arg Gly Gly Ala Ser Phe Val Pro Gly Glu Pro Ser Thr Gln Asp Gly
    130                 135                 140

Asn Gly His Gly Thr His Val Ala Gly Thr Ile Ala Ala Leu Asn Asn
145                 150                 155                 160

Ser Ile Gly Val Leu Gly Val Ala Pro Ser Ala Glu Leu Tyr Ala Val
                165                 170                 175

Lys Val Leu Gly Ala Ser Gly Ser Gly Ser Val Ser Ser Ile Ala Gln
            180                 185                 190

Gly Leu Glu Trp Ala Gly Asn Asn Gly Met His Val Ala Asn Leu Ser
        195                 200                 205

Leu Gly Ser Pro Ser Pro Ser Ala Thr Leu Glu Gln Ala Val Asn Ser
    210                 215                 220

Ala Thr Ser Arg Gly Val Leu Val Val Ala Ala Ser Gly Asn Ser Gly
225                 230                 235                 240

Ala Gly Ser Ile Ser Tyr Pro Ala Arg Tyr Ala Asn Ala Met Ala Val
                245                 250                 255

Gly Ala Thr Asp Gln Asn Asn Asn Arg Ala Ser Phe Ser Gln Tyr Gly
```

```
            260                 265                 270

Ala Gly Leu Asp Ile Val Ala Pro Gly Val Asn Val Gln Ser Thr Tyr
        275                 280                 285

Pro Gly Cys Leu Asp Leu Lys Thr Gln Val Gln Thr Pro Gln Gly Met
    290                 295                 300

Lys Glu Ile Ser Asn Ile Gln Val Gly Asp Leu Val Leu Ser Asn Thr
305                 310                 315                 320

Gly Tyr Asn Glu Val Leu Asn Val Phe Pro Lys Ser Lys Lys Lys Ser
                325                 330                 335

Tyr Lys Ile Thr Leu Glu Asp Gly Lys Glu Ile Ile Cys Ser Glu Glu
            340                 345                 350

His Leu Phe Pro Thr Gln Thr Gly Glu Met Asn Ile Ser Gly Gly Leu
        355                 360                 365

Lys Glu Gly Met Cys Leu Tyr Val Lys Glu Asp Pro Asn Gly Met Ser
    370                 375                 380

Asp Lys Ile Ile His Leu Thr Asp Asp Ser Phe Asp Thr Asp Val Leu
385                 390                 395                 400

Lys Ala Asp Gly Ala Ile Leu Val Asp Phe Trp Ala Glu Trp Cys Gly
                405                 410                 415

Pro Cys Lys Met Ile Ala Pro Ile Leu Asp Glu Ile Ala Asp Glu Tyr
            420                 425                 430

Gln Gly Lys Leu Thr Val Ala Lys Leu Asn Ile Asp Gln Asn Pro Gly
        435                 440                 445

Thr Ala Pro Lys Tyr Gly Ile Arg Gly Ile Pro Thr Leu Leu Leu Phe
    450                 455                 460

Lys Asn Gly Glu Val Ala Ala Thr Lys Val Gly Ala Leu Ser Lys Gly
465                 470                 475                 480

Gln Leu Lys Glu Phe Leu Asp Ala Asn Leu Ala
                485                 490

<210> SEQ ID NO 2
<211> LENGTH: 213
<212> TYPE: PRT
<213> ORGANISM: Artificial Sequence
<220> FEATURE:
<223> OTHER INFORMATION: Synthetic construct, Trx-DPNG-MTT-IC

<400> SEQUENCE: 2

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Asp Pro Asn
            100                 105                 110

Gly Met Thr Lys Lys Ile Thr Lys Ile Glu Glu Leu Asp Glu Arg Glu
        115                 120                 125

Leu Ile Asp Ile Glu Val Ser Gly Asn His Leu Phe Tyr Ala Asn Asp
```

```
                130               135               140
Ile Gly Thr His Asn Ser Thr Tyr Ala Ser Leu Asn Gly Thr Ser Met
145                 150                 155                 160

Ala Thr Pro His Val Ala Gly Ala Ala Ala Leu Val Lys Gln Lys Asn
                165                 170                 175

Pro Ser Trp Ser Asn Val Gln Ile Arg Asn His Leu Lys Asn Thr Ala
            180                 185                 190

Thr Ser Leu Gly Ser Thr Asn Leu Tyr Gly Ser Gly Leu Val Asn Ala
        195                 200                 205

Glu Ala Ala Thr Arg
    210

<210> SEQ ID NO 3
<211> LENGTH: 1476
<212> TYPE: DNA
<213> ORGANISM: Artificial Sequence
<220> FEATURE:
<223> OTHER INFORMATION: Synthetic construct, NI-DPNG-Trx coding
      sequence

<400> SEQUENCE: 3
```

| | | | | | |
|---|---|---|---|---|---|
| atggctgaag | aagcaaaaga | aaaatattta | attggcttta | atgagcagga | agctgtcagt | 60 |
| gagtttgtag | aacaagtaga | ggcaaatgac | gaggtcgcca | ttctctctga | ggaagaggaa | 120 |
| gtcgaaattg | aattgcttca | tgaatttgaa | acgattcctg | ttttatccgt | tgagttaagc | 180 |
| ccagaagatg | tggacgcgct | tgaactcgat | ccagcgattt | cttatattga | gaggatgca | 240 |
| gaagtaacga | caatggcgca | atcggtacct | tggggaatta | gccgtgtgca | agccccagct | 300 |
| gcccataacc | gtggattgac | aggttctggt | gtaaaagttg | ctgtcctcga | tacagggata | 360 |
| tccactcatc | cagatctaaa | tattcgtggt | ggcgcaagct | ttgtaccagg | gaaccgtcg | 420 |
| actcaagatg | ggaatgggca | tggcacgcat | gtggccggga | cgatcgctgc | tttaaacaat | 480 |
| tcgattggcg | ttcttggcgt | agcgccgagc | gctgagctat | acgctgttaa | agtcctaggg | 540 |
| gcgagcggtt | caggttcggt | cagctcgatt | gcccaaggat | tggaatgggc | agggaacaat | 600 |
| ggcatgcacg | ttgctaattt | gagtttagga | agcccttcgc | caagtgccac | acttgagcaa | 660 |
| gctgttaata | gcgcgacttc | tagaggcgtt | cttgttgtag | cggcatctgg | gaactcaggt | 720 |
| gcaggctcaa | tcagctatcc | ggcgcgctat | gcgaacgcaa | tggcagtcgg | agctactgat | 780 |
| caaaacaaca | accgcgctag | cttttcacag | tatggcgcag | gccttgacat | tgtcgcaccc | 840 |
| ggggtaaacg | tgcagagcac | atacccaggt | tgtctggacc | tgaaaacgca | agtgcaaacc | 900 |
| ccgcaaggca | tgaaggaaat | ctcaaacatc | aagtcggtg | acctggtgct | gtcgaatacc | 960 |
| ggctataaca | agtgctgaa | tgtttttccg | aagagcaaaa | agaaatctta | caagatcacg | 1020 |
| ctggaagatg | gcaaggaaat | tatttgcagc | gaagaacatc | tgttcccgac | ccagacgggc | 1080 |
| gaaatgaata | tctccggcgg | tctgaaagaa | ggcatgtgtc | tgtacgtcaa | ggaagatcct | 1140 |
| aatggtatga | gcgataaaat | tattcacctg | actgacgaca | gttttgacac | ggatgtactc | 1200 |
| aaagcggacg | gggcgatcct | cgtcgatttc | tgggcagagt | ggtgcggtcc | gtgcaaaatg | 1260 |
| atcgccccga | ttctggatga | aatcgctgac | gaatatcagg | caaactgac | cgttgcaaaa | 1320 |
| ctgaacatcg | atcaaaaccc | tggcactgcg | ccgaaatatg | gcatccgtgg | tatcccgact | 1380 |
| ctgctgctgt | tcaaaaacgg | tgaagtggcg | gcaaccaaag | tgggtgcact | gtctaaaggt | 1440 |
| cagttgaaag | agttcctcga | cgctaacctg | gcctag | | | 1476 |

<210> SEQ ID NO 4
<211> LENGTH: 642
<212> TYPE: DNA
<213> ORGANISM: Artificial Sequence
<220> FEATURE:
<223> OTHER INFORMATION: Synthetic construct, Trx-DPNG-MTT-IC coding sequence

<400> SEQUENCE: 4

```
atgagcgata aaattattca cctgactgac gacagttttg acacggatgt actcaaagcg      60
gacgggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggccgat cctaatggta tgacgaagaa aattacgaag     360
atcgaagaac tggatgaacg tgaactgatt gacatcgaag ttagcggcaa ccatctgttt     420
tacgcgaatg acattgggac ccacaactca acttatgcca gcttaaacgg tacatcgatg     480
gctactcctc atgttgcagg tgcggccgcc cttgttaaac aaaagaaccc atcttggtct     540
aatgtacaaa ttcgaaatca tctaaagaat acggcaacta gtttaggaag cacgaacttg     600
tatggaagcg gacttgttaa cgcagaagcg gcaacgcgtt aa                       642
```

<210> SEQ ID NO 5
<211> LENGTH: 4
<212> TYPE: PRT
<213> ORGANISM: Artificial Sequence
<220> FEATURE:
<223> OTHER INFORMATION: Synthetic construct, DPNG linker

<400> SEQUENCE: 5

Asp Pro Asn Gly
1

<210> SEQ ID NO 6
<211> LENGTH: 380
<212> TYPE: PRT
<213> ORGANISM: Bacillus lentus
<220> FEATURE:
<221> NAME/KEY: MISC_FEATURE
<222> LOCATION: (1)..(380)
<223> OTHER INFORMATION: Savinase P29600

<400> SEQUENCE: 6

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Ala Glu Glu Ala Lys
            20                  25                  30

Glu Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His

```
                115                 120                 125
Asn Arg Gly Leu Thr Gly Ser Gly Val Lys Val Ala Val Leu Asp Thr
    130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Ser Ala Glu Leu Tyr Ala Val Lys Val Leu Gly Ala Ser
        195                 200                 205

Gly Ser Gly Ser Val Ser Ser Ile Ala Gln Gly Leu Glu Trp Ala Gly
    210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Gly Ser Ile Ser Tyr
            260                 265                 270

Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
                325                 330                 335

Ala Leu Val Lys Gln Lys Asn Pro Ser Trp Ser Asn Val Gln Ile Arg
            340                 345                 350

Asn His Leu Lys Asn Thr Ala Thr Ser Leu Gly Ser Thr Asn Leu Tyr
        355                 360                 365

Gly Ser Gly Leu Val Asn Ala Glu Ala Ala Thr Arg
    370                 375                 380

<210> SEQ ID NO 7
<211> LENGTH: 1143
<212> TYPE: DNA
<213> ORGANISM: Bacillus lentus
<220> FEATURE:
<221> NAME/KEY: misc_feature
<222> LOCATION: (1)..(1143)
<223> OTHER INFORMATION: P29600 coding sequence

<400> SEQUENCE: 7
atgaagaaac cgttggggaa aattgtcgca agcaccgcac tactcatttc tgttgctttt    60
agttcatcga tcgcatcggc tgctgaagaa gcaaaagaaa atatttaat tggctttaat   120 gagcaggaag ctgtcagtga gttttgtaaa caagtagagg caaatgacga ggtcgccatt   180
ctctctgagg aagaggaagt cgaaattgaa ttgcttcatg aatttgaaac gattcctgtt   240
ttatccgttg agttaagccc agaagatgtg acgcgcttg aactcgatcc agcgatttct   300
tatattgaag aggatgcaga agtaacgaca atggcgcaat cggtaccatg gggaattagc   360
cgtgtgcaag ccccagctgc ccataaccgt ggattgacag ttctggtgt aaaagttgct   420 gtcctcgata cagggatatc cactcatcca gatctaaata ttcgtggtgg cgcaagcttt   480
gtaccagggg aaccgtcgac tcaagatggg aatgggcatg gcacgcatgt ggccgggacg   540
```

-continued

| | | | | | |
|---|---|---|---|---|---|
| atcgctgctt | taaacaattc | gattggcgtt | cttggcgtag | cgccgagcgc | tgagctatac | 600 |
| gctgttaaag | tcctaggggc | gagcggttca | ggttcggtca | gctcgattgc | ccaaggattg | 660 |
| gaatgggcag | ggaacaatgg | catgcacgtt | gctaatttga | gtttaggaag | cccttcgcca | 720 |
| agtgccacac | ttgagcaagc | tgttaatagc | gcgacttcta | gaggcgttct | tgttgtagcg | 780 |
| gcatctggga | actcaggtgc | aggctcaatc | agctatccgg | cgcgctatgc | gaacgcaatg | 840 |
| gcagtcggag | ctactgatca | aaacaacaac | cgcgctagct | tttcacagta | tggcgcaggc | 900 |
| cttgacattg | tcgcacccgg | ggtaaacgtg | cagagcacat | acccaggttc | aacatatgcc | 960 |
| agcttaaacg | gtacatcgat | ggctactcct | catgttgcag | gtgcggccgc | ccttgttaaa | 1020 |
| caaaagaacc | catcttggtc | taatgtacaa | attcgaaatc | atctaaagaa | tacggcaact | 1080 |
| agtttaggaa | gcacgaactt | gtatggaagc | ggacttgtta | acgcagaagc | ggcaacgcgt | 1140 |
| taa | | | | | | 1143 |

<210> SEQ ID NO 8
<211> LENGTH: 379
<212> TYPE: PRT
<213> ORGANISM: Bacillus licheniformis
<220> FEATURE:
<221> NAME/KEY: MISC_FEATURE
<222> LOCATION: (1)..(379)
<223> OTHER INFORMATION: Alkaline protease Q6PNN5

<400> SEQUENCE: 8

```
Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
    210                 215                 220

Val Ile Asn Met Ser Leu Gly Gly Ala Ser Gly Ser Thr Ala Met Lys
225                 230                 235                 240
```

```
Gln Ala Val Asp Asn Ala Tyr Ala Arg Gly Val Val Val Ala Ala
            245                 250                 255

Ala Gly Asn Ser Gly Ser Ser Gly Asn Thr Asn Thr Ile Gly Tyr Pro
        260                 265                 270

Ala Lys Tyr Asp Ser Val Ile Ala Val Gly Ala Val Asp Ser Asn Ser
    275                 280                 285

Asn Arg Ala Ser Phe Ser Ser Val Gly Ala Glu Leu Glu Val Met Ala
290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Ala Gln
    370                 375

<210> SEQ ID NO 9
<211> LENGTH: 404
<212> TYPE: PRT
<213> ORGANISM: Aspergillus flavus
<220> FEATURE:
<221> NAME/KEY: MISC_FEATURE
<222> LOCATION: (1)..(404)
<223> OTHER INFORMATION: B8NLY9 _PEPA_ASPFN

<400> SEQUENCE: 9

Met Val Ile Leu Ser Lys Val Ala Ala Val Ala Val Gly Leu Ser Thr
1               5                   10                  15

Val Ala Ser Ala Leu Pro Thr Gly Pro Ser His Ser Pro His Ala Arg
            20                  25                  30

Arg Gly Phe Thr Ile Asn Gln Ile Thr Arg Gln Thr Ala Arg Val Gly
        35                  40                  45

Pro Lys Thr Ala Ser Phe Pro Ala Ile Tyr Ser Arg Ala Leu Ala Lys
    50                  55                  60

Tyr Gly Gly Thr Val Pro Ala His Leu Lys Ser Ala Val Ala Ser Gly
65                  70                  75                  80

His Gly Thr Val Val Thr Ser Pro Glu Pro Asn Asp Ile Glu Tyr Leu
                85                  90                  95

Thr Pro Val Asn Ile Gly Gly Thr Thr Leu Asn Leu Asp Phe Asp Thr
            100                 105                 110

Gly Ser Ala Asp Leu Trp Val Phe Ser Glu Glu Leu Pro Lys Ser Glu
        115                 120                 125

Gln Thr Gly His Asp Val Tyr Lys Pro Ser Gly Asn Ala Ser Lys Ile
130                 135                 140

Ala Gly Ala Ser Trp Asp Ile Ser Tyr Gly Asp Gly Ser Ser Ala Ser
145                 150                 155                 160

Gly Asp Val Tyr Gln Asp Thr Val Thr Val Gly Gly Val Thr Ala Gln
                165                 170                 175

Gly Gln Ala Val Glu Ala Ala Ser Lys Ile Ser Asp Gln Phe Val Gln
            180                 185                 190

Asp Lys Asn Asn Asp Gly Leu Leu Gly Leu Ala Phe Ser Ser Ile Asn
        195                 200                 205
```

```
Thr Val Lys Pro Lys Pro Gln Thr Phe Phe Asp Thr Val Lys Asp
    210             215                 220
Gln Leu Asp Ala Pro Leu Phe Ala Val Thr Leu Lys Tyr His Ala Pro
225                 230                 235                 240
Gly Ser Tyr Asp Phe Gly Phe Ile Asp Lys Ser Lys Phe Thr Gly Glu
                245                 250                 255
Leu Ala Tyr Ala Asp Val Asp Asp Ser Gln Gly Phe Trp Gln Phe Thr
            260                 265                 270
Ala Asp Gly Tyr Ser Val Gly Lys Gly Asp Ala Gln Lys Ala Pro Ile
            275                 280                 285
Thr Gly Ile Ala Asp Thr Gly Thr Thr Leu Val Met Leu Asp Asp Glu
    290                 295                 300
Ile Val Asp Ala Tyr Tyr Lys Gln Val Gln Gly Ala Lys Asn Asp Ala
305                 310                 315                 320
Ser Ala Gly Gly Tyr Val Phe Pro Cys Glu Thr Glu Leu Pro Glu Phe
                325                 330                 335
Thr Val Val Ile Gly Ser Tyr Asn Ala Val Ile Pro Gly Lys His Ile
            340                 345                 350
Asn Tyr Ala Pro Leu Gln Glu Gly Ser Ser Thr Cys Val Gly Gly Ile
            355                 360                 365
Gln Ser Asn Ser Gly Leu Gly Leu Ser Ile Leu Gly Asp Val Phe Leu
    370                 375                 380
Lys Ser Gln Tyr Val Val Phe Asp Ser Gln Gly Pro Arg Leu Gly Phe
385                 390                 395                 400
Ala Ala Gln Ala

<210> SEQ ID NO 10
<211> LENGTH: 375
<212> TYPE: DNA
<213> ORGANISM: Artificial Sequence
<220> FEATURE:
<223> OTHER INFORMATION: Synthetic construct, gp41-1 intein coding
      sequence

<400> SEQUENCE: 10
tgtctggacc tgaaaacgca agtgcaaacc ccgcaaggca tgaaggaaat ctcaaacatc    60
caagtcggtg acctggtgct gtcgaatacc ggctataacg aagtgctgaa tgttttccg   120 aagagcaaaa agaaatctta caagatcacg ctggaagatg caaggaaat tatttgcagc   180 gaagaacatc tgttcccgac ccagacgggc gaaatgaata tctccggcgg tctgaaagaa   240
ggcatgtgtc tgtacgtcaa ggaaatgatg ctgaagaaaa ttctgaagat cgaagaactg   300
gatgaacgtg aactgattga catcgaagtt agcggcaacc atctgtttta cgcgaatgac   360
attctgaccc acaac                                                    375

<210> SEQ ID NO 11
<211> LENGTH: 125
<212> TYPE: PRT
<213> ORGANISM: Artificial Sequence
<220> FEATURE:
<223> OTHER INFORMATION: Synthetic construct, gp41-1 intein

<400> SEQUENCE: 11

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30
```

Asn Glu Val Leu Asn Val Phe Pro Lys Ser Lys Lys Ser Tyr Lys
            35                  40                  45

Ile Thr Leu Glu Asp Gly Lys Glu Ile Ile Cys Ser Glu Glu His Leu
 50                  55                  60

Phe Pro Thr Gln Thr Gly Glu Met Asn Ile Ser Gly Gly Leu Lys Glu
 65                  70                  75                  80

Gly Met Cys Leu Tyr Val Lys Glu Met Met Leu Lys Lys Ile Leu Lys
                 85                  90                  95

Ile Glu Glu Leu Asp Glu Arg Glu Leu Ile Asp Ile Glu Val Ser Gly
            100                 105                 110

Asn His Leu Phe Tyr Ala Asn Asp Ile Leu Thr His Asn
            115                 120                 125

<210> SEQ ID NO 12
<211> LENGTH: 264
<212> TYPE: DNA
<213> ORGANISM: Artificial Sequence
<220> FEATURE:
<223> OTHER INFORMATION: Synthetic construct, gp41-1 N-intein coding
      sequence

<400> SEQUENCE: 12
tgtctggacc tgaaaacgca agtgcaaacc ccgcaaggca tgaaggaaat ctcaaacatc      60
caagtcggtg acctggtgct gtcgaatacc ggctataacg aagtgctgaa tgtttttccg     120
aagagcaaaa agaaatctta caagatcacg ctggaagatg gcaaggaaat tatttgcagc     180
gaagaacatc tgttcccgac ccagacgggc gaaatgaata tctccggcgg tctgaaagaa     240
ggcatgtgtc tgtacgtcaa ggaa                                            264

<210> SEQ ID NO 13
<211> LENGTH: 111
<212> TYPE: DNA
<213> ORGANISM: Artificial Sequence
<220> FEATURE:
<223> OTHER INFORMATION: Synthetic construct, gp41-1 C-intein coding
      sequence

<400> SEQUENCE: 13
atgatgctga agaaaattct gaagatcgaa gaactggatg aacgtgaact gattgacatc      60
gaagttagcg gcaaccatct gttttacgcg aatgacattc tgacccacaa c              111

<210> SEQ ID NO 14
<211> LENGTH: 88
<212> TYPE: PRT
<213> ORGANISM: Artificial Sequence
<220> FEATURE:
<223> OTHER INFORMATION: Synthetic construct, gp41-1 N-intein

<400> SEQUENCE: 14

Cys Leu Asp Leu Lys Thr Gln Val Gln Thr Pro Gln Gly Met Lys Glu
  1               5                  10                  15

Ile Ser Asn Ile Gln Val Gly Asp Leu Val Leu Ser Asn Thr Gly Tyr
             20                  25                  30

Asn Glu Val Leu Asn Val Phe Pro Lys Ser Lys Lys Ser Tyr Lys
            35                  40                  45

Ile Thr Leu Glu Asp Gly Lys Glu Ile Ile Cys Ser Glu Glu His Leu
 50                  55                  60

Phe Pro Thr Gln Thr Gly Glu Met Asn Ile Ser Gly Gly Leu Lys Glu
 65                  70                  75                  80

```
Gly Met Cys Leu Tyr Val Lys Glu
                85
```

<210> SEQ ID NO 15
<211> LENGTH: 37
<212> TYPE: PRT
<213> ORGANISM: Artificial Sequence
<220> FEATURE:
<223> OTHER INFORMATION: Synthetic construct, gp41-1 C-intein

<400> SEQUENCE: 15

```
Met Met Leu Lys Lys Ile Leu Lys Ile Glu Glu Leu Asp Glu Arg Glu
1               5                   10                  15

Leu Ile Asp Ile Glu Val Ser Gly Asn His Leu Phe Tyr Ala Asn Asp
            20                  25                  30

Ile Leu Thr His Asn
        35
```

<210> SEQ ID NO 16
<211> LENGTH: 94
<212> TYPE: PRT
<213> ORGANISM: Artificial Sequence
<220> FEATURE:
<223> OTHER INFORMATION: Synthetic construct, Cbu_DnaB (12) N-intein

<400> SEQUENCE: 16

```
Cys Val Thr Gly Asp Thr Leu Ile Cys Leu Ala Asp Gly Arg Arg Val
1               5                   10                  15

Pro Ile Gln Asp Leu Val Gly His Ser Pro Glu Val Ile Ala Val Asp
            20                  25                  30

Asp Lys Gly Arg Leu Val Cys Ala Lys Ser Glu Val Ile Trp Lys Val
        35                  40                  45

Gly Glu Arg Ser Val Phe Glu Ile Lys Leu Ala Ser Gly Arg Ser Ile
    50                  55                  60

Lys Ala Thr Ala Glu His Arg Leu Leu Ala Phe Lys Gly Trp Arg His
65                  70                  75                  80

Val Lys Asp Phe Lys Val Gly Asp Arg Leu Ala Ile Ala His
                85                  90
```

<210> SEQ ID NO 17
<211> LENGTH: 40
<212> TYPE: PRT
<213> ORGANISM: Artificial Sequence
<220> FEATURE:
<223> OTHER INFORMATION: Synthetic construct, Cbu_DnaB (12) C-intein

<400> SEQUENCE: 17

```
Met Ser Asp Leu Phe Trp Asp Arg Ile Val Ser Ile Glu Glu Lys Gly
1               5                   10                  15

Ser Glu Glu Val Tyr Asp Leu Thr Val Pro Lys Tyr Ala Ser Trp Leu
            20                  25                  30

Ala Asp Gly Val Val Ser His Asn
        35                  40
```

<210> SEQ ID NO 18
<211> LENGTH: 96
<212> TYPE: PRT
<213> ORGANISM: Artificial Sequence
<220> FEATURE:
<223> OTHER INFORMATION: Synthetic construct, Mja_GF-6P (44) N-intein

<400> SEQUENCE: 18

```
Cys Leu His Pro Asp Thr Tyr Val Ile Leu Pro Asp Gly Arg Met Lys
1               5                   10                  15

Lys Ile Ser Glu Ile Asp Glu Asp Val Leu Ser Val Asn Phe Glu
            20                  25                  30

Asp Leu Lys Leu Tyr Asn Lys Ile Lys Lys Phe Lys His Lys Ala
            35                  40                  45

Pro Lys Ile Leu Tyr Lys Ile Lys Thr Ala Phe Ser Glu Leu Ile Thr
        50                  55                  60

Thr Gly Glu His Lys Leu Phe Val Val Glu Asn Gly Lys Ile Val Glu
65                  70                  75                  80

Lys Cys Val Lys Asp Leu Asn Gly Ser Glu Leu Ile Gly Val Val Arg
                85                  90                  95
```

<210> SEQ ID NO 19
<211> LENGTH: 41
<212> TYPE: PRT
<213> ORGANISM: Artificial Sequence
<220> FEATURE:
<223> OTHER INFORMATION: Synthetic construct, Mja_GF-6P (44) C-intein

<400> SEQUENCE: 19

```
Met Ala Asp Ile Val Trp Thr Lys Phe Lys Ile Glu Glu Val Glu Ser
1               5                   10                  15

Asp Val Glu Tyr Val Tyr Asp Leu Glu Val Glu Asp Tyr His Asn Phe
            20                  25                  30

Ile Gly Asn Leu Ile Ile Asn His Asn
        35                  40
```

<210> SEQ ID NO 20
<211> LENGTH: 126
<212> TYPE: PRT
<213> ORGANISM: Artificial Sequence
<220> FEATURE:
<223> OTHER INFORMATION: Synthetic construct, Mja_Hyp-1 (46) N-intein

<400> SEQUENCE: 20

```
Cys Val Pro Pro Asp Thr Leu Leu Ile Leu Glu Asn Gly Phe Lys Arg
1               5                   10                  15

Ile Val Asp Ile Lys Val Gly Asp Lys Val Leu Thr His Glu Asn Arg
            20                  25                  30

Phe Lys Lys Val Glu Lys Val Tyr Lys Arg Arg Tyr Ile Gly Asp Ile
            35                  40                  45

Ile Lys Ile Lys Val Arg Tyr Phe Pro Glu Glu Ile Ile Leu Thr Pro
        50                  55                  60

Glu His Pro Val Tyr Ala Ile Lys Thr Glu Lys Arg Cys Asp Gly Ser
65                  70                  75                  80

His Gly Ile Cys Lys Phe Asn Cys Leu Thr Gln Tyr Thr Asn Pro Ser
                85                  90                  95

Cys Lys Lys Arg Tyr Arg Lys Tyr Lys Arg Glu Trp Ile Ile Ala Lys
            100                 105                 110

Asp Leu Lys Val Gly Asp Val Ile Val Tyr Pro Ile Pro Asn
        115                 120                 125
```

<210> SEQ ID NO 21
<211> LENGTH: 41
<212> TYPE: PRT
<213> ORGANISM: Artificial Sequence
<220> FEATURE:
<223> OTHER INFORMATION: Synthetic construct, Mja_Hyp-1 (46) C-intein -continued

```
<400> SEQUENCE: 21

Met Gly Asn Tyr Leu Tyr Ala Pro Ile Ile Arg Ile Gly Arg Glu Tyr
1               5                   10                  15

Tyr Asp Gly Phe Val Tyr Asn Leu Glu Val Glu Asp Ser Ser Tyr
            20                  25                  30

Val Thr Val Ser Gly Thr Leu His Asn
            35                  40

<210> SEQ ID NO 22
<211> LENGTH: 110
<212> TYPE: PRT
<213> ORGANISM: Artificial Sequence
<220> FEATURE:
<223> OTHER INFORMATION: Synthetic construct, Mja_IF2 (47) N-intein

<400> SEQUENCE: 22

Cys Leu Met Pro His Glu Lys Val Leu Thr Glu Tyr Gly Glu Ile Lys
1               5                   10                  15

Ile Glu Asp Leu Phe Lys Ile Gly Lys Glu Ile Val Glu Lys Asp Glu
            20                  25                  30

Leu Lys Glu Ile Arg Lys Leu Asn Ile Lys Val His Thr Leu Asn Glu
        35                  40                  45

Asn Gly Glu Ile Lys Ile Ile Asn Ala Pro Tyr Val Trp Lys Leu Lys
    50                  55                  60

His Lys Gly Lys Met Ile Lys Val Lys Leu Lys Asn Trp His Ser Ile
65                  70                  75                  80

Thr Thr Thr Pro Glu His Pro Phe Leu Thr Asn Asn Gly Trp Ile Lys
                85                  90                  95

Ala Glu Asn Ile Lys Lys Gly Met Tyr Val Ala Ile Pro Arg
            100                 105                 110

<210> SEQ ID NO 23
<211> LENGTH: 39
<212> TYPE: PRT
<213> ORGANISM: Artificial Sequence
<220> FEATURE:
<223> OTHER INFORMATION: Synthetic construct,  Mja_IF2 (47) C-intein

<400> SEQUENCE: 23

Met Asn Ile Ala Phe Val Glu Val Asp Val Glu Ile Ile Asp Tyr
1               5                   10                  15

Asp Gly Tyr Val Tyr Asp Leu Thr Thr Glu Thr His Asn Phe Ile Ala
            20                  25                  30

Asn Gly Ile Val Val His Asn
            35

<210> SEQ ID NO 24
<211> LENGTH: 102
<212> TYPE: PRT
<213> ORGANISM: Artificial Sequence
<220> FEATURE:
<223> OTHER INFORMATION: Synthetic construct, Mja_Pol-1 (50) N-intein

<400> SEQUENCE: 24

Cys His Pro Lys Gly Thr Lys Val Val Val Gly Lys Gly Ile Val
1               5                   10                  15

Asn Ile Glu Asp Val Lys Glu Gly Asn Tyr Val Leu Gly Ile Asp Gly
            20                  25                  30

Trp Gln Lys Val Lys Lys Val Trp Lys Tyr Glu Tyr Glu Gly Glu Leu
        35                  40                  45
```

```
Ile Asn Val Asn Gly Leu Lys Cys Thr Pro Asn His Lys Ile Pro Leu
         50                  55                  60

Arg Tyr Lys Ile Lys His Lys Lys Ile Asn Lys Asn Asp Tyr Leu Val
 65                  70                  75                  80

Arg Asp Ile Tyr Ala Lys Ser Leu Leu Thr Lys Phe Lys Gly Glu Gly
                 85                  90                  95

Lys Leu Ile Leu Cys Lys
            100

<210> SEQ ID NO 25
<211> LENGTH: 41
<212> TYPE: PRT
<213> ORGANISM: Artificial Sequence
<220> FEATURE:
<223> OTHER INFORMATION: Synthetic construct, Mja_Pol-1 (50) C-intein

<400> SEQUENCE: 25

Met Tyr Gly Phe Tyr Asp Leu Asp Val Cys Val Ser Leu Glu Ser
 1               5                  10                  15

Tyr Lys Gly Glu Val Tyr Asp Leu Thr Leu Glu Gly Arg Pro Tyr Tyr
                 20                  25                  30

Phe Ala Asn Gly Ile Leu Thr His Asn
             35                  40

<210> SEQ ID NO 26
<211> LENGTH: 122
<212> TYPE: PRT
<213> ORGANISM: Artificial Sequence
<220> FEATURE:
<223> OTHER INFORMATION: Synthetic construct, Pab_CDC21-1 (79) N-intein

<400> SEQUENCE: 26

Cys Val Asp Tyr Glu Thr Glu Val Val Leu Gly Asn Gly Glu Arg Lys
 1               5                  10                  15

Lys Ile Gly Glu Ile Val Glu Arg Ala Ile Glu Ala Glu Lys Asn
                 20                  25                  30

Gly Lys Leu Gly Arg Val Asp Asp Gly Phe Tyr Ala Pro Ile Asp Ile
             35                  40                  45

Glu Val Tyr Ser Leu Asp Leu Glu Thr Leu Lys Val Arg Lys Ala Arg
 50                  55                  60

Ala Asn Ile Ala Trp Lys Arg Thr Ala Pro Lys Lys Met Met Leu Val
 65                  70                  75                  80

Lys Thr Arg Gly Gly Lys Arg Ile Arg Val Thr Pro Thr His Pro Phe
                 85                  90                  95

Phe Val Leu Glu Glu Gly Lys Val Ala Met Arg Lys Ala Arg Asp Leu
            100                 105                 110

Glu Glu Gly Asn Lys Ile Ala Thr Ile Glu
            115                 120

<210> SEQ ID NO 27
<211> LENGTH: 41
<212> TYPE: PRT
<213> ORGANISM: Artificial Sequence
<220> FEATURE:
<223> OTHER INFORMATION: Synthetic construct, Pab_CDC21-1 (79) C-intein

<400> SEQUENCE: 27

Met Ser Val Ser Trp Asp Glu Val Ala Glu Ile Leu Glu Tyr Glu Pro
 1               5                  10                  15
```

```
Lys Asp Pro Trp Val Tyr Asp Leu Gln Val Pro Gly Tyr His Asn Phe
            20                  25                  30

Leu Ala Asn Gly Ile Phe Val His Asn
            35                  40

<210> SEQ ID NO 28
<211> LENGTH: 111
<212> TYPE: PRT
<213> ORGANISM: Artificial Sequence
<220> FEATURE:
<223> OTHER INFORMATION: Synthetic construct, Pab_IF2 (81) N-intein

<400> SEQUENCE: 28

Cys Leu Leu Pro Asp Glu Lys Val Val Pro Ser Val Gly Phe Val
1               5                   10                  15

Thr Leu Lys Glu Leu Phe Glu Thr Ala Ser Lys Val Val Glu Arg Asp
            20                  25                  30

Asp Glu Lys Glu Ile Arg Glu Leu Asp Glu Arg Ile Thr Ser Val Asn
            35                  40                  45

Gly Asp Gly Lys Thr Gly Leu Val Lys Ala Ser Tyr Val Trp Lys Val
        50                  55                  60

Arg His Lys Gly Lys Val Ile Arg Val Lys Leu Lys Asn Trp His Gly
65                  70                  75                  80

Val Thr Val Thr Pro Glu His Pro Phe Leu Thr Thr Lys Gly Trp Lys
                85                  90                  95

Arg Ala Asp Gln Leu Arg Pro Gly Asp Tyr Val Ala Val Pro Arg
            100                 105                 110

<210> SEQ ID NO 29
<211> LENGTH: 39
<212> TYPE: PRT
<213> ORGANISM: Artificial Sequence
<220> FEATURE:
<223> OTHER INFORMATION: Synthetic construct, Pab_IF2 (81) C-intein

<400> SEQUENCE: 29

Met Thr Leu Val Phe Ile Pro Val Glu Asn Val Glu Glu Glu Tyr
1               5                   10                  15

Asp Gly Tyr Val Tyr Asp Leu Thr Thr Glu Thr His Asn Phe Ile Ala
            20                  25                  30

Asn Gly Ile Leu Val His Asn
            35

<210> SEQ ID NO 30
<211> LENGTH: 121
<212> TYPE: PRT
<213> ORGANISM: Artificial Sequence
<220> FEATURE:
<223> OTHER INFORMATION: Synthetic construct, Pab_VMA (92) N-intein

<400> SEQUENCE: 30

Cys Val Asp Gly Asp Thr Leu Val Leu Thr Lys Glu Phe Gly Leu Ile
1               5                   10                  15

Lys Ile Lys Asp Leu Tyr Lys Ile Leu Asp Gly Lys Gly Lys Lys Thr
            20                  25                  30

Val Asn Gly Asn Glu Glu Trp Thr Glu Leu Glu Arg Pro Ile Thr Leu
            35                  40                  45

Tyr Gly Tyr Lys Asp Gly Lys Ile Val Glu Ile Lys Ala Thr His Val
        50                  55                  60

Tyr Lys Gly Phe Ser Ala Gly Met Ile Glu Ile Arg Thr Arg Thr Gly
```

```
                65                  70                  75                  80
Arg Lys Ile Lys Val Thr Pro Ile His Lys Leu Phe Thr Gly Arg Val
                    85                  90                  95

Thr Lys Asn Gly Leu Glu Ile Arg Glu Val Met Ala Lys Asp Leu Lys
                100                 105                 110

Lys Gly Asp Arg Ile Ile Val Ala Lys
        115                 120

<210> SEQ ID NO 31
<211> LENGTH: 42
<212> TYPE: PRT
<213> ORGANISM: Artificial Sequence
<220> FEATURE:
<223> OTHER INFORMATION: Synthetic construct, Pab_VMA (92) C-intein

<400> SEQUENCE: 31

Met Thr His Val Leu Phe Asp Glu Ile Val Glu Ile Arg Tyr Ile Ser
1               5                   10                  15

Glu Gly Gln Glu Val Tyr Asp Val Thr Thr Glu Thr His Asn Phe Ile
            20                  25                  30

Gly Gly Asn Met Pro Thr Leu Leu His Asn
        35                  40

<210> SEQ ID NO 32
<211> LENGTH: 111
<212> TYPE: PRT
<213> ORGANISM: Artificial Sequence
<220> FEATURE:
<223> OTHER INFORMATION: Synthetic construct, Pho_IF2 (103) N-intein

<400> SEQUENCE: 32

Cys Leu Leu Pro Glu Glu Arg Val Ile Leu Pro Asp Tyr Gly Pro Ile
1               5                   10                  15

Thr Leu Glu Glu Leu Phe Asn Met Thr Lys Glu Thr Val Phe Lys Asp
            20                  25                  30

Glu Glu Lys Glu Val Arg Lys Leu Gly Ile Arg Met Pro Val Ala Gly
        35                  40                  45

Val Asp Gly Arg Val Arg Leu Leu Glu Gly Pro Tyr Val Trp Lys Val
    50                  55                  60

Arg Tyr Lys Gly Lys Met Leu Arg Val Lys Leu Lys Asp Trp His Ser
65                  70                  75                  80

Val Ala Val Thr Pro Glu His Pro Phe Leu Thr Thr Arg Gly Trp Val
                85                  90                  95

Arg Ala Asp Gln Leu Lys Pro Gly Asp Tyr Val Ala Val Pro Lys
                100                 105                 110

<210> SEQ ID NO 33
<211> LENGTH: 39
<212> TYPE: PRT
<213> ORGANISM: Artificial Sequence
<220> FEATURE:
<223> OTHER INFORMATION: Synthetic construct, Pho_IF2 (103) C-intein

<400> SEQUENCE: 33

Met Asn Phe Val Phe Leu Pro Val Glu Lys Ile Glu Glu Phe Glu Tyr
1               5                   10                  15

Asp Gly Tyr Val Tyr Asp Val Thr Thr Glu Thr His Asn Phe Ile Ala
            20                  25                  30

Asn Gly Ile Leu Val His Asn
        35
```

```
<210> SEQ ID NO 34
<211> LENGTH: 121
<212> TYPE: PRT
<213> ORGANISM: Artificial Sequence
<220> FEATURE:
<223> OTHER INFORMATION: Synthetic construct, Pho_VMA (110) N-intein

<400> SEQUENCE: 34

Cys Val Asp Gly Asp Thr Leu Val Leu Thr Lys Glu Phe Gly Leu Ile
1               5                   10                  15

Lys Ile Lys Glu Leu Tyr Glu Lys Leu Asp Gly Lys Gly Arg Lys Ile
            20                  25                  30

Val Glu Gly Asn Glu Glu Trp Thr Glu Leu Glu Lys Pro Ile Thr Val
        35                  40                  45

Tyr Gly Tyr Lys Asp Gly Lys Ile Val Glu Ile Lys Ala Thr His Val
    50                  55                  60

Tyr Lys Gly Val Ser Ser Gly Met Val Glu Ile Arg Thr Arg Thr Gly
65                  70                  75                  80

Arg Lys Ile Lys Val Thr Pro Ile His Arg Leu Phe Thr Gly Arg Val
                85                  90                  95

Thr Lys Asp Gly Leu Ile Leu Lys Glu Val Met Ala Met His Val Lys
            100                 105                 110

Pro Gly Asp Arg Ile Ala Val Val Lys
        115                 120

<210> SEQ ID NO 35
<211> LENGTH: 42
<212> TYPE: PRT
<213> ORGANISM: Artificial Sequence
<220> FEATURE:
<223> OTHER INFORMATION: Synthetic construct, Pho_VMA (110) C-intein

<400> SEQUENCE: 35

Met Gln His Ile Ile Phe Asp Glu Val Ile Asp Val Arg Tyr Ile Pro
1               5                   10                  15

Glu Pro Gln Glu Val Tyr Asp Val Thr Thr Glu Thr His Asn Phe Val
            20                  25                  30

Gly Gly Asn Met Pro Thr Leu Leu His Asn
        35                  40

<210> SEQ ID NO 36
<211> LENGTH: 96
<212> TYPE: PRT
<213> ORGANISM: Artificial Sequence
<220> FEATURE:
<223> OTHER INFORMATION: Synthetic construct, Rma_DnaB (116) N-intein

<400> SEQUENCE: 36

Cys Leu Ala Gly Asp Thr Leu Ile Thr Leu Ala Asp Gly Arg Arg Val
1               5                   10                  15

Pro Ile Arg Glu Leu Val Ser Gln Gln Asn Phe Ser Val Trp Ala Leu
            20                  25                  30

Asn Pro Gln Thr Tyr Arg Leu Glu Arg Ala Arg Val Ser Arg Ala Phe
        35                  40                  45

Cys Thr Gly Ile Lys Pro Val Tyr Arg Leu Thr Thr Arg Leu Gly Arg
    50                  55                  60

Ser Ile Arg Ala Thr Ala Asn His Arg Phe Leu Thr Pro Gln Gly Trp
65                  70                  75                  80
```

Lys Arg Val Asp Glu Leu Gln Pro Gly Asp Tyr Leu Ala Leu Pro Arg
            85                  90                  95

<210> SEQ ID NO 37
<211> LENGTH: 40
<212> TYPE: PRT
<213> ORGANISM: Artificial Sequence
<220> FEATURE:
<223> OTHER INFORMATION: Synthetic construct, Rma_DnaB (116) C-intein

<400> SEQUENCE: 37

Met Ser Asp Val Tyr Trp Asp Pro Ile Val Ser Ile Glu Pro Asp Gly
1               5                   10                  15

Val Glu Glu Val Phe Asp Leu Thr Val Pro Gly Pro His Asn Phe Val
            20                  25                  30

Ala Asn Asp Ile Ile Ala His Asn
        35                  40

<210> SEQ ID NO 38
<211> LENGTH: 89
<212> TYPE: PRT
<213> ORGANISM: Artificial Sequence
<220> FEATURE:
<223> OTHER INFORMATION: Synthetic construct, Sru_DnaB (123) N-intein

<400> SEQUENCE: 38

Cys Leu Gly Lys Gly Thr Pro Val Met Met Tyr Asp Gly Arg Thr Lys
1               5                   10                  15

Pro Val Glu Lys Val Glu Val Gly Asp Arg Leu Met Gly Asp Asp Gly
            20                  25                  30

Ser Pro Arg Thr Val Gln Ser Leu Ala Arg Gly Arg Glu Gln Met Tyr
        35                  40                  45

Trp Val Arg Gln Lys Arg Gly Met Asp Tyr Arg Val Asn Glu Ser His
    50                  55                  60

Ile Leu Ser Leu Lys Lys Ser Arg Arg Glu Gly Ala Arg Asp Arg Gly
65                  70                  75                  80

Ser Ile Ala Asp Ile Ser Val Arg Asp
                85

<210> SEQ ID NO 39
<211> LENGTH: 38
<212> TYPE: PRT
<213> ORGANISM: Artificial Sequence
<220> FEATURE:
<223> OTHER INFORMATION: Synthetic construct, Sru_DnaB (123) C-intein

<400> SEQUENCE: 39

Met Trp Arg Met Thr Gly Ile Asp Val Glu Pro Asp Gly Val Gly Asp
1               5                   10                  15

Tyr Phe Gly Phe Thr Leu Asp Gly Asn Gly Arg Phe Leu Leu Gly Asp
            20                  25                  30

Gly Thr Val Thr His Asn
        35

<210> SEQ ID NO 40
<211> LENGTH: 95
<212> TYPE: PRT
<213> ORGANISM: Artificial Sequence
<220> FEATURE:
<223> OTHER INFORMATION: Synthetic construct,Tag_Pol-1_Tsp-TY_Pol-1
      (128) N-intein

<400> SEQUENCE: 40

Cys His Pro Ala Asp Thr Lys Val Ile Val Lys Gly Lys Gly Ile Val
1               5                   10                  15

Asn Ile Ser Asp Val Lys Glu Gly Asp Tyr Ile Leu Gly Ile Asp Gly
            20                  25                  30

Trp Gln Arg Val Lys Lys Val Trp Lys Tyr His Tyr Glu Gly Lys Leu
        35                  40                  45

Ile Asn Ile Asn Gly Leu Lys Cys Thr Pro Asn His Lys Val Pro Val
50                  55                  60

Val Thr Glu Asn Asp Arg Gln Thr Arg Ile Arg Asp Ser Leu Ala Lys
65                  70                  75                  80

Ser Phe Leu Ser Gly Lys Val Lys Gly Lys Ile Ile Thr Thr Lys
            85                  90                  95

<210> SEQ ID NO 41
<211> LENGTH: 41
<212> TYPE: PRT
<213> ORGANISM: Artificial Sequence
<220> FEATURE:
<223> OTHER INFORMATION: Synthetic construct,Tag_Pol-1_Tsp-TY_Pol-1
      (128) C-intein

<400> SEQUENCE: 41

Met Asn Ser Phe Tyr Asn Leu Ser Thr Phe Glu Val Ser Ser Glu Tyr
1               5                   10                  15

Tyr Lys Gly Glu Val Tyr Asp Leu Thr Leu Glu Gly Asn Pro Tyr Tyr
            20                  25                  30

Phe Ala Asn Gly Ile Leu Thr His Asn
            35                  40

<210> SEQ ID NO 42
<211> LENGTH: 107
<212> TYPE: PRT
<213> ORGANISM: Artificial Sequence
<220> FEATURE:
<223> OTHER INFORMATION: Synthetic construct, Ter_RIR1-4 (135) N-intein

<400> SEQUENCE: 42

Cys Leu Asp Lys Thr Ala Leu Arg Ile Phe Asn Gln Gly Leu Leu Tyr
1               5                   10                  15

Ala Asp Glu Val Val Thr Pro Gly Ser Gly Glu Thr Val Gly Leu Gly
            20                  25                  30

Leu Thr Val Arg Asn Gly Ile Gly Ala Ser Thr Ala Ile Ala Asn Gln
            35                  40                  45

Pro Met Glu Leu Val Glu Ile Lys Leu Ala Asn Gly Arg Lys Leu Arg
50                  55                  60

Met Thr Pro Asn His Arg Met Ser Val Lys Gly Lys Trp Ile His Ala
65                  70                  75                  80

Cys Asn Leu Lys Pro Gly Met Leu Leu Asp Tyr Ser Ile Gly Glu Tyr
            85                  90                  95

Gln Lys Arg Glu Asp Thr Leu Leu Ile Pro Leu
            100                 105

<210> SEQ ID NO 43
<211> LENGTH: 49
<212> TYPE: PRT
<213> ORGANISM: Artificial Sequence
<220> FEATURE:
<223> OTHER INFORMATION: Synthetic construct, Ter_RIR1-4 (135) C-intein

<400> SEQUENCE: 43

```
Met Ser Lys Cys Val Leu Asn Tyr Ser Pro Tyr Lys Ile Glu Ser Val
1               5                   10                  15

Asn Ile Gly Ala Val Cys Asp Tyr Ser Tyr Asp Phe Ala Ile Glu Gly
                20                  25                  30

Ile Asn Asp Asn Asp Ser Trp Tyr Trp Gln Gly Ala Leu Lys Ser His
            35                  40                  45

Asn
```

<210> SEQ ID NO 44
<211> LENGTH: 111
<212> TYPE: PRT
<213> ORGANISM: Artificial Sequence
<220> FEATURE:
<223> OTHER INFORMATION: Synthetic construct, Tko_IF2 (143) N-intein

<400> SEQUENCE: 44

```
Cys Leu Leu Pro Asp Glu Lys Val Ile Leu Pro Glu His Gly Pro Ile
1               5                   10                  15

Thr Leu Lys Gly Leu Phe Asp Leu Ala Lys Glu Thr Val Val Ala Asp
                20                  25                  30

Asn Glu Lys Glu Ile Arg Lys Leu Gly Ala Lys Leu Thr Ile Val Gly
            35                  40                  45

Glu Asp Gly Arg Leu Arg Val Leu Glu Ser Pro Tyr Val Trp Lys Val
50                  55                  60

Arg His Arg Gly Lys Met Leu Arg Val Lys Leu Lys Asn Trp His Ser
65                  70                  75                  80

Val Ser Val Thr Pro Glu His Pro Phe Leu Thr Thr Arg Gly Trp Val
                85                  90                  95

Arg Ala Asp Gln Leu Lys Pro Gly Asp Tyr Val Ala Val Pro Arg
            100                 105                 110
```

<210> SEQ ID NO 45
<211> LENGTH: 39
<212> TYPE: PRT
<213> ORGANISM: Artificial Sequence
<220> FEATURE:
<223> OTHER INFORMATION: Synthetic construct, Tko_IF2 (143) C-intein

<400> SEQUENCE: 45

```
Met Asn Leu Val Phe Ile Pro Val Glu Asp Ile Glu Glu Phe Glu Tyr
1               5                   10                  15

Glu Gly Tyr Val Tyr Asp Val Thr Thr Glu Thr His Asn Phe Val Ala
                20                  25                  30

Asn Gly Ile Leu Val His Asn
            35
```

<210> SEQ ID NO 46
<211> LENGTH: 98
<212> TYPE: PRT
<213> ORGANISM: Artificial Sequence
<220> FEATURE:
<223> OTHER INFORMATION: Synthetic construct, Tth-HB27_DnaE-2 (15)
      N-intein

<400> SEQUENCE: 46

```
Leu Pro Ala Arg Ala Arg Val Val Asp Trp Cys Thr Gly Arg Val Val
1               5                   10                  15

Arg Val Gly Glu Ile Val Arg Gly Glu Ala Lys Gly Val Trp Val Val
                20                  25                  30
```

```
Ser Leu Asp Glu Ala Arg Leu Arg Leu Val Pro Arg Pro Val Val Ala
         35                  40                  45

Ala Phe Pro Ser Gly Lys Ala Gln Val Tyr Ala Leu Arg Thr Ala Thr
 50                  55                  60

Gly Arg Val Leu Glu Ala Thr Ala Asn His Pro Val Tyr Thr Pro Glu
 65                  70                  75                  80

Gly Trp Arg Pro Leu Gly Thr Leu Ala Pro Gly Asp Tyr Val Ala Leu
                 85                  90                  95

Pro Arg

<210> SEQ ID NO 47
<211> LENGTH: 40
<212> TYPE: PRT
<213> ORGANISM: Artificial Sequence
<220> FEATURE:
<223> OTHER INFORMATION: Synthetic construct, Tth-HB27_DnaE-2 (15)
      C-intein

<400> SEQUENCE: 47

Met Ala Glu Val Tyr Trp Asp Arg Val Glu Ala Val Glu Pro Leu Gly
 1               5                  10                  15

Glu Glu Glu Val Phe Asp Leu Thr Val Glu Gly Thr His Thr Phe Val
                 20                  25                  30

Ala Glu Asp Val Ile Val His Asn
         35                  40

<210> SEQ ID NO 48
<211> LENGTH: 13
<212> TYPE: DNA
<213> ORGANISM: Artificial Sequence
<220> FEATURE:
<223> OTHER INFORMATION: Synthetic construct, frameshifted RBS

<400> SEQUENCE: 48
aaggagatat acc                                                         13

<210> SEQ ID NO 49
<211> LENGTH: 378
<212> TYPE: PRT
<213> ORGANISM: Artificial Sequence
<220> FEATURE:
<223> OTHER INFORMATION: Synthetic construct, iSavinase S317_gp41-1-NI

<400> SEQUENCE: 49

Met Ala Glu Glu Ala Lys Glu Lys Tyr Leu Ile Gly Phe Asn Glu Gln
 1               5                  10                  15

Glu Ala Val Ser Glu Phe Val Glu Gln Val Glu Ala Asn Asp Glu Val
                 20                  25                  30

Ala Ile Leu Ser Glu Glu Glu Val Glu Ile Glu Leu Leu His Glu
         35                  40                  45

Phe Glu Thr Ile Pro Val Leu Ser Val Glu Leu Ser Pro Glu Asp Val
 50                  55                  60

Asp Ala Leu Glu Leu Asp Pro Ala Ile Ser Tyr Ile Glu Glu Asp Ala
 65                  70                  75                  80

Glu Val Thr Thr Met Ala Gln Ser Val Pro Trp Gly Ile Ser Arg Val
                 85                  90                  95

Gln Ala Pro Ala Ala His Asn Arg Gly Leu Thr Gly Ser Gly Val Lys
                100                 105                 110

Val Ala Val Leu Asp Thr Gly Ile Ser Thr His Pro Asp Leu Asn Ile
            115                 120                 125
```

Arg Gly Gly Ala Ser Phe Val Pro Gly Glu Pro Ser Thr Gln Asp Gly
130                 135                 140

Asn Gly His Gly Thr His Val Ala Gly Thr Ile Ala Ala Leu Asn Asn
145                 150                 155                 160

Ser Ile Gly Val Leu Gly Val Ala Pro Ser Ala Glu Leu Tyr Ala Val
            165                 170                 175

Lys Val Leu Gly Ala Ser Gly Ser Gly Ser Val Ser Ser Ile Ala Gln
            180                 185                 190

Gly Leu Glu Trp Ala Gly Asn Asn Gly Met His Val Ala Asn Leu Ser
            195                 200                 205

Leu Gly Ser Pro Ser Pro Ser Ala Thr Leu Glu Gln Ala Val Asn Ser
210                 215                 220

Ala Thr Ser Arg Gly Val Leu Val Val Ala Ala Ser Gly Asn Ser Gly
225                 230                 235                 240

Ala Gly Ser Ile Ser Tyr Pro Ala Arg Tyr Ala Asn Ala Met Ala Val
            245                 250                 255

Gly Ala Thr Asp Gln Asn Asn Arg Ala Ser Phe Ser Gln Tyr Gly
            260                 265                 270

Ala Gly Leu Asp Ile Val Ala Pro Gly Val Asn Val Gln Ser Thr Tyr
            275                 280                 285

Pro Gly Cys Leu Asp Leu Lys Thr Gln Val Gln Thr Pro Gln Gly Met
290                 295                 300

Lys Glu Ile Ser Asn Ile Gln Val Gly Asp Leu Val Leu Ser Asn Thr
305                 310                 315                 320

Gly Tyr Asn Glu Val Leu Asn Val Phe Pro Lys Ser Lys Lys Lys Ser
            325                 330                 335

Tyr Lys Ile Thr Leu Glu Asp Gly Lys Glu Ile Ile Cys Ser Glu Glu
            340                 345                 350

His Leu Phe Pro Thr Gln Thr Gly Glu Met Asn Ile Ser Gly Gly Leu
            355                 360                 365

Lys Glu Gly Met Cys Leu Tyr Val Lys Glu
            370                 375

<210> SEQ ID NO 50
<211> LENGTH: 101
<212> TYPE: PRT
<213> ORGANISM: Artificial Sequence
<220> FEATURE:
<223> OTHER INFORMATION: Synthetic construct, iSavinase S317_gp41-1-IC

<400> SEQUENCE: 50

Met Met Leu Lys Lys Ile Leu Lys Ile Glu Glu Leu Asp Glu Arg Glu
1               5                   10                  15

Leu Ile Asp Ile Glu Val Ser Gly Asn His Leu Phe Tyr Ala Asn Asp
            20                  25                  30

Ile Leu Thr His Asn Ser Thr Tyr Ala Ser Leu Asn Gly Thr Ser Met
        35                  40                  45

Ala Thr Pro His Val Ala Gly Ala Ala Leu Val Lys Gln Lys Asn
    50                  55                  60

Pro Ser Trp Ser Asn Val Gln Ile Arg Asn His Leu Lys Asn Thr Ala
65                  70                  75                  80

Thr Ser Leu Gly Ser Thr Asn Leu Tyr Gly Ser Gly Leu Val Asn Ala
                85                  90                  95

Glu Ala Ala Thr Arg
            100

<210> SEQ ID NO 51
<211> LENGTH: 118
<212> TYPE: PRT
<213> ORGANISM: Artificial Sequence
<220> FEATURE:
<223> OTHER INFORMATION: Synthetic construct, Trx-1

<400> SEQUENCE: 51

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Leu Gln Val
            100                 105                 110

Asp Lys Leu Ala Ala Ala
        115

<210> SEQ ID NO 52
<211> LENGTH: 357
<212> TYPE: DNA
<213> ORGANISM: Artificial Sequence
<220> FEATURE:
<223> OTHER INFORMATION: Synthetic construct, Trx-1 coding sequence

<400> SEQUENCE: 52
atgagcgata aaattattca cctgactgac gacagttttg acacggatgt actcaaagcg      60
gacggggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggccctg caggtcgaca gcttgcggc cgcataa        357

<210> SEQ ID NO 53
<211> LENGTH: 109
<212> TYPE: PRT
<213> ORGANISM: Artificial Sequence
<220> FEATURE:
<223> OTHER INFORMATION: Synthetic construct, Trx-2

<400> SEQUENCE: 53

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 54
<211> LENGTH: 327
<212> TYPE: DNA
<213> ORGANISM: Artificial Sequence
<220> FEATURE:
<223> OTHER INFORMATION: Synthetic construct, Trx-2 coding sequence

<400> SEQUENCE: 54
atgagcgata aaattattca cctgactgac gacagttttg acacggatgt actcaaagcg      60 gacgggcga tcctcgtcga tttctgggca gagtggtgcg gtccgtgcaa atgatcgcc      120 ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggcc                                         327

<210> SEQ ID NO 55
<211> LENGTH: 5
<212> TYPE: PRT
<213> ORGANISM: Artificial Sequence
<220> FEATURE:
<223> OTHER INFORMATION: Synthetic construct, GGGGS linker

<400> SEQUENCE: 55

Gly Gly Gly Gly Ser
1               5

<210> SEQ ID NO 56
<211> LENGTH: 6
<212> TYPE: PRT
<213> ORGANISM: Artificial Sequence
<220> FEATURE:
<223> OTHER INFORMATION: Syntehtic construct, GGGGGS linker

<400> SEQUENCE: 56

Gly Gly Gly Gly Gly Ser
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic construct, GGGGG linker

<400> SEQUENCE: 57

Gly Gly Gly Gly Gly
1               5

<210> SEQ ID NO 58
<211> LENGTH: 213
<212> TYPE: PRT
<213> ORGANISM: Artificial Sequence
<220> FEATURE:
<223> OTHER INFORMATION: Synthetic construct, Trx-DPNG-MTT-IC_S326A

<400> SEQUENCE: 58

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65              70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Asp Pro Asn
                100                 105                 110

Gly Met Thr Lys Lys Ile Thr Lys Ile Glu Glu Leu Asp Glu Arg Glu
                115                 120                 125

Leu Ile Asp Ile Glu Val Ser Gly Asn His Leu Phe Tyr Ala Asn Asp
    130                 135                 140

Ile Gly Thr His Asn Ser Thr Tyr Ala Ser Leu Asn Gly Thr Ala Met
145             150                 155                 160

Ala Thr Pro His Val Ala Gly Ala Ala Leu Val Lys Gln Lys Asn
                165                 170                 175

Pro Ser Trp Ser Asn Val Gln Ile Arg Asn His Leu Lys Asn Thr Ala
                180                 185                 190

Thr Ser Leu Gly Ser Thr Asn Leu Tyr Gly Ser Gly Leu Val Asn Ala
            195                 200                 205

Glu Ala Ala Thr Arg
            210

<210> SEQ ID NO 59
<211> LENGTH: 642
<212> TYPE: DNA
<213> ORGANISM: Artificial Sequence
<220> FEATURE:
<223> OTHER INFORMATION: Synthetic construct, Trx-DPNG-MTT-IC_S326A
      coding seq

<400> SEQUENCE: 59
atgagcgata aaattattca cctgactgac gacagttttg acacggatgt actcaaagcg      60
gacggggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggccgat cctaatggta tgacgaagaa attacgaag      360 atcgaagaac tggatgaacg tgaactgatt gacatcgaag ttagcggcaa ccatctgttt     420
tacgcgaatg acattgggac ccacaactca acttatgcca gcttaaacgg tacacggatg     480
gctactcctc atgttgcagg tgcggccgcc cttgttaaac aaaagaaccc atcttggtct     540
aatgtacaaa ttcgaaatca tctaaagaat acggcaacta gtttaggaag cacgaacttg     600
tatggaagcg gacttgttaa cgcagaagcg gcaacgcgtt aa                        642
```

METHODS AND COMPOSITIONS FOR STABILIZING TRANS-SPLICING INTEIN MODIFIED PROTEASES

CROSS REFERENCE TO RELATED APPLICATIONS

This application is a continuation of U.S. patent application Ser. No. 15/519,602, which was filed on Apr. 17, 2017 as a 35 U.S.C. § 371 national phase application of PCT/US2015/057862, which was filed Oct. 28, 2015, and claimed the benefit of U.S. Provisional Application No. 62/069,653, which was filed Oct. 28, 2014, all of which are incorporated herein by reference as if fully set forth.

The sequence listing electronically filed with this application titled "Sequence Listing," which was created on Jun. 11, 2020 and had a size of 62,147 bytes is incorporated by reference herein as if fully set forth.

FIELD

The disclosure relates to methods and compositions enabling tight regulation of trans-splicing intein modified protease activity in liquid detergents and home care products, for stable storage in the formulations and efficient recovery of protease activity quickly, with reduced loss of cleaning efficiency.

BACKGROUND

Proteases are common ingredients in a variety of liquid detergents, laundry detergents, dish-washing liquids, paints, coatings and industrial cleaners. Proteases are notoriously difficult to handle in formulations because they not only degrade other proteins but can self digest. Therefore protease stabilization remains one of the biggest challenges facing the liquid detergent industry. Current stabilization technologies are often based on the use of high concentrations of chemical protease inhibitors, increasing the chemical load and cost. It would be desirable to have a more environmentally friendly, bio-based and low cost solution to stabilize protease enzymes but without compromising product performance. Previously it was demonstrated that the trans-splicing intein technology could be used to control protease activity.

SUMMARY

An aspect of the invention relates to an intein-modified protease. The intein-modified protease comprises a first precursor and a second precursor. The first precursor comprises an N-extein of a target protease and a solubility enhanced N-intein of a trans-splicing intein. The carboxy terminus of the N-extein is fused to the amino terminus of the solubility enhanced N-intein. The second precursor comprises a solubility enhanced C-intein of the trans-splicing intein and a C-extein of the target protease. The carboxy terminus of the solubility enhanced C-intein is fused to the amino terminus of the C-extein. The first precursor is separated from the second precursor prior to splicing. The intein-modified protease has enhanced solubility and reduced activity compared to the target protease. The activity of the target protease is obtained upon trans-splicing of the intein-modified protease and fusion of the N-extein and the C-extein.

An aspect of the invention relates to an expression cassette. The expression cassette comprises one or more polynucleotides encoding a first precursor or a second precursor of an intein-modified protease. The first precursor comprises an N-extein of a target protease and a solubility enhanced N-intein of a trans-splicing intein. The carboxy terminus of the N-extein is fused to the amino terminus of the solubility enhanced N-intein. The second precursor comprises a solubility enhanced C-intein of the trans-splicing intein and a C-extein of the target protease. The carboxy terminus of the solubility enhanced C-intein is fused to the amino terminus of the C-extein. Upon expression from the expression cassette the first precursor would be separated from the second precursor prior to splicing. The intein-modified protease would have enhanced solubility and reduced or inhibited activity compared to the target protease. The activity of the target protease would be restored upon trans-splicing of the intein-modified protease and fusion of the N-extein and the C-extein.

An aspect of the invention relates to a composition comprising: a first precursor of an intein-modified protease and a second precursor of an intein-modified protease. The first precursor comprises an N-extein of a target protease fused to a solubility enhanced N-intein of a trans-splicing intein. The carboxy terminus of the N-extein is fused to the amino terminus of the solubility enhanced N-intein. The second precursor comprises a solubility enhanced C-intein of the trans-splicing intein fused to a C-extein of the target protease. The carboxy terminus of the solubility enhanced C-intein is fused to the amino terminus of the C-extein. The first precursor is separated from the second precursor prior to trans-splicing. The intein-modified protease has enhanced solubility and reduced activity compared to the target protease and the activity of the target protease is obtained upon trans-splicing of the intein-modified protease and fusion of the N-extein and the C-extein.

An aspect of the invention relates to a home care product that includes any one of the intein-modified proteases or the compositions disclosed herein, and one or more effectors.

An aspect of the invention relates to a method of regulating protease activity. The method comprises forming any one of the home care products disclosed herein.

An aspect of the invention relates to a method of storing a protease in a mixture. The method includes making any one of intein-modified proteases or the compositions disclosed herein. The method also includes combining the intein-modified protease or the composition with at least one agent selected from the group consisting of: a detergent, a soap, an industrial cleaner, and a dishwashing liquid with one or more effectors to form a mixture.

BRIEF DESCRIPTION OF THE DRAWINGS

The following detailed description of the embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIG. 2A illustrates total protein profiles. FIG. 2B illustrates soluble protein profiles.

FIG. 5A illustrates dilution induction. FIG. 5B illustrates salt suppression.

FIG. 6A illustrates iProtease (iSavinase; NI (SEQ ID NO: 1) and IC (SEQ ID NO: 2)) activity in serial dilutions of the high salt associated (NI+IC) premix in the BR buffer. FIG. 6B illustrates iProtease (iSavinase; NI (SEQ ID NO: 1) and IC (SEQ ID NO: 2)) activity in mixes of separate serial dilutions of NI and IC (NI-IC) in the BR buffer.

FIG. 7A illustrates protein profiles after dilution of the unsalted premix in the aqueous buffer. FIG. 7B illustrates protein profiles after dilution of the salted premix in the aqueous buffer.

FIG. 8A illustrates the dilution activity profile of iProtease (iSavinase; NI (SEQ ID NO: 1) and IC (SEQ ID NO: 2)). FIG. 8B illustrates the dilution activity profile of Savinase (SEQ ID NO: 6).

FIGS. 9A-9B illustrate that the KCl stabilized (NI (SEQ ID NO: 1)+IC (SEQ ID NO: 2), intein-modified precursors of iSavinase or iSav) premix has no enzyme activity for iProtease (iSavinase) (FIG. 9A) and Savinase (SEQ ID NO: 6) (FIG. 9B).

FIG. 10A illustrates iProtease activity for the premix not stored. FIG. 10B illustrates iProtease activity for the premix stored for 8 weeks.

FIG. 11A illustrates the dilution activities from 1M KCl. FIG. 11B illustrates the dilution activities from 50% Detergent-1 lacking 1M KCl.

FIG. 19A illustrates protease (iSavinase; NI (SEQ ID NO: 1) and IC (SEQ ID NO: 2)) activity following splicing of inteins 12, 12, 44, 46, 47, 50, 79, 81 and 103. FIG. 19B illustrates protease activity following splicing of inteins 110, 116, 123, 128, 135, 143, and 150.

DETAILED DESCRIPTION OF EMBODIMENTS OF THE INVENTION

Figure 1:
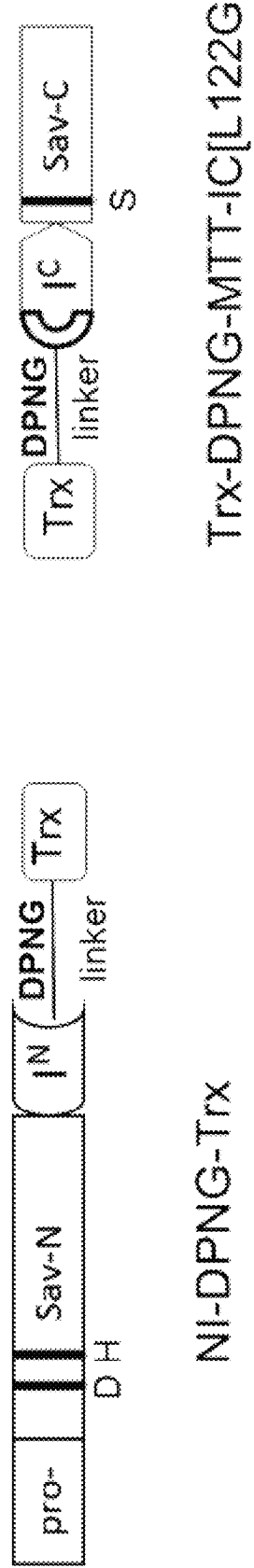
FIG. 1 illustrates schematic drawings of solubility optimized trans-splicing NI and IC.

Certain terminology is used in the following description for convenience only and is not limiting. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

An embodiment comprises an intein-modified protease having enhanced solubility. The intein-modified protease may comprise components that together comprise a target protease and an intein fused to the target protease in such a position as to control the activity of the target protease. Both the target protease and the intein are split into two parts, and one part of the target protein is fused with one part of the intein, while the other part of the target protein is fused to the other part of the intein. Although the two fused sequences are separate entities, they are collectively referred to herein as an "intein-modified protease." The separate fusions may be referred to as a "first precursor" and "second precursor." Collectively, the first precursor and the second precursor may be referred to as components of the intein-modified protease. As used herein, N-extein and N-intein refer to the amino terminal parts of the target protease and intein, respectively. Likewise, C-extein and C-intein refer to the carboxy terminal parts of the target protease and intein, respectively.

The intein in an intein-modified protease is a trans-splicing intein capable of effecting trans-splicing of the intein-modified protease. The first precursor comprises an N-extein of the target protease and a solubility enhanced N-intein of the trans-splicing intein. The carboxy terminus of the N-extein may be fused to the amino terminus of the solubility enhanced N-intein. The solubility enhanced N-intein may comprise a first solubility enhancer. The carboxy terminus of the N-intein may be fused to the first solubility enhancer by a first linker. The second precursor comprises a solubility enhanced C-intein of the trans-splicing intein and a C-extein of the target protease. The carboxy terminus of the solubility enhanced C-intein may be fused to the amino terminus of the C-extein. The solubility enhanced C-intein may comprise a second solubility enhancer. The second solubility enhancer may be fused to the amino terminus of the C-intein by a second linker. The first precursor is separated from the second precursor prior to splicing of the intein-modified protease.

In an embodiment, at least one of the first solubility enhancer or the second solubility enhancer may comprise, consist essentially of, or consist of a thioredoxin domain (Trx), small ubiquitin-related protein (SUMO), glutathione-S transferase (GST), maltose-binding protein (MBP), N utilization substance (A NusA), or seventeen kilo Dalton protein (Skp). The first solubility enhancer may be the same or different solubility enhancer than the second solubility enhancer. At least one of the first solubility enhancer or the second solubility enhancer may be Trx. The first solubility enhancer may comprise, consist essentially of, or consist of an amino acid sequence with at least 70, 72, 75, 80, 85, 90, 91, 92, 93, 94, 95, 96, 97, 98, 99 or 100% identity to SEQ ID NO: 51. The second solubility enhancer may comprise, consist essentially of, or consist of an amino acid sequence with at least 70, 72, 75, 80, 85, 90, 91, 92, 93, 94, 95, 96, 97, 98, 99 or 100% identity to SEQ ID NO: 53. A solubility enhancer may any other molecule capable of enhancing solubility of the first precursor or the second precursor. A solubility enhancer may be covalently linked or fused to an intein.

In an embodiment, the first linker or the second linker may be any linker suitable for linking a solubility enhancer to the N-intein or the C-intein. The linker may be of variable length, composition and flexibility. The linker may be short and flexible. The linker may comprise a stretch of glycine (G) and serine (S) residue. The linker may include an amino acid sequence of GGGGS (SEQ ID NO: 55), GGGGGS (SEQ ID NO: 56) or GGGGG (SEQ ID NO: 57). The linker may be configured to define a small structural turn to keep the solubility enhancer domains of the first precursor or the second precursor away from the interface of the split intein pair. Structural modeling can be used to predict the best fit length and composition of the linker.

In an embodiment, at least one of the first linker or the second linker may be a DPNG linker. The DPNG linker may comprise an amino acid sequence of SEQ ID NO: 5. The first linker or the second linker may be any other suitable linker.

The target protease may be any protease. As described, the target protease is split into two parts when intein modified, and the intein modified parts will comprise the first precursor and the second precursor. As used herein, "protease" refers to an enzyme or portion thereof that catalyzes hydrolysis of peptide bonds. The enzyme may be but is not limited to an amino acid sequence or protein herein having the activity of catalyzing hydrolysis of peptide bonds. The enzyme may be a variant of an amino acid sequence or protein herein and have the activity of catalyzing hydrolysis of peptide bonds, where the variant is a mutant and/or part of the amino acid sequence or protein. The variant may have at least 40% of the activity of the amino acid sequence or protein having the activity of catalyzing hydrolysis of peptide bonds. Activity may be analyzed by the enzyme assay outlined in Example 2 with respect to Savinase activity.

The target protease may be an enzyme classified under EC 3.4 as peptide hydrolases. The target protease be one classified under EC 3.4.99, EC 3.4.21.62, serine proteases, alkaline proteases, keratinases, and others. The target protease may be but is not limited to: a metallo protease, a cysteine protease, an aspartate protease, or an ATP-dependent protease.

In an embodiment, the target protease may be an alkaline protease. The alkaline protease may be a protease from Subtilisin family. The target protease may be a Subtilisin from *B. lentus* (BL, P29599); Subtilisin from *B. pumilus* (PO7518); Subtilisin from *B. subtilis* (E, P04189); Subtilisin from *B. licheniformis* (DY, P00781); Subtilisin from *B. amyloliquefaciens* (BPN, P00782); Subtilisin from *Bacillus* sp. strain TA39 (P28842); Subtilisin from *Geobacillus stearothermophilus* (J, P29142); Subtilisin from *B. subtilis* subsp. Natto (NAT, P35835); Subtilisin from *B. licheniformis* (Carlsberg, P00780); Subtilisin from *B. subtilis* subsp. *Amylosacchariticus*, (*Amylosacchariticus*, P00780); Subtilisin Carlsberg; Subtilisin BPN; or Subtilisin SAPB from *Bacillus pumilus* (CBS).

The protease from the Subtilisin family may be Savinase. Savinase is an extracellular alkaline protease from *Bacillus lentus* (Uniprot accession number is: P29600 and a common protease in liquid laundry detergents. The target protease may comprise, consist essentially of, or consist of a sequence with at least 70, 72, 75, 80, 85, 90, 91, 92, 93, 94, 95, 96, 97, 98, 99 or 100% identity to a sequence of SEQ ID NO: 6, which is a sequence of Savinase, P29600.

The target protease may be a protease from *Bacillus licheniformis* (UniProt accession number is: Q6PNN5. The target protease may comprise, consist essentially of, or consist of a sequence with at least 70, 72, 75, 80, 85, 90, 91, 92, 93, 94, 95, 96, 97, 98, 99 or 100% identity to a sequence of SEQ ID NO: 8, which is a sequence *B. licheniformis* protease, Q6PNN5.

The target protease may be an acid protease. Acid proteases are widely used in cheese making, food and feed preparation and in the leather industry. The acid protease may be a bacterial protease, a fungal protease or a mammalian protease. The acid protease may be an aspartic proteinase aspergillopepsin A (pepA) from *Aspergillus flavus* (UniProt accession number is: B8NLY9 (PEPA_ASPFN)). The target protease may comprise, consist essentially of, or consist of a sequence with at least 70, 72, 75, 80, 85, 90, 91, 92, 93, 94, 95, 96, 97, 98, 99 or 100% identity to a sequence of SEQ ID NO: 9, which is a sequence of an aspartic proteinase aspergillopepsin A (pepA) from *Aspergillus flavus*, B8NLY9 (PEPA_ASPFN).

The intein may be any intein. The intein may be an intein naturally capable of trans-splicing. The intein may be a cis-splicing intein engineered for trans-splicing. Methods of engineering cis-splicing inteins into artificial trans-splicing inteins and testing artificially split inteins for restoration of protease activity are described in Examples 17 and 18 herein. Inteins are polypeptides that have the ability to cleave themselves from proteins post-translationally and may mediate ligation of the remaining protein fragments (the exteins), and may have the ability to cleave DNA at specific sites for their propagations. The intein may be modified. Modified inteins may have the ability to cleave themselves but may lose their ability to cleave the DNA. The intein may be but is not limited to mTth, Pho_RadA, Tko_RadA, Sce_VMA, mVMA, and Pab_Lon. The intein may be one found in InBase, the intein database Perler et al.

1992 Proc Natl Acad Sci USA 89: 5577), which is incorporated by reference herein as if fully set forth.

The intein may be one of APMVPol (*Acanthomoeba polyphaga* Mimivirus), AbrPRP8 (*Aspergillus brevipes* FRR2439), Aca-JER2004PRP8 (*Ajellomyces capsulatus*), Aca-H143PRP8 (*Ajellomyces capsulatus* H143), Ade-ER3PRP8 (*Ajellomyces dermatitidis* ER-3), Aca-NAm1PRP8 (*Ajellomyces capsulatus* NAm1), Afu-Af293PRP8 (*Aspergillus fumigatus* var. *ellipticus* strain Af293), Ade-SLH14081PRP8 (*Ajellomyces dermatitidis* SLH14081), Afu-FRR0163PRP8 (*Aspergillus fumigatus* strain FRR0163), Afu-NRRL5109PRP8 (*Aspergillus fumigatus* var. *ellipticus* strain NRRL 5109), Ani-FGSCA4PRP8 (*Aspergillus nidulans* FGSC A), Agi-NRRL6136PRP8 (*Aspergillus giganteus* Strain NRRL 6136), AviPRP8 (*Aspergillus viridinutans* strain FRR0577), BciPRP8 (*Botrytis cinerea*), Bde-JEL423PRP8-1 (*Batrachochytrium dendrobatidis* JEL423), Bde-JEL197RPB2 (*Batrachochytrium dendrobatidis* JEL197), Bde-JEL423eIF-5B (*Batrachochytrium dendrobatidis* JEL423), Bde-JEL423PRP8-2 (*Batrachochytrium dendrobatidis* JEL423), Bfu-B05PRP8 (*Botryotinia fuckeliana* B05.10), Bde-JEL423RPC2 (*Batrachochytrium dendrobatidis* JEL423), CIVRIR1 (*Chilo iridescent virus*), CV-NY2AORF212392 (*Chlorella* virus NY2A), CV-NY2ARIR1 (*Chlorella* virus NY2A), CZIVRIR1 (*Costelytra zealandica* iridescent virus), Cba-WM02.98PRP8 (*Cryptococcus bacillisporus* strain WM02.98), Cba-WM728PRP8 (*Cryptococcus bacillisporus* strain WM728), CeuClpP (*Chlamydomonas eugametos*), CgaPRP8 (*Cryptococcus gattii*), ClaPRP8 (*Cryptococcus laurentii* strain CBS139), CmoClpP (*Chlamydomonas moewusii* strain UTEX 97), CmoRPB2 (*Chlamydomonas moewusii* strain UTEX 97), CglVMA (*Candida glabrata*), CpaThrRS (*Candida parapsilosis* strain CLIB214), Fne-APRP8 (*Filobasidiella neoformans* Serotype A), Cne-JEC21PRP8 (*Cryptococcus neoformans* JEC21), Fne-ADPRP8 (*Cryptococcus neoformans* Serotype AD), CreRPB2 (*Chlamydomonas reinhardtii*), CroVRPB2 (*Cafeteria roenbergensis* virus BV-PW1), CroVRIR1 (*Cafeteria roenbergensis* virus BV-PW1), CroVPol (*Cafeteria roenbergensis* virus BV-PW1), CroVTop2 (*Cafeteria roenbergensis* virus BV-PW1), CtrThrRS (*Candida tropicalis* ATCC750), CstRPB2 (*Coelomomyces stegomyiae*), CtrVMA (*Candida tropicalis*), DdiRPC2 (*Dictyostelium discoideum* strain AX4), DhanVMA (*Debaryomyces hansenii* CBS767), Ctr-MYA3404VMA (*Candida tropicalis* MYA-3404), DhanGLT1 (*Debaryomyces hansenii* CBS767), FteRPB2 (*Floydiella terrestris* strain UTEX 1709), GthDnaB (*Guillardia theta*), EniPRP8 (*Emericella nidulans* R20), Eni-FCSGA4PRP8 (*Emericella nidulans* FGSC A4), HaV01Pol (*Heterosigma akashiwo* virus 01), HcaPRP8 (*Histoplasma capsulatum*), IIV6RIR1 (Invertebrate iridescent virus 6), Kex-CBS379VMA (*Kazachstania exigua* strain CBS379), Kla-CBS683VMA (*Kluyveromyces lactis* CBS683), Kla-IFO1267VMA (*Kluyveromyces lactis* IFO1267), Kla-NRRLY1140VMA (*Kluyveromyces lactis* NRRL Y-1140), LelVMA (*Lodderomyces elongisporus*), NauPRP8 (*Neosartorya aurata* NRRL 4378), Mca-CBS113480PRP8 (*Microsporum canis* CBS 113480), NfiPRP8 (*Neosartorya fischeri*), Nfe-NRRL5534PRP8 (*Neosartorya fennelliae* NRRL 5534), Ngl-FRR1833PRP8 (*Neosartorya glabra* FRR1833), Ngl-FR2163PRP8 (*Neosartorya glabra* FRR2163), NquPRP8 (*Neosartorya quadricincta* strain NRRL 4175), NspiPRP8 (*Neosartorya spinosa* FRR4595), Pabr-Pb01PRP8 (*Paracoccidioides brasiliensis* Pb01), Pabr-Pb03PRP8 (*Paracoccidioides brasiliensis* Pb03), PanGLT1 (*Podospora anserina*), PanCHS2 (*Podospora anserina*), PchPRP8 (*Penicillium chrysogenum*), PblPRP8-a (*Phycomyces blakesleeanus*), Pbr-Pb18PRP8 (*Paracoccidioides brasiliensis* Pb18), PblPRP8-b (*Phycomyces blakesleeanus*), PexPRP8 (*Penicillium expansum*), PguGLT1 (*Pichia guilliermondii*), PnoGLT1 (*Phaeosphaeria nodorum* SN15), Pgu-altGLT1 (*Pichia guilliermondii*), PstVMA (*Pichia stipitis* CBS 6054), PnoRPA2 (*Phaeosphaeria nodorum* SN15), PpuDnaB (*Porphyra purpurea*), Ptr-PRP8 (*Pyrenophora tritici-repentis* Pt-1C-BF), PvuPRP8 (*Penicillium vulpinum*), PyeDnaB (*Porphyra yezoensis*), Sca-CBS4309VMA (*Saccharomyces castellii* strain CBS4309), SasRPB2 (*Spiromyces aspiralis* NRRL 22631), SceVMA, VMA (*Saccharomyces cerevisiae*), Sca-IFO1992VMA (*Saccharomyces castellii* strain IFO1992), Sce-DH1-1AVMA (*Saccharomyces cerevisiae* strain DH1-1A), ScarVMA (*Saccharomyces cariocanus* strain UFRJ 50791), Sce-Jay291VMA (*Saccharomyces cerevisiae* JAY291), Sce-YJM789VMA (*Saccharomyces cerevisiae* strain YJM789), Sce-OUT7091VMA (*Saccharomyces cerevisiae* OUT7091), Sce-OUT7112VMA (*Saccharomyces cerevisiae* OUT7112), SjaVMA (*Schizosaccharomyces japonicus* yFS275), Sex-IFO1128VMA (*Saccharomyces exiguus* strain IFO1128), SheRPB2 (*Stigeoclonium helveticum* strain UTEX 441), SdaVMA (*Saccharomyces dairenensis* strain CBS 421), SpaVMA (*Saccharomyces pastorianus* IFO11023), SpuPRP8 (*Spizellomyces punctatus*), SunVMA (*Saccharomyces unisporus* strain CBS 398), TglVMA (*Torulaspora globosa* strain CBS 764), TprVMA (*Torulaspora pretoriensis* strain CBS 5080), Ure-1704PRP8 (*Uncinocarpus reesii*), VpoVMA (*Vanderwaltozyma polyspora* strain CBS 2163), WIVRIR1 (*Wiseana* iridescent virus), ZroVMA (*Zygosaccharomyces rouxii* strain CBS 688), ZbiVMA (*Zygosaccharomyces bisporus* strain CBS 702), ZbaVMA (*Zygosaccharomyces bailii* strain CBS 685), AP-APSE1dpol (*Acyrthosiphon pisum* secondary endosymbiot phage 1), AP-APSE2dpol (Bacteriophage APSE-2), AP-APSE4dpol (*Candidatus Hamiltonella* defensa strain 5ATac bacteriophage), AP-APSE5dpol (Bacteriophage APSE-5), AP-Aaphi23MupF (Bacteriophage Aaphi23), AaeRIR2 (*Aquifex aeolicus* strain VF5), Aave-AAC001RIR1 (*Acidovorax avenae* subsp. *citrulli* AAC00-1), Aave-AAC001Aave1721 (*Acidovorax avenae* subsp. *citrulli* AAC00-1), Aave-ATCC19860RIR1 (*Acidovorax avenae* subsp. *avenae* ATCC 19860), AbaHyp-02185 (*Acinetobacter baumannii* ACICU), AceRIR1 (*Acidothermus cellulolyticus* 11B), AehDnaB-1 (*Alkalilimnicola ehrlichei* MLHE-1), AehDnaB-2 (*Alkalilimnicola ehrlichei* MLHE-1), AehRir1 (*Alkalilimnicola ehrlichei* MLHE-1), MupFMupF (Aggregatibacter phage S1249), AhaDnaE-c (*Aphanothece halophytica*), AhaDnaE-n (*Aphanothece halophytica*), Alvi-DSM180GyrA (*Allochromatium vinosum* DSM 180), AmaMADE823 (*Alteromonas macleodii*), Amax-CS328DnaX (*Arthrospira maxima* CS-328), AovDnaE-c (*Aphanizomenon ovalisporum*), AovDnaE-n (*Aphanizomenon ovalisporum*), Apl-C1DnaX (*Arthrospira platensis*), AspDnaE-c (*Anabaena* species PCC7120), Arsp-FB24DnaB (*Arthrobacter* species FB24), AspDnaE-n (*Anabaena* species PCC7120), AvaDnaE-c (*Anabaena variabilis* ATCC29413), AvinRIR1BIL (*Azotobacter vinelandii*), AvaDnaE-n (*Anabaena variabilis* ATCC29413), Bce-MCO3DnaB (*Burkholderia cenocepacia* MCO-3), Bce-PC184DnaB (*Burkholderia cenocepacia* PC184), Bse-MLS10TerA (*Bacillus selenitireducens* MLS10), BsuP-M1918RIR1 (*B. subtilis* M1918 prophage), BsuP-SPBc2RIR1 (*B. subtilis* strain 168 Sp beta c2 prophage), Bcep 1808_7358 (*Burkholderia vietnamiensis* G4), CP-P1201Thy1 (*Corynebacterium* phage P1201), CagRIR1 (*Chlorochromatium aggregatum*), CauSpoVR (*Chloroflexus aurantiacus* J-10-fl), CbP-C-StRNR (*Clostridium botulinum* phage C-St), CbP-D1873RNR (*Clostridium botulinum* phage D), Cbu-DugwayDnaB (*Coxiella burnetii* Dugway 5J108-111), Cbu-GoatDnaB (*Coxiella burnetii* MSU Goat Q177), Cbu-RSA334DnaB (*Coxiella burnetii* RSA 334), Cbu-RSA493DnaB (*Coxiella burnetii* RSA 493), CceHyp1-Csp-2 (*Cyanothece* sp. ATCC 51142), CchRIR1 (*Chlorobium chlorochromatii* CaD3), CcyHyp1-Csp-1 (*Cyanothece* sp. CCY0110), CcyHyp1-Csp-2 (*Cyanothece* sp. CCY0110), Cfl-DSM20109DnaB (*Cellulomonas flavigena* DSM 20109), ChyRIR1 (*Carboxydothermus hydrogenoformans* Z-2901), CklPTerm (*Clostridium kluyveri* DSM 555), Cra-CS505DnaE-c (*Cylindrospermopsis raciborskii* CS-505), Cra-CS505DnaE-n (*Cylindrospermopsis raciborskii* CS-505), Cra-CS505GyrB (*Cylindrospermopsis raciborskii* CS-505), Csp-CCY0110DnaE-c (*Cyanothece* sp. CCY0110), Csp-CCY0110DnaE-n (*Cyanothece* sp. CCY0110), Csp-PCC7424DnaE-c (*Cyanothece* sp. PCC 7424), Csp-PCC7424DnaE-n (*Cyanothece* sp. PCC 7424), Csp-PCC7425DnaB (*Cyanothece* sp. PCC 7425), Csp-PCC7822DnaE-n (*Cyanothece* sp. PCC 7822), Csp-PCC8801DnaE-c (*Cyanothece* sp. PCC 8801), Csp-PCC8801DnaE-n (*Cyanothece* sp. PCC 8801), CthATPaseBIL (*Clostridium thermocellum*), Cth-ATCC27405TerA (*Clostridium thermocellum* ATCC27405), Cth-DSM2360TerA (*Clostridium thermocellum* DSM 2360), CwaDnaB (*Crocosphaera watsonii* WH 8501), CwaDnaE-c (*Crocosphaera watsonii* WH 8501), CwaDnaE-n (*Crocosphaera watsonii* WH 8501), CwaPEP (*Crocosphaera watsonii* WH 8501), CwaRIR1 (*Crocosphaera watsonii* WH 8501), DaudRIR1 (*Candidatus Desulforudis audaxviator* MP104C), DgeDnaB (*Deinococcus geothermalis* DSM11300), Dha-DCB2RIR1 (*Desulfitobacterium hafniense* DCB-2), Dha-Y51RIR1 (*Desulfitobacterium hafniense* Y51), Dpr-MLMS1RIR1 (delta proteobacterium MLMS-1), DraRIR1 (*Deinococcus radiodurans* R1 TIGR strain), DraSnf2-c (*Deinococcus radiodurans* R1 TIGR strain), Snf2-nN-TERM (*Deinococcus radiodurans* R1 TIGR strain), Dra-ATCC13939Snf2 (*Deinococcus radiodurans* R1 ATCC13939 Brooks & Murray strain), UDPGD (*Dictyoglomus thermophilum* H-6-12), DvulParB (*Desulfovibrio vulgaris* subsp. *vulgaris* DP4), EP-Min27Primase (Enterobacteria phage Min27), FalDnaB (*Frankia alni* ACN14a), Fsp-CcI3RIR1 (*Frankia* species CcI3), GobDnaE (*Gemmata obscuriglobus* UQM2246), GobHyp (*Gemmata obscuriglobus* UQM2246), GviDnaB (*Gloeobacter violaceus* PCC 7421), GviRIR1-2 (*Gloeobacter violaceus* PCC 7421), GviRIR1-1 (*Gloeobacter violaceus* PCC 7421), HhalDnaB (*Halorhodospira halophila* SL1), Kfl-DSM17836DnaB (*Kribbella flavida* DSM 17836), KraDnaB (*Kineococcus radiotolerans* SRS30216), LLP-KSY1PolA (*Lactococcus* phage KSY1), LP-phiHSIChelicase (*Listonella pelagia* phage phiHSIC), Lsp-PCC8106GyrB (*Lyngbya* sp. PCC 8106), MP-BeDnaB (Mycobacteriophage Bethlehem), MP-Begp51 (Mycobacteriophage Bethlehem), MP-Cateragp206 (Mycobacteriophage Catera), MP-KBGgp53 (*Mycobacterium* phage KBG), MP-OmegaDnaB (Mycobacteriophage Omega), MP-Mcjw1DnaB (Mycobacteriophage CJW1), gp50 (Mycobacteriophage U2), Maer-NIES843DnaB (*Microcystis aeruginosa* NIES-843), Maer-NIES843DnaE-c (*Microcystis aeruginosa* NIES-843), Maer-NIES843DnaE-n (*Microcystis aeruginosa* NIES-843), Mau-ATCC27029GyrA (*Micromonospora aurantiaca* ATCC 27029), Mav-104DnaB (*Mycobacterium avium* 104), Mav-ATCC25291DnaB (*Mycobacterium avium* subsp. *avium* ATCC 25291), Mav-ATCC35712DnaB (*Mycobacterium avium*), Mav-PTDnaB (*Mycobacterium avium* subsp. *paratuberculosis* str. k10), MboPps1 (*Mycobacterium bovis* subsp. *bovis* AF2122/97), MboRecA (*Mycobacterium bovis* subsp. *bovis* AF2122/97), MboPps1 (*Mycobacterium bovis* subsp. *bovis* AF2122/97), Mbo-AF2122DnaB (*Mycobacterium bovis* subsp. *bovis* AF2122/97), Mbo-1173PDnaB (*Mycobacterium bovis* BCG Pasteur 1173P), McaMupF (*Methylococcus capsulatus* Bath prophage MuMc02), McaRIR1 (*Methylococcus capsulatus* Bath), MchRecA (*Mycobacterium chitae*), Mcht-PCC7420DnaE-1 (*Microcoleus chthonoplastes* PCC7420), Mcht-PCC7420DnaE-2c (*Microcoleus chthonoplastes* PCC7420), Mcht-PCC7420DnaE-2n (*Microcoleus chthonoplastes* PCC7420), Mcht-PCC7420GyrB (*Microcoleus chthonoplastes* PCC7420), Mcht-PCC7420RIR1-1 (*Microcoleus chthonoplastes* PCC7420), Mcht-PCC7420RIR1-2 (*Microcoleus chthonoplastes* PCC7420), Mexhelicase (*Methylobacterium extorquens* AM1), MexTrbC (*Methylobacterium extorquens* AM1), MfaRecA (*Mycobacterium fallax*), MflGyrA (*Mycobacterium flavescens* Fla0), MflRecA (*Mycobacterium flavescens* Fla0), Mfl-ATCC14474RecA (*Mycobacterium flavescens* ATCC 14474), Mfl-PYR-GCKDnaB (*Mycobacterium flavescens* PYR-GCK), MgaGyrA (*Mycobacterium gastri*), MgaRecA (*Mycobacterium gastri*), MgaPps1 (*Mycobacterium gastri*), Mgi-PYR-GCKDnaB (*Mycobacterium gilvum* PYR-GCK), Mgi-PYR-GCKGyrA (*Mycobacterium gilvum* PYR-GCK), MgoGyrA (*Mycobacterium gordonae*), Min-1442DnaB (*Mycobacterium intracellulare*), Min-ATCC13950GyrA (*Mycobacterium intracellulare* ATCC 13950), MkasGyrA (*Mycobacterium kansasii*), Mkas-ATCC12478GyrA (*Mycobacterium kansasii* ATCC 12478), Mle-Br4923GyrA (*Mycobacterium leprae* Br4923), Mle-TNDnaB (*Mycobacterium leprae* strain TN), Mle-TNGyrA (*Mycobacterium leprae* TN), MlePps1 (*Mycobacterium leprae*), Mle-TNRecA (*Mycobacterium leprae* strain TN), MmaGyrA (*Mycobacterium malmoense*), MmagMagn8951BIL (*Magnetospirillum magnetotacticum* MS-1), MshRecA (*Mycobacterium shimodei*), MsmDnaB-1 (*Mycobacterium smegmatis* MC2 155), MsmDnaB-2 (*Mycobacterium smegmatis* MC2 155), Msp-KMSDnaB (*Mycobacterium* species KMS), Msp_KMSGyrA (*Mycobacterium* species KMS), Msp-MCSDnaB (*Mycobacterium* species MCS), Msp_MCSGyrA (*Mycobacterium* species MCS), MtheRecA (*Mycobacterium thermoresistibile*), MtuPps1 (*Mycobacterium tuberculosis* strain H37Rv), Mtu-CDC1551DnaB (*Mycobacterium tuberculosis* CDC1551), Mtu-CRecA (*Mycobacterium tuberculosis* C), Mtu-CPHL-RecA (*Mycobacterium tuberculosis* CPHL_A), Mtu-EAS054RecA (*Mycobacterium tuberculosis* EAS054), Mtu-CanettiRecA (*Mycobacterium tuberculosis* strain Canetti), Mtu-F11DnaB (*Mycobacterium tuberculosis* strain F11), Mtu-H37RaDnaB (*Mycobacterium tuberculosis* H37Ra), Mtu-H37RvDnaB (*Mycobacterium tuberculosis* H37Rv), Mtu-H37RvRecA (*Mycobacterium tuberculosis* H37Rv, Also CDC1551), Mtu-HaarlemDnaB (*Mycobacterium tuberculosis* str. Haarlem), Mtu-R604RecA-n (*Mycobacterium tuberculosis* 98-R604 INH-RIF-EM), Mtu-K85RecA (*Mycobacterium tuberculosis* K85), Mtu-So93RecA (*Mycobacterium tuberculosis* So93/sub_species Canetti), Mtu-T17RecA-c (*Mycobacterium tuberculosis* T17), Mtu-T17RecA-n (*Mycobacterium tuberculosis* T17), Mtu-T46RecA (*Mycobacterium tuberculosis* T46), Mtu-T85RecA (*Mycobacterium tuberculosis* T85), MvanDnaB (*Mycobacterium vanbaalenii* PYR-1), Mtu-T92RecA (*Mycobacterium tuberculosis* T92), MvanGyrA (*Mycobacterium vanbaalenii* PYR-1), MxaRAD25 (*Myxococcus xan-* thus DK1622), MxeGyrA (*Mycobacterium xenopi* strain IMM5024), Naz-0708RIR1-2 (*Nostoc azollae* 0708), Naz-0708RIR1-1 (*Nostoc azollae* 0708), NfaDnaB (*Nocardia farcinica* IFM 10152), NfaNfa15250 (*Nocardia farcinica* IFM 10152), NfaRIR1 (*Nocardia farcinica* IFM 10152), Nosp-CCY9414DnaE-n (*Nodularia spumigena* CCY9414), NpuDnaB (*Nostoc punctiforme*), NpuGyrB (*Nostoc punctiforme*), Npu-PCC73102DnaE-c (*Nostoc punctiforme* PCC73102), Npu-PCC73102DnaE-n (*Nostoc punctiforme* PCC 73102), Nsp-JS614DnaB (*Nocardioides* species JS614), Nsp-JS614TOPRIM (*Nocardioides* species JS614), Nsp-PCC7120DnaB (*Nostoc* species PCC7120), Nsp-PCC7120DnaE-c (*Nostoc* species PCC7120), Nsp-PCC7120DnaE-n (*Nostoc* species PCC7120), Nsp-PCC7120RIR1 (*Nostoc* species PCC7120), OliDnaE-c (*Oscillatoria limnetica* str. Solar Lake), OliDnaE-n (*Oscillatoria limnetica* str. Solar Lake), PP-PhiELHelicase (*Pseudomonas aeruginosa* phage phiEL), PP-PhiELORF11 (*Pseudomonas aeruginosa* phage phiEL), PP-PhiELORF40 (*Pseudomonas aeruginosa* phage phiEL), PP-PhiELORF39 (*Pseudomonas aeruginosa* phage phiEL), PflFhaBIL (*Pseudomonas fluorescens* Pf-5), Pma-ExH1DnaE (*Persephonella marina* EX-H1), PlutRIR1 (*Pelodictyon luteolum* DSM 273), Pma-EXH1GyrA (*Persephonella marina* EX-H1), PnaRIR1 (*Polaromonas naphthalenivorans* CJ2), Posp-JS666DnaB (*Polaromonas* species JS666), PuncDnaB (*Polynucleobacter* sp. QLW-P1DMWA-1), Posp-JS666RIR1 (*Polaromonas* species JS666), Pssp-A1-1Fha (*Pseudomonas* species A1-1), PsyFha (*Pseudomonas syringae* pv. tomato str. DC3000), Rbr-D9GyrB (*Raphidiopsis brookii* D9), RceRIR1 (*Rhodospirillum centenum* SW), Rer-SKI21DnaB (*Rhodococcus erythropolis* SK121), RmaDnaB (*Rhodothermus marinus*), Rma-DSM4252DnaE (*Rhodothermus marinus* DSM 4252), Rma-DSM4252DnaB (*Rhodothermus marinus* DSM 4252), RspRir1 (*Roseovarius* species 217), SaP-SETP12dpol (*Salmonella* phage SETP12), SaP-SETP3Helicase (*Salmonella* phage SETP3), SaP-SETP3dpol (*Salmonella* phage SETP3), SaP-SETP5dpol (*Salmonella* phage SETP5), SareDnaB (*Salinispora arenicola* CNS-205), ReGHelicase (*Streptomyces avermitilis* MA-4680), Sel-PC6301RIR1 (*Synechococcus elongatus* PCC 6301), Sel-PC7942DnaE-c (*Synechococcus elongatus* PC7942), Sel-PC7942RIR1 (*Synechococcus elongatus* PC7942), Sel-PC7942DnaE-n (*Synechococcus elongatus* PC7942), Sel-PCC6301DnaE-n (*Synechococcus elongatus* PCC 6301), Sel-PCC6301DnaE-c (*Synechococcus elongatus* PCC 6301 and PCC7942), ShP-Sfv-2a-2457T-nPrimase (*Shigella flexneri* 2a str. 2457T), SepRIR1 (*Staphylococcus epidermidis* RP62A), ShP-Sfv-2a-301Primase (*Shigella flexneri* 2a str. 301), ShP-Sfv-5Primase (*Shigella flexneri* 5 str. 8401), SoP-SO1dpol (*Sodalis* phage SO-1), SruDnaB (*Salinibacter ruber* DSM 13855), SplDnaX (*Spirulina platensis* strain C1), SruPolBc (*Salinibacter ruber* DSM 13855), SruRIR1 (*Salinibacter ruber* DSM 13855), SspDnaB (*Synechocystis* species strain PCC6803), SspDnaE-n, DnaE-N (*Synechocystis* species strain PCC6803), SspDnaE-c, DnaE-C (*Synechocystis* species strain PCC6803), SspDnaX (*Synechocystis* species strain PCC6803), Ssp-JA2RIR1 (*Synechococcus* species JA-2-3B a 2-13), Ssp-JA2DnaB (*Synechococcus* species JA-2-3B a 2-13), SspGyrB (*Synechocystis* species strain PCC6803), Ssp-JA3DnaB (*Synechococcus* species JA-3-3Ab), Ssp-JA3RIR1 (*Synechococcus* species JA-3-3Ab), Ssp-PCC7002DnaE-c (*Synechocystis* species strain PCC 7002), Ssp-PCC7002DnaE-n (*Synechocystis* species strain PCC 7002), Ssp-PCC7335RIR1 (*Synechococcus* sp. PCC 7335), StP-TwortORF6 (*Staphylococcus* phage Twort), Susp-NBC371DnaB (*Sulfurovum* sp. NBC37-1), Taq-Y51MC23DnaE (*Thermus aquaticus* Y51MC23), TelDnaE-c (*Thermosynechococcus elongatus* BP-1), Tcu-DSM43183RecA (*Thermomonospora curvata* DSM 43183), TelDnaE-n (*Thermosynechococcus elongatus* BP-1), Taq-Y51MC23RIR1 (*Thermus aquaticus* Y51MC23), TerDnaB-1 (*Trichodesmium erythraeum* IMS101), TerDnaB-2 (*Trichodesmium erythraeum* IMS101), TerDnaE-2 (*Trichodesmium erythraeum* IMS101), TerDnaE-1 (*Trichodesmium erythraeum* IMS101), TerDnaE-3c (*Trichodesmium erythraeum* IMS101), TerDnaE-3n (*Trichodesmium erythraeum* IMS101), TerGyrB (*Trichodesmium erythraeum* IMS101), TerNdse-1 (*Trichodesmium erythraeum* IMS101), TerNdse-2 (*Trichodesmium erythraeum* IMS101), TerRIR-1 (*Trichodesmium erythraeum* IMS101), TerRIR-2 (*Trichodesmium erythraeum* IMS101), TerRIR-3 (*Trichodesmium erythraeum* IMS101), TerRIR-4 (*Trichodesmium erythraeum* IMS101), TerSnf2 (*Trichodesmium erythraeum* IMS101), TerThyX (*Trichodesmium erythraeum* IMS101), TfusRecA-1 (*Thermobifida fusca* YX), TfusRecA-2 (*Thermobifida fusca* YX), TfusTfu2914 (*Thermobifida fusca* YX), Thsp-K90RIR1 (*Thioalkalivibrio* sp. K90mix), Tth-DSM571RIR1 (*Thermoanaerobacterium thermosaccharolyticum* DSM 571), Tth-HB27DnaE-1, Tth (*Thermus thermophilus* HB27), Tth-HB27DnaE-2 (*Thermus thermophilus* HB27), Tth-HB27RIR1-1 (*Thermus thermophilus* HB27), Tth-HB27RIR1-2 (*Thermus thermophilus* HB27), Tth-HB8DnaE-1 (*Thermus thermophilus* HB8), Tth-HB8DnaE-2 (*Thermus thermophilus* HB8), Tth-HB8RIR1-1 (*Thermus thermophilus* HB8), Tth-HB8RIR1-2 (*Thermus thermophilus* HB8), TvuDnaE-c (*Thermosynechococcus vulcanus*), TvuDnaE-n (*Thermosynechococcus vulcanus*), TyeRNR-1 (*Thermodesulfovibrio yellowstonii* DSM 11347), TyeRNR-2 (*Thermodesulfovibrio yellowstonii* DSM 11347), ApeAPE0745 (*Aeropyrum pernix* KI), Cme-booPol-II (*Candidatus Methanoregula boonei* 6A8), Fac-Fer1RIR1 (*Ferroplasma acidarmanus* taxon:97393), FacPps1 (*Ferroplasma acidarmanus*), Fac-TypeIRIR1 (*Ferroplasma acidarmanus* type I), FacPps1 (*Ferroplasma acidarmanus*), HmaCDC21 (*Haloarcula marismortui* ATCC 43049), HmaPol-II (*Haloarcula marismortui* ATCC 43049), HmaPolB (*Haloarcula marismortui* ATCC 43049), HmaTopA (*Haloarcula marismortui* ATCC 43049), Hmu-DSM12286MCM (*Halomicrobium mukohataei* DSM 12286), Hmu-DSM12286PolB (*Halomicrobium mukohataei* DSM 12286), Hsa-R1MCM (*Halobacterium salinarum* R-1), Hsp-NRCICDC21 (*Halobacterium* species NRC-1), Hsp-NRC1Pol-II (*Halobacterium salinarum* NRC-1), HutMCM-2 (*Halorhabdus utahensis* DSM 12940), HutMCM-1 (*Halorhabdus utahensis* DSM 12940), HwaGyrB (*Haloquadratum walsbyi* DSM 16790), HvoPolB (*Haloferax volcanii* DS70), HwaMCM-1 (*Haloquadratum walsbyi* DSM 16790), HwaMCM-2 (*Haloquadratum walsbyi* DSM 16790), HwaMCM-3 (*Haloquadratum walsbyi* DSM 16790), HwaMCM-4 (*Haloquadratum walsbyi* DSM 16790), HwaPol-II-1 (*Haloquadratum walsbyi* DSM 16790), HwaPol-II-2 (*Haloquadratum walsbyi* DSM 16790), HwaPolB-1 (*Haloquadratum walsbyi* DSM 16790), HwaPolB-2 (*Haloquadratum walsbyi* DSM 16790), HwaPolB-3 (*Haloquadratum walsbyi* DSM 16790), HwaRCF (*Haloquadratum walsbyi* DSM 16790), HwaRIR1-1 (*Haloquadratum walsbyi* DSM 16790), HwaRIR1-2 (*Haloquadratum walsbyi* DSM 16790), HwaTop6B (*Haloquadratum walsbyi* DSM 16790), rPolA" (*Haloquadratum walsbyi* DSM 16790), MaeoPol-II (*Methanococcus aeolicus* Nankai-3), MaeoRFC (*Methanococcus aeolicus* Nankai-3), MaeoRNR (*Methanococcus aeolicus*

Nankai-3), Maeo-N3Helicase (*Methanococcus aeolicus* Nankai-3), UDPGD (*Methanococcus aeolicus* Nankai-3), Maeo-N3RtcB (*Methanococcus aeolicus* Nankai-3), Mein-MEPEP (*Methanocaldococcus infernus* ME), Mein-MERFC (*Methanocaldococcus infernus* ME), MemarMCM2 (*Methanoculleus marisnigri* JR1), Memar-Pol-II (*Methanoculleus marisnigri* JR1), Mesp-FS406PolB-1 (*Methanocaldococcus* sp. FS406-22), Mesp-FS406PolB-2 (*Methanocaldococcus* sp. FS406-22), Mesp-FS406PolB-3 (*Methanocaldococcus* sp. FS406-22), Msp-FS406-22LHR (*Methanocaldococcus* sp. FS406-22), Mfe-AG86Pol-1 (*Methanocaldococcus fervens* AG86), Mfe-AG86Pol-2 (*Methanocaldococcus fervens* AG86), MhuPol-II (*Methanospirillum hungateii* JF-1), MjaGF-6P (*Methanococcus jannaschii*), MjaHelicase (*Methanococcus jannaschii*), MjaHyp-1 (*Methanococcus jannaschii*), MjaIF2 (*Methanococcus jannaschii*), MjaKlba (*Methanococcus jannaschii*), MjaPEP (*Methanococcus jannaschii*), MjaPol-1 (*Methanococcus jannaschii*), MjaPol-2 (*Methanococcus jannaschii*), MjaRFC-1 (*Methanococcus jannaschii*), MjaRFC-2 (*Methanococcus jannaschii*), MjaRFC-3 (*Methanococcus jannaschii*), MjaRNR-1 (*Methanococcus jannaschii*), MjaRNR-2 (*Methanococcus jannaschii*), Mja-Hyp-2 (*Methanococcus jannaschii*), MjaTFIIB (*Methanococcus jannaschii*), UDPGD (*Methanococcus jannaschii*), Mjar-Gyr (*Methanococcus jannaschii*), rPolA' (*Methanococcus jannaschii*), Mja rPol A' (*Methanococcus jannaschii*), MkaCDC48 (*Methanopyrus kandleri* AV19), MkaEF2 (*Methanopyrus kandleri* AV19), MkaRFC (*Methanopyrus kandleri* AV19), MkaRtcB (*Methanopyrus kandleri* AV19), MkaVatB (*Methanopyrus kandleri* AV19), MthRIR1 (*Methanothermobacter thermautotrophicus*), Mvu-M7Helicase (*Methanocaldococcus vulcanius* M7), Mvu-M7Pol-1 (*Methanocaldococcus vulcanius* M7), Mvu-M7Pol-2 (*Methanocaldococcus vulcanius* M7), Mvu-M7Pol-3 (*Methanocaldococcus vulcanius* M7), UDPGD (*Methanocaldococcus vulcanius* M7), NeqPol-c (*Nanoarchaeum equitans* Kin4-M), NeqPol-n (*Nanoarchaeum equitans* Kin4-M), Nma-ATCC43099MCM (*Natrialba magadii* ATCC 43099), Nma-ATCC43099PolB-1 (*Natrialba magadii* ATCC 43099), Nma-ATCC43099PolB-2 (*Natrialba magadii* ATCC 43099), NphCDC21 (*Natronomonas pharaonis* DSM 2160), NphPolB-2 (*Natronomonas pharaonis* DSM 2160), NphPolB-1 (*Natronomonas pharaonis* DSM 2160), rPolA" (*Natronomonas pharaonis* DSM 2160), PabCDC21-1 (*Pyrococcus abyssi*), PabCDC21-2 (*Pyrococcus abyssi*), PabIF2 (*Pyrococcus abyssi*), PabKlbA (*Pyrococcus abyssi*), PabLon (*Pyrococcus abyssi*), PabMoaa (*Pyrococcus abyssi*), PabPol-II (*Pyrococcus abyssi*), PabRFC-1 (*Pyrococcus abyssi*), PabRFC-2 (*Pyrococcus abyssi*), PabRIR1-1 (*Pyrococcus abyssi*), PabRIR1-2 (*Pyrococcus abyssi*), PabRIR1-3 (*Pyrococcus abyssi*), PabHyp-2 (*Pyrococcus abyssi*), PabVMA (*Pyrococcus abyssi*), ParRIR1 (*Pyrobaculum arsenaticum* DSM 13514), PfuCDC21 (*Pyrococcus furiosus*), PfuIF2 (*Pyrococcus furiosus*), PfuKlbA (*Pyrococcus furiosus*), PfuLon (*Pyrococcus furiosus*), PfuRFC (*Pyrococcus furiosus*), PfuRIR1-1 (*Pyrococcus furiosus*), PfuRIR1-2 (*Pyrococcus furiosus*), PfuHyp-2 (*Pyrococcus furiosus*), PfuTopA (*Pyrococcus furiosus*), PfuVMA (*Pyrococcus furiosus*), PhoCDC21-1 (*Pyrococcus horikoshii* OT3), PhoCDC21-2 (*Pyrococcus horikoshii* OT3), PhoIF2 (*Pyrococcus horikoshii* OT3), PhoKlbA (*Pyrococcus horikoshii* OT3), PhoLHR (*Pyrococcus horikoshii* OT3), PhoLon (*Pyrococcus horikoshii* OT3), PoIl (*Pyrococcus horikoshii* OT3), PhoPol-II (*Pyrococcus horikoshii* OT3), PhoRFC (*Pyrococcus horikoshii* OT3), PhoRIR1 (*Pyrococcus horikoshii* OT3), PhoRadA (*Pyrococcus horikoshii* OT3), PhoVMA (*Pyrococcus horikoshii* OT3), PhoHyp-2 (*Pyrococcus horikoshii* OT3), Phor-Gyr (*Pyrococcus horikoshii* OT3), Psp-GBDPol (*Pyrococcus species* GB-D), Smar1471 (*Staphylothermus marinus* F1), PtoVMA (*Picrophilus torridus* DSM 9790), Tac-ATCC25905VMA (*Thermoplasma acidophilum* ATCC 25905), SmarMCM2 (*Staphylothermus marinus* F1), Tac-DSM1728VMA (*Thermoplasma acidophilum* DSM1728), Tsp-TYPol-1 (*Thermococcus aggregans*), Tsp-TYPol-2 (*Thermococcus aggregans*), Tsp-TYPol-3 (*Thermococcus aggregans*), TbaPol-II (*Thermococcus barophilus* MP), TfuPol-1 (*Thermococcus fumicolans*), ThyPol-1 (*Thermococcus hydrothermalis*), TfuPol-2 (*Thermococcus fumicolans*), ThyPol-2 (*Thermococcus hydrothermalis*), TkoCDC21-1 (*Thermococcus kodakaraensis* KOD1), TkoCDC21-2 (*Thermococcus kodakaraensis* KOD1), TkoHelicase (*Thermococcus kodakaraensis* KOD1), TkoIF2 (*Thermococcus kodakaraensis* KOD1), TkoKlbA (*Thermococcus kodakaraensis* KOD1), TkoLHR (*Thermococcus kodakaraensis* KOD1), Psp-KOD-Pol-1 (*Thermococcus kodakaraensis* KOD1), KODPol-2 (*Thermococcus kodakaraensis* KOD1), TkoPol-II (*Thermococcus kodakaraensis* KOD1), TkoRIR1-1 (*Thermococcus kodakaraensis* KOD1), TkoRFC (*Thermococcus kodakaraensis* KOD1), TkoRIR1-2 (*Thermococcus kodakaraensis* KOD1), TkoRadA (*Thermococcus kodakaraensis* KOD1), TkoTopA (*Thermococcus kodakaraensis* KOD1), Tkor-Gyr (*Thermococcus kodakaraensis* KOD1), TliPol-1 (*Thermococcus litoralis*), TliPol-2 (*Thermococcus litoralis*), TmaPol (*Thermococcus marinus*), Ton-NA1LHR (*Thermococcus onnurineus* NA1), Ton-NA1Pol (*Thermococcus onnurineus* NA1), TpePol (*Thermococcus peptonophilus* strain SM2), Tsi-MM739Lon (*Thermococcus sibiricus* MM739), Tsi-MM739Pol-1 (*Thermococcus sibiricus* MM739), Tsi-MM739Pol-2 (*Thermococcus sibiricus* MM 739), Tsi-MM739RFC (*Thermococcus sibiricus* MM 739), AM4RtcB (*Thermococcus* sp. AM4), Tsp-AM4LHR (*Thermococcus* sp. AM4), Tsp-AM4Lon (*Thermococcus* sp. AM4), Tsp-AM4RIR1 (*Thermococcus* sp. AM4), Tsp-GE8Pol-2 (*Thermococcus* species GE8), Tsp-GE8Pol-1 (*Thermococcus* species GE8), Tsp-GTPol-1 (*Thermococcus* species GT), Tsp-GTPol-2 (*Thermococcus* species GT), Tsp-OGL-P20Pol (*Thermococcus* sp. OGL-20P), TthiPol (*Thermococcus thioreducens*), TziPol (*Thermococcus zilligii*), TvoVMA (*Thermoplasma volcanium* GSS 1), Unc-ERSPFL (uncultured archaeon GZfos13E1), Unc-ERSRIR1 (uncultured archaeon GZfos9C4), Unc-MetRFSMCM2 (uncultured archaeon Rice Cluster I), or Unc-ERSRNR (uncultured archaeon GZfos10C7).

An intein name provides information about the organism and the protein name given to a homolog of the protein that hosts the intein in a well-studied organism. For example, in the name Ade-ER3PRP8, "Ade-ER3" refers to the organism *Ajellomyces dermatitidis* ER-3 and PRP8 is the protein name given to a homolog of the protein that hosts the intein in a well-studied organism.

The intein may have a sequence of one the inteins disclosed in any one of U.S. pre-grant patent application publication Nos. U.S. 2013-0007919 (published on Jan. 3, 2013 from U.S. application Ser. No. 13/508,156, filed Sep. 20, 2012), Nos. U.S. 2013-0036517 (published on Feb. 7, 2013 from U.S. application Ser. No. 13/508,234, filed Sep. 20, 2012), and U.S. 2013-0071884 (published on Mar. 21, 2013 from U.S. application Ser. No. 13/508,280, filed Sep. 20, 2012), all of which are incorporated by reference herein as if fully set forth.

The intein may be a trans-splicing intein. The trans-splicing intein may be gp41-1, Cbu_DnaB, Mja_GF-6P, Mja_Hyp-1, Mja_IF2, Mja_Pol-1, Pab_CDC21-1, Pab_IF2-N, Pab_VMA, Pho_IF2, Pho_VMA, Rma_DnaB, Sru_DnaB, Tag_Pol-1_Tsp-TY_Pol-1, Ter_RIR1-4, Tko_IF2, or Tth-HB27_DnaE-2 intein. The intein may be gp41-1 intein. The gp41-1 intein may comprise, consist essentially of, or consist of an amino acid sequence with at least 70, 72, 75, 80, 85, 90, 91, 92, 93, 94, 95, 96, 97, 98, 99, or 100% identity to SEQ ID NO: 11.

The trans-splicing intein may comprise two parts. One part of the trans-splicing intein may be the N-terminal intein, or N-intein ($I^N$). Another part of the trans-splicing intein may be the C-terminal intein, or C-intein ($I^C$). The trans-splicing intein may comprise a combination of N-intein and C-intein as set forth in Table I, below. The N-intein and C-intein sequences listed in the same row as one trans-splicing intein indicate the sequences of the N-intein and C-intein in the first precursor and second precursor, respectively. In each of the trans-splicing inteins of Table I, the N-intein comprise, consist essentially of, or consist of an amino acid sequence having at least 70, 72, 75, 80, 85, 90, 91, 92, 93, 94, 95, 96, 97, 98, 99, or 100% identity to the sequence identified on the same row as the respective intein in Table 1. Similarly, in each of the trans-splicing inteins of Table I, the C-intein may comprise, consist essentially of, or consist of an amino acid sequence having at least 70, 72, 75, 80, 85, 90, 91, 92, 93, 94, 95, 96, 97, 98, 99, or 100% identity to the sequence identified on the same row as the respective intein in Table 1. For example, in the trans-splicing intein listed as A, the N-intein may comprise at least 70, 72, 75, 80, 85, 90, 91, 92, 93, 94, 95, 96, 97, 98, 99, or 100% identity to SEQ ID NO: 14, and the C-intein may comprise at least 70, 72, 75, 80, 85, 90, 91, 92, 93, 94, 95, 96, 97, 98, 99, or 100% identity to SEQ ID NO: 15.

| Trans-Splicing Intein | N-intein | C-intein |
| --- | --- | --- |
| A | SEQ ID NO: 14 | SEQ ID NO: 15 |
| B | SEQ ID NO: 16 | SEQ ID NO: 17 |
| C | SEQ ID NO: 18 | SEQ ID NO: 19 |
| D | SEQ ID NO: 20 | SEQ ID NO: 21 |
| E | SEQ ID NO: 22 | SEQ ID NO: 23 |
| F | SEQ ID NO: 24 | SEQ ID NO: 25 |
| G | SEQ ID NO: 26 | SEQ ID NO: 27 |
| H | SEQ ID NO: 28 | SEQ ID NO: 29 |
| I | SEQ ID NO: 30 | SEQ ID NO: 31 |
| J | SEQ ID NO: 32 | SEQ ID NO: 33 |
| K | SEQ ID NO: 34 | SEQ ID NO: 35 |
| L | SEQ ID NO: 36 | SEQ ID NO: 37 |
| M | SEQ ID NO: 38 | SEQ ID NO: 39 |
| N | SEQ ID NO: 40 | SEQ ID NO: 41 |
| O | SEQ ID NO: 42 | SEQ ID NO: 43 |
| P | SEQ ID NO: 44 | SEQ ID NO: 45 |
| Q | SEQ ID NO: 46 | SEQ ID NO: 47 |

When each of the N-inteins and C-inteins in Table 1 are at 100% identity to the indicated sequence, the trans-splicing inteins are as follows: intein a is gp41-1, intein B is Cbu_DnaB, intein C is Mja_GF-6P, intein D is Mja_Hyp-1, intein E is Mja_IF2, intein F is Mja_Pol-1, intein G is Pab_CDC21-1, intein H is Pab_IF2-N, intein I is Pab_VMA, intein J is Ph0_IF2, intein K is Pho_VMA, intein L is Rma_DnaB, intein M is Sru_DnaB, intein N is Tag_Pol-1_Tsp-TY_Pol-1, intein O is Ter_RIR1-4, intein P is Tko_IF2 and intein Q is Tth-HB27_DnaE-2. At less than 100% identity, each N-intein:C intein pair forms a variant of the respective gp41-1, Cbu_DnaB, Mja_GF-6P, Mja_Hyp-1, Mja_IF2, Mja_Pol-1, Pab_CDC21-1, Pab_IF2-N, Pab_VMA, iPh0_IF2, Pho_VMA, Rma_DnaB, Sru_DnaB, Tag_Pol-1_Tsp-TY_Pol-1, Ter_RIR1-4, Tko_IF2 and Tth-HB27_DnaE-2 inteins. The variant retains trans-splicing activity, which can be tested using bi-cistronic expression cassettes for restoration of protease activity described in Example 18.

As used herein, the term iProtease is an alternative name for an intein-modified protease. The first precursor may be referred to as an "NI," which may be an in frame fusion of 1) the protease N-terminal fragment (N-extein), to 2) the N-terminal part of the trans-splicing intein ($I^N$). The second precursor may be referred to as an "IC," which may be an in frame fusion of 1) the C-terminal part of the trans-splicing intein ($I^C$) to 2) the C-terminal fragment (C-extein) of the protease. The product of splicing may have the amino extein (N) and carboxy extein (C) seamlessly joined by a peptide bond and may be called "NC." The NC may be the target protease obtained by trans-splicing. If the N-extein comprised a pre-domain, auto-cleavage of the pro-domain after splicing may result in the active target protease. "(NI+IC) premix" refers to a mix of splicing components NI and IC in an inactive state that may have no protease activity but may be induced by dilution to splice and yield the fully active target protease.

In an embodiment, the NI and IC precursors may be solubility optimized versions of the prototype molecules iSavinase:S317-Gp41-1 NI (SEQ ID NO: 49) and IC (SEQ ID NO: 50). These precursors were described in PCT application PCT/US2013/063304, which was filed Oct. 3, 2013 and published on Apr. 4, 2014 as International Publication No. WO2014/055782, which is incorporated herein by reference as if fully set forth.

An intein-modified protease may include intein-modified protease components optimized for improved solubility. The optimized intein-modified protease components may have optimizations restricted only to intein parts to ensure splicing leaves the sequence of the target enzyme unchanged when the intein removes itself and seamlessly joins the flanking protein sequences with a peptide bond. Splicing may restore the intact protein to full protease activity. The first precursor of an intein-modified protease may comprise, consist essentially of, or consist of an amino acid sequence with at least at least 70, 72, 75, 80, 85, 90, 91, 92, 93, 94, 95, 96, 97, 98, 99, or 100% identity to SEQ ID NO: 1. The second precursor of an intein-modified protease may comprise, consist essentially of, or consist of an amino acid sequence with at least at least 70, 72, 75, 80, 85, 90, 91, 92, 93, 94, 95, 96, 97, 98, 99, or 100% identity to SEQ ID NO: 2.

FIG. 1 shows schematic drawings of the solubility optimized molecules. Referring to FIG. 1, Savinase may be split between catalytic residues to Sav-N and Sav-C. Referring to FIG. 1, catalytic residues may be: D (Asp143), H (His172), and S (Ser326). The relative positions of these residues are marked by vertical lines. Intein parts $I^N$ and $I^C$ may be attached to Savinase parts Sav-N and Sav-C, respectively. Solubility engineering may be restricted to the intein parts. Solubility enhancer Trx domains may be attached to each intein part via a DPNG (Asp-Pro-Asn-Gly; SEQ ID NO: 5) linker. The C-intein part ($I^C$) may have multiple mutations for enhanced solubility. These may be M89A, L91T, L95T, L122G (numbering is by the position in the fused $I^N+I^C$).

Solubility optimized NI, termed NI-DPNG-Trx, may have a C-terminal solubility enhancer thioredoxin domain (SEQ ID NO: 51) fused via an Asp-Pro-Asn-Gly (DPNG; SEQ ID NO: 5) linker to the C-terminal end of the Gp41-1 N-intein ($I^N$; SEQ ID NO: 14) in the iProtease:S317-Gp41-1N. In the solubility optimized IC, termed Trx-DPNG-MTT IC[G122L], the thioredoxin domain (SEQ ID NO: 5) is fused via an Asp-Pro-Asn-Gly (DPNG; SEQ ID NO: 5) linker N-terminal to the mutated C-intein ($I^C$; SEQ ID NO: 15) of the iProtease:S317-Gp41-1C. The Trx in the NI (termed Trx-1) is nine aa residue longer at the C-terminus than the Trx in the IC (termed Trx-2). The mutated C-intein (SEQ ID NO: 15), MTT-IC[L122G] may have four solubility enhancer mutations at positions 89, 91, 95, and 122 as follows: M89Δ, L91T, L95T and L122G (numbering is by the position in the fused $I^N+I^C$ of GP41-1).

In an embodiment, the intein may be fused to the target protease in such a position as to substantially reduce or inhibit the activity of the target protease. In other words, the fragments of the protease included in the first precursor and the second precursor have no or substantially reduced protease activity in comparison to the intact target protease. The substantially reduced activity may be 40% to 35%, 35% to 30%, 30% to 25%, 25% to 20%, 20% to 15%, 15% to 10%, 10% to 5%, 5% to 1%, 1% to 0.5% of the activity of the intact target protease, or any value in a range between any two of the foregoing (endpoints inclusive). The activity of the target protease may be restored upon splicing of the intein. Activity may be analyzed by a Savinase enzyme assay outlined in Example 2.

An embodiment comprises a composition comprising the precursors (NI and IC) of any intein-modified protease herein. The first precursor NI may comprise, consist essentially of, or consists of an amino acid sequence with at least 70, 72, 75, 80, 85, 90, 91, 92, 93, 94, 95, 96, 97, 98, 99, or 100% identity to a reference sequence of SEQ ID NO: 1. The first precursor may be capable of trans-splicing with the second precursor to form the target protease. The second precursor IC may comprise, consist essentially of, or consist of an amino acid sequence with at least 70, 72, 75, 80, 85, 90, 91, 92, 93, 94, 95, 96, 97, 98, 99, or 100% identity to a reference sequence of SEQ ID NO: 2. The second precursor may be capable of trans-splicing with the first precursor to form the target protease. The concentration of the first precursor or the second precursor may be in a range from 0.01% (v:v) to 10% (v:v). The concentration may be 0.02% (v:v), 0.03% (v:v), 0.04% (v:v), 0.05% (v:v), 0.06% (v:v), 0.07% (v:v), 0.08% (v:v), 0.09% (v:v), 0.1% (v:v), 0.2% (v:v), 0.3% (v:v), 0.4% (v:v), 0.5% (v:v), 0.6% (v:v), 0.7% (v:v), 0.8% (v:v), 1.0% (v:v), 2.0% (v:v), 3.0% (v:v), 4.0% (v:v), 5.0% (v:v), 6.0% (v:v), 7.0% (v:v), 8.0% (v:v), 9.0% (v:v), or 10.0% (v:v), or any value between any two of the foregoing concentration points. The concentration of the first precursor or the second precursor may be in a range from 0.3% (v:v) to 4% (v:v). The concentration may be 0.3% (v:v), 0.4% (v:v), 0.5% (v:v), 0.6% (v:v), 0.7% (v:v), 0.8% (v:v), 1.0% (v:v), 2.0% (v:v), 3.0% (v:v), or 4.0% (v:v), or any value between any two of the foregoing concentration points. The concentration of the first precursor or the second precursor may be at least 0.3% (v:v), at least 0.4% (v:v), at least 0.5% (v:v), at least 0.6% (v:v), at least 0.7% (v:v), at least 0.8% (v:v), at least 1.0% (v:v), at least 2.0% (v:v), at least 3.0% (v:v), or at least 4.0% (v:v), or at least any value between any two of the foregoing concentration points. As used above, the concentration 10% (v:v) corresponds to a concentration of 381.00 µM, 5% (v:v) corresponds to a concentration of 190.50 µM, 1% (v:v) corresponds to a concentration of 38.1 µM, 0.50% (v:v) corresponds to 19.05 µM, and 0.1% (v:v) corresponds to 3.81 µM.

The composition may further comprise at least one or more of effectors, components of a home care product or other ingredients. The one or more effectors may comprise one or more of sodium salt supplements, potassium salt supplements, ammonium salt supplements, charged polymeric salt supplements, polyol supplements, sodium chloride, tetrasodium iminodisuccinate, disodium succinate, disodium tartrate, potassium lactate, potassium citrate, potassium chloride, sodium nicotinate, ammonium sulfate, ammonium nitrate, lithium citrate, sodium polyaspartate, sodium polyacrylate, tetraethylene glycol, polyethylene glycol, tetraglycol, propylene carbonate, mono propylene glycol, glycerol, and tomadol. The potassium chloride concentration may be in a range from 0.1 M to 5.0 M. The concentration may be 0.1 M, 0.2 M, 0.3 M, 0.4 M, 0.5 M, 0.6 M, 0.7 M, 0.8 M, 0.9 M, 1.0 M, 1.1 M, 1.2 M, 1.3M, 1.4M, 1.5 M, 1.6 M, 1.7 M, 1.8 M, 1.9 M, 2.0 M, 2.1 M, 2.2 M, 2.3 M, 2.4 M, 2.5 M, 2.6 M, 2.7 M, 2.8 M, 2.9 M, 3.0 M, 3.1 M, 3.2 M, 3.3 M, 3.4 M, 3.5 M, 3.6 M, 3.7 M, 3.8 M, 3.9 M, 4.0 M, 4.1 M, 4.2 M, 4.3 M, 4.4 M, 4.5 M, 4.6 M, 4.7 M, 4.8 M, 4.9, 5.0 M, or any value between any two of the foregoing concentration points. The potassium chloride concentration may be in a range from 0.5 M to 2.0 M. The concentration may be 0.5 M, 0.6 M, 0.7 M, 0.8 M, 0.9 M, 1.0 M, 1.1 M, 1.2 M, 1.3M, 1.4M, 1.5 M, 1.6 M, 1.7 M, 1.8 M, 1.9 M, 2.0 M0.5 M, 0.6 M, 0.7 M, 0.8 M, 0.9 M, 1.0 M, 1.1 M, 1.2 M, 1.3M, 1.4M, 1.5 M, 1.6 M, 1.7 M, 1.8 M, 1.9 M, 2.0 M, or any value between any two of the foregoing concentration points. The concentrations of any one of the effectors listed herein may be the same or similar to the concentrations of the potassium chloride described.

The components of a composition or home care product herein may comprise at least one of a detergent, a soap, an industrial cleaner or a dishwashing liquid.

The detergent in a composition, home care product, or method herein may be any detergent. The detergent may be any commercially available detergent. The detergent may be but is not limited to GRESINOL™, SEVENTH GENERATION™, MYERS™, TIDE™, DREFT™, PUREX™, BIOKLEEN™, SUN AND EARTH™, GAIN™, ALL™, WOOLITE™, XTRA™, FAB™, SNUGGLE™, CHEER™, WISK™, SURF™, OMO™, PERSIL™, BREEZE™, SKIP™, ALA™, RINSO™ or GREENSHIELD™. The soap may be any soap. The soap may be any commercially available soap. The soap may be but is not limited to IVORY™, DIAL™, DOVE™, SOFTSOAP™, METHOD™, KLEENEX™, or CAREX™.

The industrial cleaner may be any industrial cleaner. The industrial cleaner may be any commercially available industrial cleaner. The industrial cleaner may be but is not limited to ELIMINATOR™ (caustic additive), ALKAZOLV™, ULTRAZOLV™ 700, CONCEPT™ C20, PERFORM™, or REFLEX™ B165. The industrial cleaner may be but is not limited to Caustic, NaOH (1%), EDTA, sodium hypochlorite, or nitric acid (1%).

The dishwashing liquid may be any dishwashing liquid. The dishwashing liquid may be any commercially available dishwashing liquid. The dishwashing liquid may be but is not limited to CASCADE™, JOY™, PALMOLIVE™, GAIN™, GLO™, DAWN™, GREEN WORKS™, ULTRA™, ZIP™, CLOROX™, TRIM™, or TAJ™.

The detergent concentration may be in a range from 40% (v:v) to 100% (v:v). The concentration may be 40% (v:v), 45% (v:v), 50% (v:v), 55% (v:v), 60% (v:v), 65% (v:v), 70% (v:v), 75% (v:v), 80% (v:v), 90% (v:v), 91% (v:v), 92% (v:v), 93% (v:v), 94% (v:v), 95% (v:v), 96% (v:v), 97% (v:v), 98% (v:v), 99% (v:v), or 100% (v:v) or any value between any two of the foregoing concentration points. The detergent concentration may be in a range from 65% to 100%. The concentration may be 65% (v:v), 70% (v:v), 75%

(v:v), 80% (v:v), 90% (v:v), 91% (v:v), 92% (v:v), 93% (v:v), 94% (v:v), 95% (v:v), 96% (v:v), 97% (v:v), 98% (v:v), 99% (v:v), or 100% (v:v), or any value between any two of the foregoing concentration points. The concentrations of any one of the soaps, industrial cleaners, or dishwashing liquids listed herein may be similar to the concentrations of the detergent. The percent detergent listed here refers to the percent of stock detergent in comparison to the final volume of the home care product or composition.

The components of the home care product, or a composition herein, may further comprise at least one ingredient selected from the group consisting of: water softeners, surfactants, bleach, enzymes, brighteners, fragrances, anionic surfactants, nonionic surfactants, builders to remove the hardness ions, antiredeposition agents, dye transfer inhibitors, soil release polymers, optical brighteners, enzyme stabilizers, viscosity control compounds, pH control compounds, soap and silicones to control excessive foaming, preservatives for microbial control, perfume and dye for scent and appearance, bleaching agents, water, solubilizers, alkylbenzenesulphonates, ethoxylated fatty alcohols, sodium citrate, tetrasodium EDTA or an acrylic polymer, PVP K-30, Chromabond S-100, Chromabond S-400, Sorez 100, Repel-O-Tex SRP-6, Tinopal CBS-X, calcium chloride, sodium tetraborate, propylene glycol, sodium formate, sodium citrate, monoethanolamine, propylene glycol, sodium xylene sulfonate, polymers, and citric acid. The composition may further comprise a detergent as a fuel additive. The fuel additive may be a long-chain amine or amide. The fuel additive may be a polyisobuteneamine or polyisobuteneamide/succinimide. The composition may comprise a detergent as a biological reagent. The biological reagent may be used for isolation and purification of integral membrane proteins found in biological cells. The concentrations of any one of the additional ingredients listed herein may be any concentrations known in the art.

In an embodiment, the composition may comprise 0.5% (v:v) of the first precursor, 0.5% (v:v) of the second precursor, 1M KCl and variable concentrations of detergent. The variable concentrations of the detergent may be in a range from 65% (v:v) to 100% (v:v). The composition may comprise 38.1 μM of each of the first precursor and the second precursor, 1M KCl and variable concentrations of detergent.

The following exemplary detergent formulations may be a detergent added as a stock detergent to a composition or home product herein to a desired concentration, or provided in a method herein. An exemplary detergent formulation may include Aduxol, castor oil ethoxylate, fatty alcohol, ethoxylate, polyethylene glycol, alkoxylated carboxylic acid, glycerol, Neodol, MPG, TEA, MEA, PRIFAC™ 5908, LAS acid, citric acid, sodium sulfite, SOKALAN HP20, SLES 3EO, DEQUEST™ 2010 and deionized water. Further exemplary detergents may be found in U.S. Pat. No. 4,115,292, Richardson et al., filed as U.S. application Ser. No. 05/789,325 on Apr. 20, 1977 and issued on Sep. 19, 1973; U.S. Pat. No. 3,717,630, Booth, issued on Feb. 20, 1967; U.S. Pat. No. 3,332,880, Kessler et al., issued on Jul. 25, 1967, all of which are both of which are incorporated herein by reference. An exemplary type of anionic surfactant may be found in U.S. Pat. No. 3,941,710, Gilbert et al., issued Mar. 2, 1976, which is incorporated herein by reference as if fully set forth. An exemplary listing of classes and species of nonionic surfactants useful herein may be found in U.S. Pat. No. 3,664,961, Norris, issued on Mar. 23, 1972, which is incorporated herein by reference as if fully set forth.

An exemplary formulation of a liquid laundry detergent enhanced with natural essence and further comprising non-petroleum source anionic and nonionic surfactants, naturally occurring builders is disclosed in U.S. Pat. No. 7,648,953, Bastigket et al., filed on May 8, 2008 as U.S. application Ser. No. 12/151,597 and issued Jan. 19, 2010, which is incorporated herein by reference as if fully set forth. The formulation disclosed in this patent includes the following ingredients: surfactant mixture consisting of: about 1% to about 20% by weight of an alkyl ether sulfate of the general formula R—(OCH$_2$CH$_2$)$_x$—O—SO$_3$M, where R is a non-petroleum derived fatty alcohol with even number carbon chain lengths of from about C$_8$ to about C$_{20}$, and where x is from about 0.5 to about 8, and where M is an alkali metal or ammonium cation; from about 1% to about 10% by weight of a fatty alcohol ethoxylate of general formula R—(OCH$_2$CH$_2$)$_x$—OH, where R is a non-petroleum derived fatty alcohol with even number carbon chain lengths of from about C$_{10}$ to about C$_{18}$, and where x is from about 0.5 to about 9; and optionally from about 1% to about 10% by weight of a fatty acid soap; from about 0.1% to about 5% of a natural essence; from about 0.1% to about 10% by weight of a builder; and water.

An exemplary formulation of liquid laundry detergent compositions that includes anionic surfactant, fabric care agent, cationic deposition aid and performance booster are disclosed in European Publication No. EP2126017 A1, Panandiker et al, filed Feb. 12, 2009, which is incorporated herein by reference as if fully set forth. The performance booster in this formulation is chosen such that it will not react with the cationic deposition aid or fabric care agent to form a coacervate and/or to precipitate from solution. The liquid laundry detergent formulation comprises by weight percentage of said composition: a. from 1% to 80% of anionic surfactant; b. from 0.1% to 10% of fabric care agent; c. from 0.01% to 2% of deposition aid; and d. from 0.05% to 10% of performance booster selected from enzymes, anionic polymers, and brighteners. The anionic surfactant is selected from the group of: C8-C$_{22}$ fatty acid or its salts; Cn-Ci$_8$ alkyl benzene sulfonates; C$_1$O-C$_2$O branched-chain and random alkyl sulfates; C$_{10}$-C$_{18}$ alkyl alkoxy sulfates, wherein x is from 1-30; mid-chain branched alkyl sulfates; mid-chain branched alkyl alkoxy sulfates; Ci$_0$-Ci$_8$ alkyl alkoxy carboxylates comprising 1-5 ethoxy units; modified alkylbenzene sulfonate; C$_{12}$-C$_{20}$ methyl ester sulfonate; Ci$_0$-Ci$_8$ alpha-olefin sulfonate; C$_6$-C$_{20}$ sulfosuccinates; and combinations thereof. The fabric care agent provides fabric care benefits selected from the group of: fabric softening; color protection; color restoration; pill/fuzz reduction; anti-abrasion; anti-wrinkling; and combinations thereof. The fabric care agent is selected from the group of: silicone derivates; oily sugar derivatives; dispersible polyolefins; polymer latexes; cationic surfactants; and combinations thereof. Enzyme is selected from the group of: proteases; amylases; lipases; cellulases; carbohydrase; xyloglucanase; mannanase; pectate lyase; and combinations thereof. Performance booster is a brightener preferably selected from the group of: disodium 4,4'-bis-(2-sulfostyryl) biphenyl; benzenesulfonic acid; 2,2'-(1,2-ethenediyl)bis[5-[4-[(2-hydroxy-ethyl)methylamino]-6-(phenylamino)-1,3,5-triazin-2-y] amino]-, disodium salt; disodium 4,4'-bis{[4-anilino-6-[bis (2-hydroxyethyl)amino-s-triazin-2yl]-amino}-2,2'-stilbenedisulfonate; disodium 4,4'-bis[(4-anilino-6-(N-2-hydroxyethyl-N-methylamino)-s-triazine-2-yl)amino]2,2'-stilbenedisulfonate; disodium 4,4'-bis{[4-anilino-6-methylamino-s-triazin-2-yl]-amino}-2,2'-stilbenedisulfonate; disodium 4,4"-bis[4,6-di-anilino-s- triazin-2-yl]-2,2'-stilbenedisulfonate; disodium 4, 4'-bis{[4-anilino-6-morpholino-s-triazin-2-yl]-amino}-2,2'-stilbenedisulfonate; and combinations thereof. Performance booster is an anionic dispersant polymer. The composition may further comprise a pearlescent agent preferably selected from the group of: mica; bismuth oxychloride; fish scales; mono and diesters of alkylene glycol. Pearlescent agent may be selected from the group of: mica; ethylene glycol distearate; ethylene glycolmonostearate; bismuth oxychloride; and combinations thereof. The composition may further comprise laundry adjuncts selected from the group of: nonionic surfactant; builder; polymeric soil release agent; and combinations thereof.

Exemplary detergent formulations may be found in International Publication No. WO2014019903, Carswel et al., published Feb. 6, 2014, which is incorporated herein by reference as if fully set forth. This application discloses an alkaline liquid laundry detergent comprising at least 1 wt % triethanolanmine, at least 5 wt % non-soap surfactant and at least 0.5 wt % of a polyester according to the following formula (I) wherein R1 and R2 independently of one another are X—(OC2H4)n-(OC3H6)m wherein X is $C_{1-4}$ alkyl, the —(OC2H4) groups and the —(OC3H6) groups are arranged blockwise and the block consisting of the —(OC3H6) groups is bound to a COO group or are HO—(C3H6), n is based on a molar average a number of from 12 to 120, preferably 40 to 50, m is based on a molar average a number of from 1 to 10, and a is based on a molar average a number of from 4 to 9.

Exemplary detergent formulations may be found in International Publication No. WO2013160023, Best et al., published Oct. 31, 2013, which is incorporated herein by reference as if fully set forth. This application discloses an externally structured aqueous isotropic liquid laundry detergent composition comprising: at least 10 wt % water, at least 10 wt % of a mixed surfactant system comprising anionic surfactant, an external structuring system comprising from 0.025 to 0.15 wt % insoluble cellulosic fibre comprising at least 50 wt % activated citrus fibre,—at least 0.01 wt % suspended non-clay solid particles, characterised in that the external structuring system further comprises at least 0.1 wt % water-swellable clay.

Exemplary detergent formulations may be found in U.S. Pat. No. 5,731,278, Nair at al., filed on Oct. 29, 1996 and issued on Mar. 24, 1998, which is incorporated herein by reference as if fully set forth. This reference discloses a liquid laundry detergent that contains a surfactant component, a formate thickener component, a selected perfume component and a relatively large amount of an aqueous liquid carrier.

Exemplary detergent formulations may be found in International Publication No. WO1999049009, Depoot et al, published Sep. 30, 1999, which is incorporated herein by reference as if fully set forth. This application discloses a liquid laundry detergent comprising HEDP, and water soluble and/or dispersible, modified polyamines having functionalized backbone moieties which provide a stabilizing effect.

Exemplary detergent formulations may be found in International Publication No. WO1998013461, McIver et al., published on Apr. 2, 1998, which is incorporated herein by reference as if fully set forth. This application discloses a liquid laundry detergent comprising one or more of the following: suds boosters, builders, soil release polymers, polyacrylate polymers, dispersing agents, dye transfer inhibitors, dyes, perfumes, processing aids, brighteners, and mixtures thereof.

Exemplary detergent formulations may be found in European Publication No. EP0929642, McIver et al. published on Jul. 21, 1999, which is incorporated herein by reference as if fully set forth. This application discloses a liquid laundry detergent comprising one or more of the following: suds boosters, builders, soil release polymers, polyacrylate polymers, dispersing agents, dye transfer inhibitors, dyes, perfumes, processing aids, brighteners, and mixtures thereof.

Exemplary liquid laundry detergent formulations containing anionic surfactants may be found in European Publication No. EP2551335, Souter et al., published Jan. 1, 2013, which is incorporated herein by reference as if fully set forth.

Exemplary detergent formulations may be found in International Publication No. WO2014190131, Frankenbach et al., published Nov. 27, 2014, which is incorporated herein by reference as if fully set forth. This application discloses a liquid laundry detergent comprising branched surfactants.

Exemplary detergent formulations may be found in European Publication No. EP2712913, Guida et al, published Apr. 2, 2014, which is incorporated herein by reference as if fully set forth. This publication discloses a liquid laundry detergent comprising crystallized triglycerides including crystallized hydrogenated castor oil (HCO), surfactant and organic non-aminofunctional alcohols.

Exemplary detergent formulations may be found in Chinese Publication No. CN103242973, Zhu et al., published Aug. 14, 2014, which is incorporated herein by reference as if fully set forth. This application discloses a liquid laundry detergent comprising 0.02-15% of cationic softener, 0.01-10% of modified silicon oil, 2-50% of nonionic surfactant.

Exemplary detergent formulations may be found in European Publication No. EP2855408, Ellison et al., published Apr. 8, 2015, which is incorporated herein by reference as if fully set forth. This publication discloses a liquid laundry detergent made by dimerizing one or more even numbered alpha olefins to produce one or more vinylidenes; hydroformylating the vinylidene(s) to produce a mixture of alcohols; and sulfating the mixture of alcohols to form alcohol sulfates.

An embodiment provides an expression cassette. The expression cassette may comprise one or more polynucleotide encoding an intein-modified protease having an enhanced solubility. The encoded intein-modified protease may be any one of the intein-modified proteases described herein. The expression cassette may comprise a polynucleotide encoding a first precursor. The expression cassette may comprise a polynucleotide encoding the second precursor. The expression cassette may comprise a polynucleotide encoding a first precursor and a second precursor. The one or more polynucleotides may comprise, consist essentially of, or consist of a sequence with at least 70, 72, 75, 80, 85, 90, 91, 92, 93, 94, 95, 96, 97, 98, 99, or 100% identity to a reference sequence of SEQ ID NO: 3, which is a sequence encoding the first precursor NI-DPNG-Trx shown in FIG. 1. The one or more polynucleotides may comprise, consist essentially of, or consist of a sequence with at least 70, 72, 75, 80, 85, 90, 91, 92, 93, 94, 95, 96, 97, 98, 99, or 100% identity to SEQ ID: 4, which is a sequence encoding the second precursor Trx-DPNG-MTT-IC shown in FIG. 1.

The one or more polynucleotides may include a sequence encoding any one of the target proteases described herein. The one or more polynucleotides may together encode the parts of Subtilisin Carlsberg, Subtilisin BPN, SAPB from *Bacillus pumilus* (CBS), BPP-A protease from *B. pumilus* MS-1, or AprB from *Bacillus* sp. B001 protease. The one or more polynucleotides may encode a protease from *Bacillus* licheniformis (UniProt accession number is: Q6PNN5. The one or more polynucleotides may comprise, consist essentially of, or consist of a sequence with at least 70, 72, 75, 80, 85, 90, 91, 92, 93, 94, 95, 96, 97, 98, 99, or 100% identity to SEQ ID NO: 7, which is a sequence encoding a Savinase.

The expression cassette may comprise one or more polynucleotides encoding any one of the inteins described herein. The one or more polynucleotides may encode the N-intein and C-intein parts of gp41-1, Cbu_DnaB, Mja_GF-6P, Mja_Hyp-1, Mja_IF2, Mja_Pol-1, Pab_CDC21-1, Pab_IF2-N, Pab_VMA, Pho_IF2, Pho_VMA, Rma_DnaB, Sru_DnaB, Tag_Pol-1_Tsp-TY_Pol-1, Ter_RIR1-4, Tko_IF2, or Tth-HB27_DnaE-2 intein. Two polynucleotides of the one or more polynucleotides may comprise, consist essentially of, or consist of a sequence with at least 70, 72, 75, 80, 85, 90, 91, 92, 93, 94, 95, 96, 97, 98, 99, or 100% identity to SEQ ID NO: 10, which a sequence encoding the gp41-1 intein. The one or more polynucleotide may encode N-intein of the intein, C-intein of the intein or both. The one or more polynucleotide may comprise, consist essentially of, or consist of a sequence with at least 70, 72, 75, 80, 85, 90, 91, 92, 93, 94, 95, 96, 97, 98, 99, or 100% identity to SEQ ID NO: 12, which is a sequence encoding the gp41-1 N-intein. The one or more polynucleotide may comprise, consist essentially of, or consist of a sequence with at least 70, 72, 75, 80, 85, 90, 91, 92, 93, 94, 95, 96, 97, 98, 99, or 100% identity to SEQ ID NO: 13, which is a sequence encoding the gp41-1 C-intein.

The one or more polynucleotides may further encode a first solubility enhancer, a second solubility enhancer or both. The one or more polynucleotides may encode a Trx domain. A sequence of the one or more polynucleotides may comprise, consist essentially of, or consist of a sequence with at least 70, 72, 75, 80, 85, 90, 91, 92, 93, 94, 95, 96, 97, 98, 99, or 100% identity to SEQ ID NO: 52, which is a sequence encoding the Trx domain included in NI shown in FIG. 1. A sequence of the one or more polynucleotides may comprise, consist essentially of, or consist of a sequence with at least 70, 72, 75, 80, 85, 90, 91, 92, 93, 94, 95, 96, 97, 98, 99, or 100% identity to SEQ ID NO: 54, which is a sequence encoding the Trx domain included in IC shown in FIG. 1.

An embodiment comprises a polynucleotide comprising, consisting essentially of, or consisting of a sequence that has at least 70, 72, 75, 80, 85, 90, 91, 92, 93, 94, 95, 96, 97, 98, 99, or 100% identity along its length to a contiguous portion of a polynucleotide having any one of the sequences set forth herein or the complements thereof. The contiguous portion may be any length up to the entire length of a sequence set forth herein or the complement thereof.

Determining percent identity of two amino acid sequences or two nucleic acid sequences may include aligning and comparing the amino acid residues or nucleotides at corresponding positions in the two sequences. If all positions in two sequences are occupied by identical amino acid residues or nucleotides then the sequences are said to be 100% identical. Percent identity is measured by the Smith Waterman algorithm (Smith T F, Waterman M S 1981 "Identification of Common Molecular Subsequences," J Mol Biol 147: 195-197, which is incorporated herein by reference as if fully set forth).

In an embodiment, trans-splicing intein technology may be used to regulate protease activity. In this approach, a protease may be split between catalytic residues in two inactive fragments, which may be individually expressed as fusion to trans-splicing inteins. Mixing may trigger trans-intein mediated association of inactive fragments, splicing and seamless joining of the inactive parts by a peptide bond to fully functional active protease.

Construction, expression and detergent dilution inducible properties of a trans-splicing intein regulated liquid laundry protease, Savinase, have been described in PCT/US2013/063304, which is incorporated by reference herein as if fully set forth. Methods that improve formulation stability and detergent dilution inducible protease activity to levels relevant in commercial liquid laundry application are described herein.

An embodiment provides a method of regulating protease activity. The method includes combining any one or more of the intein-modified proteases disclosed herein with components of a home care product and may include one or more effectors to form a mixture. As used herein, home care products refers to any product used for cleaning or treating the home or its content. The home care products herein include personal care products for cleaning or conditioning of the person. The intein-modified protease in the mixture may be inactive in terms of at least protease activity or splicing activity. The one or more effectors may be capable of suppressing splicing of the intein-modified protease in the mixture. The suppression may be reversible. The step of causing splicing may include one of diluting, reducing, or removing the one or more effectors. After splicing, protease activity of the target protease may be restored. The one or more effectors may be but are not limited to sodium salt supplements, potassium salt supplements, ammonium salt supplements, charged polymeric salt supplements, or polyol supplements. The one or more effectors may be selected from the group consisting of: sodium chloride, tetrasodium iminodisuccinate, disodium succinate, disodium tartrate, potassium lactate, potassium citrate, potassium chloride, sodium nicotinate, ammonium sulfate, ammonium nitrate, lithium citrate, sodium polyaspartate, sodium polyacrylate, tetraethylene glycol, polyethylene glycol, tetraglycol, propylene carbonate, mono propylene glycol, glycerol, and tomadol. The one or more effectors may include potassium chloride. The potassium chloride concentration may be in a range from 0.1 M to 5.0 M. The concentration may be 0.1 M, 0.2 M, 0.3 M, 0.4 M, 0.5 M, 0.6 M, 0.7 M, 0.8 M, 0.9 M, 1.0 M, 1.1 M, 1.2 M, 1.3M, 1.4M, 1.5 M, 1.6 M, 1.7 M, 1.8 M, 1.9 M, 2.0 M, 2.1 M, 2.2 M, 2.3 M, 2.4 M, 2.5 M, 2.6 M, 2.7 M, 2.8 M, 2.9 M, 3.0 M, 3.1 M, 3.2 M, 3.3 M, 3.4 M, 3.5 M, 3.6 M, 3.7 M, 3.8 M, 3.9 M, 4.0 M, 4.1 M, 4.2 M, 4.3 M, 4.4 M, 4.5 M, 4.6 M, 4.7 M, 4.8 M, 4.9, 5.0 M, or any value between any two of the foregoing concentration points. The potassium chloride concentration may be in a range from 0.5 M to 2.0 M. The concentration may be 0.5 M, 0.6 M, 0.7 M, 0.8 M, 0.9 M, 1.0 M, 1.1 M, 1.2 M, 1.3M, 1.4M, 1.5 M, 1.6 M, 1.7 M, 1.8 M, 1.9 M, 2.0 M0.5 M, 0.6 M, 0.7 M, 0.8 M, 0.9 M, 1.0 M, 1.1 M, 1.2 M, 1.3M, 1.4M, 1.5 M, 1.6 M, 1.7 M, 1.8 M, 1.9 M, 2.0 M, or any value between any two of the foregoing concentration points. The concentrations of any one of the effectors listed herein may be similar to the concentrations of the potassium chloride.

In an embodiment, the step of causing may include diluting the mixture with a liquid. The amount of the liquid added to the mixture in the diluting step may be an amount satisfying a ratio of the mixture to liquid selected from the value of less than or equal to one of 1:5 (v:v), 1:10 (v:v), 1:20 (v:v), 1:50 (v:v): 1:60 (v:v), 1:70 (v:v), 1:80 (v:v), 1:90 (v:v), 1:100 (v:v), 1:150 (v:v), 1:200 (v:v), 1:250 (v:v), 1:300 (v:v), 1:350 (v:v), or 1:400 (v:v), or any ratio in a range between any two of the foregoing (endpoints inclusive). For example, the mixture to liquid ratio may be a value less than any integer or non-integer number selected from 1:5 to 1:10. The mixture-to-liquid ratio may be equal to 1:5 (v:v), 1:10 (v:v), 1:20 (v:v), 1:50 (v:v): 1:60 (v:v), 1:70 (v:v), 1:80 (v:v), 1:90 (v:v), 1:100 (v:v), 1:150 (v:v), 1:200 (v:v), 1:250 (v:v), 1:300 (v:v), 1:350 (v:v), or 1:400 (v:v) or any ratio in a range between any two of the foregoing (endpoints inclusive). For example, the liquid to mixture ratio may be a value equal to any integer or non-integer number in the range from 1:5 to 1:10. The liquid may be water. The liquid may be an aqueous buffer. The components of the home care product may be but is not limited to detergent, soap, industrial cleaner, or dish washing liquid. The dilution may cause splicing of the intein-modified protease and restoring activity of the target protease.

An embodiment provides a method of screening for effectors of dilution inducible intein-modified protease activity in liquid laundry detergent. The method may comprise mixing liquid laundry detergent with any one of the first precursor and the second precursor described herein to obtain a mixture. The method may comprise adding one or more compounds to the mixture. The method may comprise diluting the mixture with a liquid. The method may also comprise identifying compounds that suppress splicing of the N-intein and C-intein included in the respective first and second precursors and restoring the activity of the target protease. An embodiment also provides adding one or more effectors to a liquid laundry detergent formulated mixtures to reversibly inhibit an intein-modified protease.

An embodiment provides a home care product. The home care product may include any one of the intein-modified proteases disclosed herein and one or more effectors. The home care product may comprise a dishwashing detergent, a laundry detergent, an industrial cleaner, or a soapless soap. As used herein, the term "detergent" refers to a surfactant or a mixture of surfactants. The term "soapless soap" refers to a soap free liquid cleanser with a slightly acidic pH. The home care product may comprise any other type of a cleaning agent.

The home care product may comprise detergent as powder. The home care product may comprise detergent provided in liquid formulation. The liquid detergent formulation may contain water softeners, surfactants, bleach, enzymes, brighteners, fragrances, and many other agents. The liquid detergent formulation may include a combination of anionic and nonionic surfactants, builders to remove the hardness ions, a variety of antiredeposition agents, dye transfer inhibitors that prevent dye from coming off one fabric and getting deposited on another, soil release polymers to provide a barrier to the fabric, optical brighteners, enzyme stabilizers, viscosity control compounds, pH control compounds, soap and silicones to control excessive foaming, preservatives for microbial control, perfume and dye for scent and appearance, bleaching agents, water, solubilizers or other additives to improve performance characteristics. The liquid detergent formulation may comprise anionic surfactants that are alkylbenzenesulphonates, or other anionic surfactants. The liquid detergent formulation may comprise nonionic surfactants that are ethoxylated fatty alcohols. The liquid detergent formulation may comprise builder to remove the hardness ions selected from sodium citrate, tetrasodium EDTA or an acrylic polymer. The liquid detergent formulation may comprise a dye transfer inhibitor selected from PVP K-30, Chromabond S-100, or Chromabond S-400. The liquid detergent formulation may comprise a soil release polymer selected from Sorez 100 a polyethylene glycol polyester copolymer, or Repel-O-Tex SRP-6, a polyethylene glycol polyester. The liquid detergent formulation may comprise the optical brightener that is Tinopal CBS-X, or any other optical brightener. The liquid detergent formulation may comprise the enzyme stabilizer selected from calcium chloride, sodium tetraborate, propylene glycol, sodium formate, sodium citrate or monoethanolamine. The liquid detergent formulation may comprise the viscosity control compound of propylene glycol, sodium xylene sulfonate, or polymers. The liquid detergent formulation may comprise the pH control compound of citric acid or monoethanolamine.

The home care product herein may include one or more effectors. The one or more effectors may be but are not limited to sodium chloride, tetrasodium iminodisuccinate, disodium succinate, disodium tartrate, potassium lactate, potassium citrate, potassium chloride, sodium nicotinate, ammonium sulfate, ammonium nitrate, lithium citrate, sodium polyaspartate, sodium polyacrylate, tetraethylene glycol, polyethylene glycol, tetraglycol, propylene carbonate, mono propylene glycol, glycerol, or tomadol.

An embodiment provides a method of storing a protease in a mixture. The method may include making any one intein-modified proteases described herein. The method may include combining the intein-modified protease with a home care product and one or more effectors to form a mixture. The home care product may be selected from the group consisting of: detergent, soap, industrial cleaner, and dish washing liquid. The one or more effectors may be selected be any one of effectors disclosed herein. The mixture may be stored for any length of time. The mixture may be stored, for a period of time from one hour to a year. The mixture may be stored for one week, two weeks, three weeks, four weeks, five weeks, six weeks, seven weeks, or eight weeks.

The home care product may include iProtease, which refers to any one of the intein-modified proteases described herein. The home care product may comprise iSavinase. iSavinase storage stability in liquid laundry detergents may be comparable with the inhibitor stabilized Savinase under accelerated ageing conditions over eight weeks. iSavinase stain removal activity on blood, milk or ink stained fabric (EMPA117) may be comparable with the intein unmodified Savinase at equimolar loading of the enzymes.

The following list includes particular embodiments of the present invention. But the list is not limiting and does not exclude alternate embodiments, or embodiments otherwise described herein. Percent identity described in the following embodiments list refers to the identity of the recited sequence along the entire length of the reference sequence.

EMBODIMENTS

1. An intein-modified protease comprising: a first precursor and a second precursor: the first precursor comprises an N-extein of a target protease fused to a solubility enhanced N-intein of a trans-splicing intein, and the carboxy terminus of the N-extein is fused to the amino terminus of the solubility enhanced N-intein; the second precursor comprises a solubility enhanced C-intein of the trans-splicing intein fused to a C-extein of the target protease, and the carboxy terminus of the solubility enhanced C-intein is fused to the amino terminus of the C-extein; and the first precursor is separated from the second precursor prior to trans-splicing; wherein the intein-modified protease has enhanced solubility and reduced or inhibited activity compared to the target protease and the activity of the target protease is obtained upon trans-splicing of the intein-modified protease and fusion of the N-extein and the C-extein.

2. The intein-modified protease of embodiment 1, wherein the solubility enhanced N-intein comprises an N-intein and a first solubility enhancer and the carboxy terminus of the N-intein is fused to the first solubility enhancer by a first linker.

3. The intein-modified protease of one or both of embodiments 1-2, wherein the solubility enhanced C-intein includes a C-intein and a second solubility enhancer, and the second solubility enhancer is fused to the amino terminus of the C-intein by a second linker.

4. The intein-modified protease of one or more of embodiments 2-3, wherein at least one of the first solubility enhancer or the second solubility enhancer is independently selected from the group consisting of: a thioredoxin domain Trx, small ubiquitin-related protein SUMO, glutathione-S transferase GST, maltose-binding protein MBP, N utilization substance A NusA, and seventeen kilodalton protein Skp.

5. The intein-modified protease of one or more of embodiments 2-4, wherein each of the first solubility enhance and the second solubility enhancer comprises a thioredoxin domain Trx.

6. The intein-modified protease of one or more embodiments 2-5, wherein the first solubility enhancer comprises, consists essentially of, or consists of an amino acid sequence with at least 70, 72, 75, 80, 85, 90, 91, 92, 93, 94, 95, 96, 97, 98, 99, or 100% identity to a sequence of SEQ ID NO: 51, and the second solubility enhancer comprises, consists essentially of, or consists of an amino acid sequence with at least 70, 72, 75, 80, 85, 90, 91, 92, 93, 94, 95, 96, 97, 98, 99, or 100% identity to a sequence of SEQ ID NO: 53.

7. The intein-modified protease of one or more of embodiments 2-6, wherein at least one of the first linker or the second linker is a DPNG linker.

8. The intein-modified protease of one or more of preceding embodiments, wherein the target protease is an enzyme selected from the group consisting of: EC3.4.99 proteases, EC3.4.21.62 proteases, keratinases, serine proteases, alkaline proteases, acid protease, metallo proteases, cysteine proteases, aspartate proteases, ATP-dependent proteases, and Subtilisin family proteases.

9. The intein-modified protease of one or more of preceding embodiments, wherein the target protease comprises a target protease selected from the group consisting of a Savinase, an alkaline protease Q6PNN5, and acid protease B8NLY9_PEPA_ASPEN.

10. The intein-modified protease of one or more of preceding embodiments, wherein the target protease comprises, consists essentially of, or consists of an amino acid sequence with at least 70, 72, 75, 80, 85, 90, 91, 92, 93, 94, 95, 96, 97, 98, 99, or 100% identity to a sequence selected from the group consisting of SEQ ID NO: 6, 8 and 9.

11. The intein-modified protease of one or more of preceding embodiments, wherein the intein is selected from the group consisted of: gp41-1, Cbu_DnaB, Mja_GF-6P, Mja_Hyp-1, Mja_IF2, Mja_Pol-1, Pab_CDC21-1, Pab_IF2-N, Pab_VMA, Pho_IF2, Pho_VMA, Rma_DnaB, Sru_DnaB, Tag_Pol-1_Tsp-TY_Pol-1, Ter_RIR1-4, Tko_IF2, and Tth-HB27_DnaE-2 intein.

12. The intein-modified protease of one or more of preceding embodiments, wherein the intein is gp41-1 intein and comprises, consists essentially of, or consists of an amino acid sequence with at least 70, 72, 75, 80, 85, 90, 91, 92, 93, 94, 95, 96, 97, 98, 99, or 100% identity to SEQ ID NO: 11.

13. The intein-modified protease of one or more of preceding embodiments, wherein the N-intein comprises, consists essentially of, or consists of an amino acid sequence with at least 70, 72, 75, 80, 85, 90, 91, 92, 93, 94, 95, 96, 97, 98, 99, or 100% identity a sequence selected from the group consisting of SEQ ID NOS: 14, 16, 18, 20, 22, 24, 26, 28, 30, 32, 34, 36, 38, 40, 42, 44, and 46 and the C-intein comprises, consists essentially of, or consists of an amino acid sequence with at least 70, 72, 75, 80, 85, 90, 91, 92, 93, 94, 95, 96, 97, 98, 99, or 100% identity a sequence selected from the group consisting of SEQ ID NOS: 15, 17, 19, 21, 23, 25, 27, 29, 31, 33, 35, 37, 39, 41, 43, 45, and 47, and the N-intein and the C-intein together form a trans-splicing intein or variant thereof selected from the group consisting of: gp41-1, Cbu_DnaB, Mja_GF-6P, Mja_Hyp-1, Mja_IF2, Mja_Pol-1, Pab_CDC21-1, Pab_IF2-N, Pab_VMA, Pho_IF2, Pho_VMA, Rma_DnaB, Sru_DnaB, Tag_Pol-1_Tsp-TY_Pol-1, Ter_RIR1-4, Tko_IF2, and Tth-HB27_DnaE-2.

14. The intein-modified protease of one or more of preceding embodiments, wherein the first precursor comprises, consists essentially of, or consists of an amino acid sequence having 70, 72, 75, 80, 85, 90, 91, 92, 93, 94, 95, 96, 97, 98, 99, or 100% identity to a reference sequence of SEQ ID NO: 1.

15. The intein-modified protease of one or more of preceding embodiments, wherein the second precursor comprises, consists essentially of, or consists of an amino acid sequence having 70, 72, 75, 80, 85, 90, 91, 92, 93, 94, 95, 96, 97, 98, 99, or 100% identity to a reference sequence of SEQ ID NO: 2.

16. An expression cassette comprising one or more polynucleotides encoding a first precursor or a second precursor of an intein-modified protease, wherein the first precursor comprises an N-extein of a target protease fused to a solubility enhanced N-intein of a trans-splicing intein, and the carboxy terminus of the N-extein is fused to the amino terminus of the solubility enhanced N-intein; the second precursor comprises a solubility enhanced C-intein of the trans-splicing intein fused to a C-extein of the target protease, and the carboxy terminus of the solubility enhanced C-intein is fused to the amino terminus of the C-extein; and the first precursor is separated from the second precursor prior to trans-splicing; and wherein upon expression from the expression cassette the intein-modified protease would have enhanced solubility and reduced or inhibited activity compared to the target protease, and the activity of the target protease would restored upon trans-splicing of the intein-modified protease and fusion of the N-extein and the C-extein.

17. The expression cassette of embodiment 16, wherein the one or more polynucleotides encode the solubility enhanced N-intein comprising the N-intein and a first solubility enhancer, and the carboxy terminus of the N-intein is fused to the first solubility enhancer by a first linker.

18. The expression cassette of one or more of embodiments 16-17, wherein the one or more polynucleotides encode the solubility enhanced C-intein comprising a C-intein of an intein and the second solubility enhancer, and the second solubility enhancer is fused to the amino terminus of the C-intein by a second linker.

19. The expression cassette of one or more of embodiments 16-18, wherein the one or more polynucleotides encode the first solubility enhancer or the second solubility enhancer selected from the group consisting of: a thioredoxin domain Trx, small ubiquitin-related protein SUMO, glutathione-S transferase GST, maltose-binding protein MBP, N utilization substance A NusA, and seventeen kilodalton protein Skp.

20. The expression cassette of one or more of embodiments 17-19, wherein the one or more polynucleotides encode each of the first solubility enhancer and the second solubility enhancer comprising the thioredoxin domain Trx.

21. The expression cassette of one or more of embodiments 17-20, wherein the one or more polynucleotides comprise, consist essentially of, or consists of a sequence with at least 70, 72, 75, 80, 85, 90, 91, 92, 93, 94, 95, 96, 97, 98, 99, or 100% identity to SEQ ID NO: 52.

22. The expression cassette of one or more of embodiments 17-21, wherein the one or more the polynucleotide comprise, consist essentially of, or consists of a sequence with at least 70, 72, 75, 80, 85, 90, 91, 92, 93, 94, 95, 96, 97, 98, 99, or 100% identity to SEQ ID NO: 54.

23. The expression cassette of one or more of embodiments 17-22, wherein the one or more polynucleotides encode a DPNG linker.

24. The expression cassette of one or more of embodiments 16-23, wherein the one or more polynucleotides encode the target protease selected from the group consisting of: EC3.4.99 proteases, EC3.4.21.62 proteases, keratinases, serine proteases, alkaline proteases, metallo proteases, cysteine proteases, aspartate proteases, ATP-dependent proteases, and Subtilisin family proteases.

25. The expression cassette one or more of embodiments 16-24, wherein the one or more polynucleotides encode a target protease selected from the group consisting of: a Savinase, an alkaline protease Q6PNN5, and acid protease B8NLY9_PEPA_ASPEN.

26. The expression cassette of one or more of embodiments 16-25, wherein the one or more polynucleotides encode a savinase and comprising, consisting essentially of, or consisting of a sequence with at least 70, 72, 75, 80, 85, 90, 91, 92, 93, 94, 95, 96, 97, 98, 99, or 100% identity to SEQ ID NO: 7.

27. The expression cassette of one or embodiments 16-26, wherein the one or more polynucleotides encode an intein selected from the group consisted of: gp41-1, Cbu_DnaB, Mja_GF-6P, Mja_Hyp-1, Mja_IF2, Mja_Pol-1, Pab_CDC21-1, Pab_IF2-N, Pab_VMA, Pho_IF2, Pho_VMA, Rma_DnaB, Sru_DnaB, Tag_Pol-1_Tsp-TY-_Pol-1, Ter_RIR1-4, Tko_IF2, or Tth-HB27 DnaE-2 intein.

28. The expression cassette of embodiment 27, wherein the one or more polynucleotides encode a gp41-1 intein and comprise, consist essentially of, or consists of a sequence with at least 70, 72, 75, 80, 85, 90, 91, 92, 93, 94, 95, 96, 97, 98, 99, or 100% identity to SEQ ID NO: 10.

29. The expression cassette of embodiment 28, wherein the one or more polynucleotides encode an N-intein of the gp41-1 intein and comprise, consist essentially of, or consists of a sequence with at least 70, 72, 75, 80, 85, 90, 91, 92, 93, 94, 95, 96, 97, 98, 99, or 100% identity to SEQ ID NO: 12.

30. The expression cassette of claim 28, wherein the one or more polynucleotides encode a C-intein of the gp41-1 intein and comprise, consist essentially of, or consists of a sequence with at least 70, 72, 75, 80, 85, 90, 91, 92, 93, 94, 95, 96, 97, 98, 99, or 100% identity to SEQ ID NO: 13.

31. The expression cassette of any one or more embodiments 16-30, wherein the one or more polynucleotides encode the first precursor and comprise, consist essentially of, or consists of a sequence with at least 70, 72, 75, 80, 85, 90, 91, 92, 93, 94, 95, 96, 97, 98, 99, or 100% identity to SEQ ID: 3.

32. The expression cassette of any one or more embodiments 16-31, wherein the one or more polynucleotides encode the second precursor and comprise, consist essentially of, or consists of a sequence with at least 70, 72, 75, 80, 85, 90, 91, 92, 93, 94, 95, 96, 97, 98, 99, or 100% identity to SEQ ID NO: 4.

33. A composition comprising: a first precursor of an intein-modified protease and a second precursor of an intein-modified protease, the first precursor comprises an N-extein of a target protease fused to a solubility enhanced N-intein of a trans-splicing intein, and the carboxy terminus of the N-extein is fused to the amino terminus of the solubility enhanced N-intein; the second precursor comprises a solubility enhanced C-intein of the trans-splicing intein fused to a C-extein of the target protease, and the carboxy terminus of the solubility enhanced C-intein is fused to the amino terminus of the C-extein; and the first precursor is separated from the second precursor prior to trans-splicing; wherein the intein-modified protease has enhanced solubility and reduced activity compared to the target protease and the activity of the target protease is obtained upon trans-splicing of the intein-modified protease and fusion of the N-extein and the C-extein.

34. The composition of embodiment 33, wherein the solubility enhanced N-intein comprises an N-intein and a first solubility enhancer, and the carboxy terminus of the N-intein is fused to the first solubility enhancer by a first linker; and/or the solubility enhanced C-intein comprises a C-intein and a second solubility enhancer, and the second solubility enhancer is fused to the amino terminus of the C-intein by a second linker.

35. The composition of one or both of embodiments 33-34, wherein the first solubility enhancer or the second solubility enhancer is selected from the group consisting of: a thioredoxin domain Trx, small ubiquitin-related protein SUMO, glutathione-S transferase GST, maltose-binding protein MBP, N utilization substance A NusA, and seventeen kilodalton protein Skp.

36. The composition of one or more of embodiments 33-35, wherein each of the first solubility enhancer and the second solubility enhancer comprises the thioredoxin domain Trx.

37. The composition of one or more of embodiments 34-36, wherein the first solubility enhancer comprises, consists essentially of, or consists of an amino acid sequence with at least 70, 72, 75, 80, 85, 90, 91, 92, 93, 94, 95, 96, 97, 98, 99, or 100% identity to SEQ ID NO: 51; and/or the second solubility enhancer comprises, consists essentially of, or consists of an amino acid sequence with at least 90% identity to SEQ ID NO: 53.

38. The composition of one or more of embodiments 34-37, wherein the first linker or the second linker is a DPNG linker.

39. The composition of one or more of embodiments 33-38, wherein the target protease is an enzyme selected from the group consisting of: EC3.4.99 proteases, EC3.4.21.62 proteases, keratinases, serine proteases, alkaline proteases, acid proteases, metallo proteases, cysteine proteases, aspartate proteases, ATP-dependent proteases, Subtilisin family proteases, Savinase, alkaline protease Q6PNN5, and acid protease B8NLY9_PEPA_ASPEN.

40. The composition of one or more of embodiments 33-39, wherein the target protease comprises, consists essentially of, or consists of an amino acid sequence with at least 70, 72, 75, 80, 85, 90, 91, 92, 93, 94, 95, 96, 97, 98, 99, or 100% identity to a sequence selected from the group consisting of SEQ ID NOS: 6, 8, and 9.

41. The composition of one or more of embodiments 3-40, wherein the N-intein comprises, consists essentially of, or consists of an amino acid sequence with at least 70, 72, 75, 80, 85, 90, 91, 92, 93, 94, 95, 96, 97, 98, 99, or 100% identity a sequence selected from the group consisting of SEQ ID NOS: 14, 16, 18, 20, 22, 24, 26, 28, 30, 32, 34, 36, 38, 40, 42, 44, and 46, the C-intein comprises, consists essentially of, or consists of an amino acid sequence with at least 70, 72, 75, 80, 85, 90, 91, 92, 93, 94, 95, 96, 97, 98, 99, or 100% identity a sequence selected from the group consisting of SEQ ID NOS: 15, 17, 19, 21, 23, 25, 27, 29, 31, 33, 35, 37, 39, 41, 43, 45, and 47, and the N-intein and the C-intein together form a trans-splicing intein or a variant thereof selected from the group consisting of: gp41-1, Cbu_DnaB, Mja_GF-6P, Mja_Hyp-1, Mja_IF2, Mja_Pol-1, Pab_CDC21-1, Pab_IF2-N, Pab_VMA, Pho_IF2, Pho_VMA, Rma_DnaB, Sru_DnaB, Tag_Pol-1_Tsp-TY_Pol-1, Ter_RIR1-4, Tko_IF2, and Tth-HB27_DnaE-2.

42. The composition of one or more of embodiments 33-41, wherein the first precursor comprises, consists essentially of, or consists of an amino acid sequence with at least 70, 72, 75, 80, 85, 90, 91, 92, 93, 94, 95, 96, 97, 98, 99, or 100% identity to SEQ ID NO: 1; and/or the second precursor comprises, consists essentially of, or consists of an amino acid sequence with at least 70, 72, 75, 80, 85, 90, 91, 92, 93, 94, 95, 96, 97, 98, 99, or 100% identity to SEQ ID NO: 2.

43. A home care product comprising an intein-modified protease of one or more of embodiments 1-15 or the compositions of one or more of embodiments 33-42, and one or more effectors.

44. The home care product of embodiment 43, wherein the one or more effectors is capable of suppressing trans-splicing.

45. The home care product of embodiment 44, wherein the suppressing is reversible.

46. The home care product of one or more of embodiments 43-45, further comprising at least one agent selected from the group consisting of: a detergent, a soap, industrial cleaner, a soapless soap and dish washing liquid.

47. The home care product of one or more of embodiments 43-46, wherein the one or more effectors are selected from the group consisting of: sodium chloride, tetrasodium iminodisuccinate, disodium succinate, disodium tartrate, potassium lactate, potassium citrate, potassium chloride, sodium nicotinate, ammonium sulfate, ammonium nitrate, lithium citrate, sodium polyaspartate, sodium polyacrylate, tetraethylene glycol, polyethylene glycol, tetraglycol, propylene carbonate, mono propylene glycol, glycerol, and tomadol.

48. The home care product of one or more of embodiments 43-47 further comprising at least one ingredient selected from the group consisting of: water softeners, surfactants, bleach, enzymes, brighteners, fragrances, anionic surfactants, nonionic surfactants, builders to remove the hardness ions, antiredeposition agents, dye transfer inhibitors, soil release polymers, optical brighteners, enzyme stabilizers, viscosity control compounds, pH control compounds, soap and silicones to control excessive foaming, preservatives for microbial control, perfume and dye for scent and appearance, bleaching agents, water, solubilizers, alkylbenzenesulphonates, ethoxylated fatty alcohols, sodium citrate, tetrasodium EDTA or an acrylic polymer, PVP K-30, Chromabond S-100, Chromabond S-400, Sorez 100, Repel-O-Tex SRP-6, Tinopal CBS-X, calcium chloride, sodium tetraborate, propylene glycol, sodium formate, sodium citrate, monoethanolamine, propylene glycol, sodium xylene sulfonate, polymers, and citric acid.

49. The home care product of one or more of embodiments 43-48 further comprising a fuel additive selected from the group consisting of: a long-chain amine or amide, polyisobuteneamine, polyisobuteneamide and succinimide.

50. The home care product of one or more of embodiments 43-49 further comprising a biological reagent.

51. The home care product of any one or more of embodiments 43-50, wherein the one or more effectors are selected from the group consisting of: sodium chloride, tetrasodium iminodisuccinate, disodium succinate, disodium tartrate, potassium lactate, potassium citrate, potassium chloride, sodium nicotinate, ammonium sulfate, ammonium nitrate, lithium citrate, sodium polyaspartate, sodium polyacrylate, tetraethylene glycol, polyethylene glycol, tetraglycol, propylene carbonate, mono propylene glycol, glycerol, and tomadol.

52. A method of regulating protease activity comprising:
forming the home care product of any one or more of embodiments 43-51.

53. The method of embodiment 36, wherein forming comprises combining the composition of any one or more of embodiments 33-42 with one or more effectors.

54. The method of one or both of embodiments 52-53 comprising causing splicing of the intein-modified protease.

55. The method of one or more of embodiments 52-54, wherein the one or more effectors are selected from the group consisting of: sodium salt supplements, potassium salt supplements, ammonium salt supplements, charged polymeric salt supplements, and polyol supplements.

56. The methods of one or more of embodiments 52-55, wherein the one or more effectors are selected from the group consisting of: sodium chloride, tetrasodium iminodisuccinate, disodium succinate, disodium tartrate, potassium lactate, potassium citrate, potassium chloride, sodium nicotinate, ammonium sulfate, ammonium nitrate, lithium citrate, sodium polyaspartate, sodium polyacrylate, tetraethylene glycol, polyethylene glycol, tetraglycol, propylene carbonate, mono propylene glycol, glycerol, and tomadol.

57. The method of one or more of embodiments 52-56, wherein the one or more effectors comprises potassium chloride.

58. The method of embodiment 57, wherein the potassium chloride concentration is in a range from 0.1 M to 5.0 M.

59. The method of method of one or both of embodiments 57 or 58 wherein the potassium chloride concentration is in a range from 0.5 M to 2.0 M.

60. The method of one or more embodiments 54-59, wherein the step of causing splicing includes diluting the mixture with a liquid to a mixture:liquid ratio of less or equal to one selected from the group consisting of: 1:5, 1:10, 1:20, 1:50: 1:60, 1:70, 1:80, 1:90, 1:100, 1:150, 1:200, 1:250, 1:300, 1:350, and 1:400 of a mixture to liquid.

61. The method of embodiment 60, wherein the liquid is one of water and an aqueous buffer.

63. The method of one or more of embodiments 52-61, wherein the protease activity of the target protease is obtained upon splicing of the intein-modified protease.

64. A method of storing a protease in a mixture comprising: making an intein-modified protease of any one or more of embodiments 1-15, or the compositions of any one or more of embodiments 33-42, and combining the intein-modified protease or the composition with at least one agent selected from the group consisting of: detergent, a soap, an industrial cleaner, and a dishwashing liquid and one or more effectors to form a mixture.

Further embodiments herein may be formed by supplementing an embodiment with one or more element from any one or more other embodiment herein, and/or substituting one or more element from one embodiment with one or more element from one or more other embodiment herein.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Example 1. Trans-Splicing Intein Technology for Regulating Activity of Proteases Trans-splicing intein technology may be used regulate protease activity. In this approach the protease is split between catalytic residues to two inactive fragments, which are individually expressed as fusion to trans-splicing inteins. Mixing in an aqueous environment triggers trans-intein mediated association of inactive fragments, splicing and seamless joining of the inactive parts to fully functional active protease.

Construction, expression and detergent dilution inducible properties of a trans-splicing intein regulated liquid laundry protease, Savinase have been described in PCT patent application PCT/US2013/063304, which is incorporated herein by reference as if fully set forth. Methods that improve formulation stability and detergent dilution inducible protease activity to levels relevant in commercial liquid laundry application are described herein.

Example 2. Solubility Optimized Molecules

Detergent refers to liquid laundry detergents. Detergent-1 (MTS24 (Maradonal0)) and -4 (GRESINOL™) were enzyme-free, optical-brightener-free and coloring agent-free standard liquid detergent formulations. Detergent-1 could contain deionized water, Neodol 25_7, LAS acid, Prifac 5908, Dequest 2010, SLES 3EO, sodium sulfite, Sokalan HP20, MPG, MEA, TEA, glycerol, Tinopal 5BMGX and other common liquid laundry detergent components. Detergent-1 had a pH of ~8.3±0.2 and conductivity of ~3890 μSimens. Detergent-4 had a pH ~7.3±0.2 and conductivity of ~22400 μSimens.

Detergent-2 (SEVENTH GENERATION™), and -3 (MYERS™) were optical brightener and coloring agent free commercial brand detergents with formulated protease. Detergent-2 had a pH of ~8.8±0.2, and conductivity of ~3900 μSimens. Detergent-3 had a pH of ~8.3±0.2, and conductivity of ~7090 μSimens. Protease activity was inactivated by heat treatment at 80° C. for 90 min. After cooling to room temperature, the absence of protease was verified as follows: detergent was diluted to 50% v/v with deionized water. To 25 μL 50% detergent, 75 μL of BR buffer (40 mM sodium phosphate dibasic, 40 mM sodium acetate, 40 mM sodium borate were added, pH adjusted to 9.0 with NaOH), 100 μL of FAAF-pNA substrate (500 μM) was added, and absorbance was read at 400 nm in a kinetic assay at 37° C. Assay plates were sealed and inspected after overnight incubation at 37° C. for yellow color development indicative of protease activity. Heat treated detergent had no measurable protease activity. The unheated detergent showed robust and instant protease activity under the same conditions.

Savinase is an extracellular alkaline protease from *Bacillus lentus* (Uniprot accession number is: P29600 and a common protease in liquid laundry detergents. Examples herein utilize Savinase having the amino acid sequence of SEQ ID NO: 6.

Savinase Enzyme Assay

The substrate for the Savinase enzyme assay is the chromogenic peptide substrate N-Succinyl-Ala-Ala-Pro-Phe p-nitroanilide (Sigma-Aldrich). This substrate is highly specific for subtilisin-like enzymes (Davis et al., 1999) and it can support enzyme assays in bacterium suspensions (Bonifait et al., 2010, which is incorporated by reference herein as if fully set forth). In a typical assay, 100 μL of lysate, or bacterium suspension is added to 20 μl of the chromogenic substrate N-succinyl-Ala-Ala-Pro-Phe-pNa (2 mg/mL in 50% dimethyl formamide), the reaction mixture is incubated at 37° C. for variable times and the release of pNA is quantified by measuring the absorbance at 415 nm (Bonifait et al., 2010). This protocol is easily adaptable through automation to support screening by performing high throughput protease activity assays. Proteolytic activity can also be measured by digestion of AZO-casein (Vazquez et al. 2004). Twenty microliters of lysate are incubated in 384-well plate with 20 μL of 1% (w/v) AZO-casein in Tris-HCl buffer (0.1 M, pH8.0) and 0.5 mM CaCl2 at 55° C. for 30 min. After stopping the reaction with 40 μL of 5% (w/v) trichloracetic acid, reaction mixture is centrifuged and absorbance of supernatant was measured at 340 nm.

iSavinase refers to an intein-modified protease system, where the target protease is a Savinase. More generally, any intein-modified proteases system herein, including the iSavinase system, may be referred to as iProtease. Savinase molecules may be generated by trans-splicing of the intein-modified precursors. The intein-modified precursor molecule, which is expressed prior to intein splicing, is referred to as a "NI" (representing in frame fusion of the Savinase N-terminal fragment (N-extein) including the pro-domain and sequences ending with residue 316 (numbering based on preproSavinase) to the N-terminal part of the Gp41-1 intein ($I^N$), and IC (representing the fusion of Gp41-1 C-terminal intein ($I^C$) to the C-terminal part (C-extein) of Savinase starting with serine 317. The splice product that has the amino extein (N) and carboxy extein (C) seamlessly joined called "NC", which after auto-cleavage of the pro-domain results in the active enzyme, iProtease. "(NI+IC) premix" refers to a mix of splicing competent NI and IC in an inactive state that has no protease activity but can be induced by dilution to yield fully active iProtease.

NI and IC described herein are solubility optimized versions of the prototype molecule iProtease:S317-Gp41-1 NI and IC described in PCT/US2013/063304, which is incorporated herein by reference as if fully set forth.

The nucleotide sequence of the wild type gp41-1 split intein (length: 375 bp) with N-intein and C-intein parts fused is as follows. The C-intein part is in bold and underlined.

(SEQ ID NO: 10)
TGTCTGGACCTGAAAACGCAAGTGCAAACCCCGCAAGGCATGAAGGAAA

TCTCAAACATCCAAGTCGGTGACCTGGTGCTGTCGAATACCGGCTATAAC

GAAGTGCTGAATGTTTTTCCGAAGAGCAAAAAGAAATCTTACAAGATCAC

GCTGGAAGATGGCAAGGAAATTATTTGCAGCGAAGAACATCTGTTCCCGA

CCCAGACGGGCGAAATGAATATCTCCGGCGGTCTGAAAGAAGGCATGTG

TCTGTACGTCAAGGAAATGATGCTGAAGAAAATTCTGAAGATCGAAGA

ACTGGATGAACGTGAACTGATTGACATCGAAGTTAGCGGCAACCATC

TGTTTTACGCGAATGACATTCTGACCCACAAC

The protein sequence of the wild type gp41-1 split intein with fused N- and C-intein parts is as follows. The C-intein part is in bold and underlined.

```
                                                   (SEQ ID NO: 11)
CLDLKTQVQTPQGMKEISNIQVGDLVLSNTGYNEVLNVFPKSKKKSYKIT       50

LEDGKEIICSEEHLFPTQTGEMNISGGLKEGMCLYVKEMMLKKILKIEEL      100

DERELIDIEVSGNHLFYANDILTHN
```

The map of gp41-1 sequences is shown below:

```
  1 TGTCTGGACCTGAAAACGCAAGTGCAAACCCCGCAAGGCATGAAGGAAATCTCAAACATC  60
    C  L  D  L  K  T  Q  V  Q  T  P  Q  G  M  K  E  I  S  N  I

61 CAAGTCGGTGACCTGGTGCTGTCGAATACCGGCTATAACGAAGTGCTGAATGTTTTTCCG 120
    Q  V  G  D  L  V  L  S  N  T  G  Y  N  E  V  L  N  V  F  P

121 AAGAGCAAAAAGAAATCTTACAAGATCACGCTGGAAGATGGCAAGGAAATTATTTGCAGC 180
    K  S  K  K  K  S  K  I  T  T  L  E  D  G  K  E  I  I  C  S

181 GAAGAACATCTGTTCCCGACCCAGACGGGCGAAATGAATATCTCCGGCGGTCTGAAAGAA 240
    E  E  H  L  F  P  T  Q  T  G  E  M  N  I  S  G  G  L  K  E

241 GGCATGTGTCTGTACGTCAAGGAAATGATGCTGAAGAAAATTCTGAAGATCGAAGAACTG 300
    G  M  C  L  Y  V  K  E  M  M  L  K  K  I  L  K  I  E  E  L

301 GATGAACGTGAACTGATTGACATCGAAGTTAGCGGCAACCATCTGTTTTACGCGAATGAC 360
    D  E  R  E  L  I  D  I  E  V  S  G  N  H  L  F  Y  A  N  D

361 ATTCTGACCCACAAC                         375   (SEQ ID NO: 10)
    I  L  T  H  N                                (SEQ ID NO: 11)
```

In the 41-1 map, the N- and C-intein parts are fused and the C-intein part is in bold and underlined.

Molecular optimization for improved solubility were all restricted to the intein parts to ensure splicing leaves no footprint in the target enzyme when the intein removes itself and seamlessly joins the flanking protein sequences to restore intact protein backbone to full activity.

FIG. 1 shows schematic drawings of the solubility optimized molecules. Referring to FIG. 1, Savinase is split between catalytic residues to Sav-N and Sav-C. Catalytic residues are: D (Asp143), H (His172), S (Ser326), relative positions are marked by vertical lines. Intein parts $I^N$ and $I^C$ are attached to Savinase parts Sav-N and Sav-C, respectively. Solubility engineering is restricted to the intein parts. Solubility enhancer Trx domains are attached to each intein part via a DPNG (Asp-Pro-Asn-Gly (SEQ ID NO:5)) linker.

The C-intein part ($I^C$) has multiple mutations for enhanced solubility. These are M89Δ, L91T, L95T, L122G (numbering is by the position in the fused $I^N$+$I^C$).

Solubility optimized NI, termed NI-DPNG-Trx, has a C-terminal solubility enhancer thioredoxin domain (Trx, from pET32) fused via an Asp-Pro-Asn-Gly (DPNG) linker to the C-terminal end of the Gp41-1 N-intein ($I^N$) in the iProtease:S317-Gp41-1N. In the solubility optimized IC, termed Trx-DPNG-MTT IC[G122L], the thioredoxin domain (Trx) domain is fused via an Asp-Pro-Asn-Gly (DPNG) linker N-terminal to the mutated C-intein ($I^C$) of the iProtease:S317-Gp41-1C. The mutated C-intein, MTT-IC [L122G] has four solubility enhancer mutations at positions M89Δ, L91T, L95T and L122G (numbering is by the position in the fused $I^N$+$I^C$ of GP41-1).]

Nucleic acid sequences of solubility optimized iProtease NI (NI-DPNG-Trx)

```
                                                     (SEQ ID NO: 3)
  1 ATGGCTGAAG AAGCAAAAGA AAAATATTTA ATTGGCTTTA ATGAGCAGGA AGCTGTCAGT

61 GAGTTTGTAG AACAAGTAGA GGCAAATGAC GAGGTCGCCA TTCTCTCTGA GGAAGAGGAA

121 GTCGAAATTG AATTGCTTCA TGAATTTGAA ACGATTCCTG TTTTATCCGT TGAGTTAAGC

181 CCAGAAGATG TGGACGCGCT TGAACTCGAT CCAGCGATTT CTTATATTGA AGAGGATGCA

241 GAAGTAACGA CAATGGCGCA ATCGGTACCt TGGGGAATTA GCCGTGTGCA AGCCCCAGCT

301 GCCCATAACC GTGGATTGAC AGGTTCTGGT GTAAAAGTTG CTGTCCTCGA TACAGGGATA

361 TCCACTCATC CAGATCTAAA TATTCGTGGT GGCGCAAGCT TTGTACCAGG GAACCGTCG

421 ACTCAAGATG GAATGGGCA TGGCACGCAT GTGGCCGGGA CGATCGCTGC TTTAAACAAT

481 TCGATTGGCG TTCTTGGCGT AGCGCCGAGC GCTGAGCTAT ACGCTGTTAA AGTCCTAGGG

541 GCGAGCGGTT CAGGTTCGGT CAGCTCGATT GCCCAAGGAT TGGAATGGGC AGGGAACAAT

601 GGCATGCACG TTGCTAATTT GAGTTTAGGA AGCCCTTCGC CAAGTGCCAC ACTTGAGCAA

661 GCTGTTAATA GCGCGACTTC TAGAGGCGTT CTTGTTGTAG CGGCATCTGG GAACTCAGGT
```

-continued

```
 721 GCAGGCTCAA TCAGCTATCC GGCGCGCTAT GCGAACGCAA TGGCAGTCGG AGCTACTGAT

781 CAAAACAACA ACCGCGCTAG CTTTTCACAG TATGGCGCAG GCCTTGACAT TGTCGCACCC

841 GGGGTAAACG TGCAGAGCAC ATACCCAGGT TGTCTGGACC TGAAAACGCA AGTGCAAACC

901 CCGCAAGGCA TGAAGGAAAT CTCAAACATC CAAGTCGGTG ACCTGGTGCT GTCGAATACC

961 GGCTATAACG AAGTGCTGAA TGTTTTTCCG AAGAGCAAAA AGAAATCTTA CAAGATCACG

1021 CTGGAAGATG GCAAGGAAAT TATTTGCAGC GAAGAACATC TGTTCCCGAC CCAGACGGGC

1081 GAAATGAATA TCTCCGGCGG TCTGAAAGAA GGCATGTGTC TGTACGTCAA GGAAgatcct 1141 aatggtATGA GCGATAAAAT TATTCACCTG ACTGACGACA GTTTTGACAC GGATGTACTC

1201 AAAGCGGACG GGGCGATCCT CGTCGATTTC TGGGCAGAGT GGTGCGGTCC GTGCAAAATG

1261 ATCGCCCCGA TTCTGGATGA AATCGCTGAC GAATATCAGG GCAAACTGAC CGTTGCAAAA

1321 CTGAACATCG ATCAAAACCC TGGCACTGCG CCGAAATATG GCATCCGTGG TATCCCGACT

1381 CTGCTGCTGT TCAAAAACGG TGAAGTGGCG GCAACCAAAG TGGGTGCACT GTCTAAAGGT

1441 CAGTTGAAAG AGTTCCTCGA CGCTAACCTG GCCTAG
```

Amino acid sequences of the solubility optimized iProtease NI (NI-DPNG-Trx)

```
                                                              (SEQ ID NO: 1)
    MAEEAKEKYL IGFNEQEAVS EFVEQVEAND EVAILSEEEE VEIELLHEFE TIPVLSVELS

1 PEDVDALELD PAISYIEEDA EVTTMAQSVP WGISRVQAPA AHNRGLTGSG VKVAVLDTGI

121 STHPDLNIRG GASFVPGEPS TQDGNGHGTH VAGTIAALNN SIGVLGVAPS AELYAVKVLG

181 ASGSGSVSSI AQGLEWAGNN GMHVANLSLG SPSPSATLEQ AVNSATSRGV LVVAASGNSG

241 AGSISYPARY ANAMAVGATD QNNNRASFSQ YGAGLDIVAP GVNVQSTYPG CLDLKTQVQT

301 PQGMKEISNI QVGDLVLSNT GYNEVLNVFP KSKKKSYKIT LEDGKEIICS EEHLFPTQTG

361 EMNISGGLKE GMCLYVKEDP NGMSDKIIHL TDDSFDTDVL KADGAILVDF WAEWCGPCKM

421 IAPILDEIAD EYQGKLTVAK LNIDQNPGTA PKYGIRGIPT LLLFKNGEVA ATKVGALSKG

481 QLKEFLDANL A*
```

Nucleic acid sequences of the solubility optimized iProtease IC (Trx-DPNG-MTT-IC)

```
                                                              (SEQ ID NO: 4)
  1 ATGAGCGATA AAATTATTCA CCTGACTGAC GACAGTTTTG ACACGGATGT ACTCAAAGCG

61 GACGGGGCGA TCCTCGTCGA TTTCTGGGCA GAGTGGTGCG GTCCGTGCAA AATGATCGCC

121 CCGATTCTGG ATGAAATCGC TGACGAATAT CAGGGCAAAC TGACCGTTGC AAAACTGAAC

181 ATCGATCAAA ACCCTGGCAC TGCGCCGAAA TATGGCATCC GTGGTATCCC GACTCTGCTG

241 CTGTTCAAAA ACGGTGAAGT GGCGGCAACC AAAGTGGGTG CACTGTCTAA AGGTCAGTTG

301 AAAGAGTTCC TCGACGCTAA CCTGGCCgat cctaatggtA TGacGAAGAA AATTacGAAG

361 ATCGAAGAAC TGGATGAACT GAACTGATT GACATCGAAG TTAGCGGCAA CCATCTGTTT

421 TACGCGAATG ACATTggGAC CCACAACTCA ActTATGCCA GCTTAAACGG TACATCGATG

481 GCTACTCCTC ATGTTGCAGG TGCGGCCGCC CTTGTTAAAC AAAAGAACCC ATCTTGGTCT
```

```
541 AATGTACAAA TTCGAAATCA TCTAAAGAAT ACGGCAACTA GTTTAGGAAG CACGAACTTG

601 TATGGAAGCG GACTTGTTAA CGCAGAAGCG GCAACGCGTT AA
```

Amino acid sequences of the solubility optimized iProtease IC (Trx-DPNG-MTT-IC)

(SEQ ID NO: 2)

```
  1 MSDKIIHLTD DSFDTDVLKA DGAILVDFWA EWCGPCKMIA PILDEIADEY QGKLTVAKLN

61 IDQNPGTAPK YGIRGIPTLL LFKNGEVAAT KVGALSKGQL KEFLDANLAD PNGMTKKITK

121 IEELDERELI DIEVSGNHLF YANDIGTHNS TYASLNGTSM ATPHVAGAAA LVKQKNPSWS

181 NVQIRNHLKN TATSLGSTNL YGSGLVNAEA ATR
```

Map of iProtease NI is as follows:

```
  1 M   A   E   E   A   K   E   K   Y   L   I   G   F   N   E   Q   E   A   V   S
  1 ATGGCTGAAGAAGCAAAAGAAAAATATTTAATTGGCTTTAATGAGCAGGAAGCTGTCAGT

21 E   F   V   E   Q   V   E   A   N   D   E   V   A   I   L   S   E   E   E   E
 61 GAGTTTGTAGAACAAGTAGAGGCAAATGACGAGGTCGCCATTCTCTCTGAGGAAGAGGAA

41 V   E   I   E   L   L   H   E   F   E   T   I   P   V   L   S   V   E   L   S
121 GTCGAAATTGAATTGCTTCATGAATTTGAAACGATTCCTGTTTTATCCGTTGAGTTAAGC

61 P   E   D   V   D   A   L   E   L   D   P   A   I   S   Y   I   E   E   D   A
181 CCAGAAGATGTGGACGCGCTTGAACTCGATCCAGCGATTTCTTATATTGAAGAGGATGCA

81 E   V   T   T   M   A   Q   S   V   P   W   G   I   S   R   V   Q   A   P   A
241 GAAGTAACGACAATGGCGCAATCGGTACCtTGGGGAATTAGCCGTGTGCAAGCCCCAGCT

101 A   H   N   R   G   L   T   G   S   G   V   K   V   A   V   L   D   T   G   I
301 GCCCATAACCGTGGATTGACAGGTTCTGGTGTAAAAGTTGCTGTCCTCGATACAGGGATA

121 S   T   H   P   D   L   N   I   R   G   G   A   S   F   V   P   G   E   P   S
361 TCCACTCATCCAGATCTAAATATTCGTGGTGGCGCAAGCTTTGTACCAGGGGAACCGTCG

141 T   Q   D   G   N   H   G   T   H   V   A   G   T   I   A   A   L   N   N
421 ACTCAAGATGGGAATGGGCATGGCACGCATGTGGCCGGGACGATCGCTGCTTTAAACAAT

161 S   I   G   V   L   G   V   A   P   S   A   E   L   Y   A   V   K   V   L   G
481 TCGATTGGCGTTCTTGGCGTAGCGCCGAGCGCTGAGCTATACGCTGTTAAAGTCCTAGGG

181 A   S   G   S   G   S   V   S   S   I   A   Q   G   L   E   W   A   G   N   N
541 GCGAGCGGTTCAGGTTCGGTCAGCTCGATTGCCCAAGGATTGGAATGGGCAGGGAACAAT

201 G   M   H   V   A   N   L   S   L   G   S   P   S   P   S   A   T   L   E   Q
601 GGCATGCACGTTGCTAATTTGAGTTTAGGAAGCCCTTCGCCAAGTGCCACACTTGAGCAA

221 A   V   N   S   A   T   S   R   G   V   L   V   V   A   A   S   G   N   S   G
661 GCTGTTAATAGCGCGACTTCTAGAGGCGTTCTTGTTGTAGCGGCATCTGGGAACTCAGGT

241 A   G   S   I   S   Y   P   A   R   Y   A   N   A   M   A   V   G   A   T   D
721 GCAGGCTCAATCAGCTATCCGGCGCGCTATGCGAACGCAATGGCAGTCGGAGCTACTGAT

261 Q   N   N   N   R   A   S   F   S   Q   Y   G   A   G   L   D   I   V   A   P
781 CAAAACAACAACCGCGCTAGCTTTTCACAGTATGGCGCAGGCCTTGACATTGTCGCACCC

281 G   V   N   V   Q   S   T   Y   P   G   C   L   D   L   K   T   Q   V   Q   T
841 GGGGTAAACGTGCAGAGCACATACCCAGGTTGTCTGGACCTGAAAACGCAAGTGCAAACC

301 P   Q   G   M   K   E   I   S   N   I   Q   V   G   D   L   V   L   S   N   T
901 CCGCAAGGCATGAAGGAAATCTCAAACATCCAAGTCGGTGACCTGGTGCTGTCGAATACC

321 G   Y   N   E   V   L   N   V   F   P   K   S   K   K   K   S   Y   K   I   T
961 GGCTATAACGAAGTGCTGAATGTTTTTCCGAAGAGCAAAAAGAAATCTTACAAGATCACG

341 L   E   D   G   K   E   I   I   C   S   E   E   H   L   F   P   T   Q   T   G
1021 CTGGAAGATGGCAAGGAAATTATTTGCAGCGAAGAACATCTGTTCCCGACCCAGACGGGC
```

```
361 E   M   N   I   S   G   G   L   K   E   G   M   C   L   Y   V   K   E   D   P
1081 GAAATGAATATCTCCGGCGGTCTGAAAGAAGGCATGTGTCTGTACGTCAAGGAAgatcct 381 N   G   M   S   D   K   I   I   H   L   T   D   D   S   F   D   T   D   V   L
1141 aatggtATGAGCGATAAAATTATTCACCTGACTGACGACAGTTTTGACACGGATGTACTC 401 K   A   D   G   A   I   L   V   D   F   W   A   E   W   C   G   P   C   K   M
1201 AAAGCGGACGGGGCGATCCTCGTCGATTTCTGGGCAGAGTGGTGCGGTCCGTGCAAAATG 421 I   A   P   I   L   D   E   I   A   D   E   Y   Q   G   K   L   T   V   A   K
1261 ATCGCCCCGATTCTGGATGAAATCGCTGACGAATATCAGGGCAAACTGACCGTTGCAAAA 441 L   N   I   D   Q   N   P   G   T   A   P   K   Y   G   I   R   G   I   P   T
1321 CTGAACATCGATCAAAACCCTGGCACTGCGCCGAAATATGGCATCCGTGGTATCCCGACT 461 L   L   F   K   N   G   E   V   A   A   T   K   V   G   A   L   S   K   G
1381 CTGCTGCTGTTCAAAAACGGTGAAGTGGCGGCAACCAAAGTGGGTGCACTGTCTAAAGG 481 Q   L   K   E   F   L   D   A   N   L   A   *  (SEQ ID NO: 1)
1441 CAGTTGAAAGAGTTCCTCGACGCTAACCTGGCCTAG (SEQ ID NO: 3)
```

In the map of iProtease NI, proProteaseS317 is the proProtease N-terminal part: 27 aa residue secretion signal of the pre-proProtease is removed; first methionine is added to the N-terminus; and proProtease aa residues are residues 28 to 316 (pre-proProtease numbering). GLFS-N is the N-intein. DPNG is asp-pro-asn-gly (SEQ ID NO: 5) linker between GLFS-N N-intein and Trx, and is shaded. Trx is the solubility enhancer thioredoxin domain from pET32 and is shown in bold letters.

Map of iProtease IC is as follows:

```
 1 M   S   D   K   I   I   H   L   T   D   D   S   F   D   T   D   V   L   K   A
 1 ATGAGCGATAAAATTATTCACCTGACTGACGACAGTTTTGACACGGATGTACTCAAAGCG

21 D   G   A   I   L   V   D   F   W   A   E   W   C   G   P   C   K   M   I   A
61 GACGGGGCGATCCTCGTCGATTTCTGGGCAGAGTGGTGCGGTCCGTGCAAAATGATCGCC

41 P   I   L   D   E   I   A   D   E   Y   Q   G   K   L   T   V   A   K   L   N
121 CCGATTCTGGATGAAATCGCTGACGAATATCAGGGCAAACTGACCGTTGCAAAACTGAAC

61 I   D   Q   N   P   G   T   A   P   K   Y   G   I   R   G   I   P   T   L   L
181 ATCGATCAAAACCCTGGCACTGCGCCGAAATATGGCATCCGTGGTATCCCGACTCTGCTG

81 L   F   K   N   G   E   V   A   A   A   T   V   G   A   L   S   K   G   Q   L
241 CTGTTCAAAAACGGTGAAGTGGCGGCAACCAAAGTGGGTGCACTGTCTAAAGGTCAGTTG

101 K   E   F   D   A   N   N   L   A   D   P   N   G   M   T   K   I   T   T   K
301 AAAGAGTTCCTCGACGCTAACCTGGCCgatcctaatggtATGacGAAGAAAATTacGAAG 121 I   E   E   L   D   E   R   E   L   I   D   I   E   V   S   G   N   H   L   F
361 ATCGAAGAACTGGATGAACGTGAACTGATTGACATCGAAGTTAGCGGCAACCATCTGTTT 141 Y   A   N   D   I   G   T   H   N   S   T   Y   A   S   L   N   G   T   S   M
421 TACGCGAATGACATTggGACCCACAACTCAACtTATGCCAGCTTAAACGGTACATCGATG 161 A   T   P   H   V   A   G   A   A   A   L   V   K   Q   K   N   P   S   W   S
481 GCTACTCCTCATGTTGCAGGTGCGGCCGCCCTTGTTAAACAAAAGAACCCATCTTGGTCT 181 N   V   Q   I   R   N   H   L   K   N   T   A   T   S   L   G   S   T   N   L
541 AATGTACAAATTCGAAATCATCTAAAGAATACGGCAACTAGTTTAGGAAGCACGAACTTG 201 Y   G   S   G   L   V   N   A   E   A   A   T   R   *  (SEQ ID NO: 2)
601 TATGGAAGCGGACTTGTTAACGCAGAAGCGGCAACGCGTTAA (SEQ ID NO: 4)
```

In the map of iProtease IC, Trx is the solubility enhancer thioredoxin domain from pET32, and is shown in bold letters. DPNG is asp-pro-asn-gly (SEQ ID NO: 5) linker between Trx and GLFS C-intein and is shaded gray. GLFS-C [M89Δ, L91T, L95T, L122G] is the "MTT" variant of the GLFS C-intein and is underlined. S317Protease is the proProtease C-terminal fragment starting at serine 317 (S317).

Example 3. Expression of Solubility Optimized NI and IC in E. coli

For expression in *E. coli*, nucleotide sequences of the solubility optimized NI and IC were cloned into the pET Duet1 (Novagen) expression vector downstream to the IPTG inducible T7 promoter. NI-DPNG-Trx was cloned between the NcoI and PstI sites, Trx-DPNG-MTT-IC[L122G] was cloned between the NdeI and KpnI sites. Plasmids were introduced into the *E. coli* strain BL21 Gold (DE3) (Invitrogen).

To express the proteins, overnight starter cultures grown in LB+Carbenicillin (100 mg/L) at 30° C. at 300 rpm were diluted 40-fold into fresh LB+Carb 100 mg/L, incubated further at 30° C. at 300 rpm. When cultures reached $OD_{600}$ 0.6, IPTG was added to a final conc. of 0.5 mg/L to induce expression and the t=0 time point samples were harvested.

Aliquots (2 mL) were taken thereof at t=1.5, 3.0, 6.0 and 22.0 hrs. Cell were pelleted and lysed in 200 µL lysis buffer at 30° C., 300 rpm for 1 hour and lysates were split to two aliquots. Lysis buffer was 1:9 mix of [10× Fastbreak:mTSB buffer (150 mM NaCl, 50 mM Trisbase, 2 mM $CaCl_2$, pH=7.5, 1 mM DTT)]+0.2 µL/mL Benzonase (Novagen). To determine the total protein profile, to 20 µL cell lysate 20 µL 2×SDS loading dye+5% βME was added, samples were heated at 95° C. for 5 min and a 5 µL aliquot was separated on 12% SDS/PAGE, and gels were Coomassie stained. To determine the soluble protein profile, lysates were spinned at 5000 g for 5 min in a microfuge, the supernatant soluble fractions were harvested and a 20 µL aliquot was treated as above.

Figures 2A, 2B:
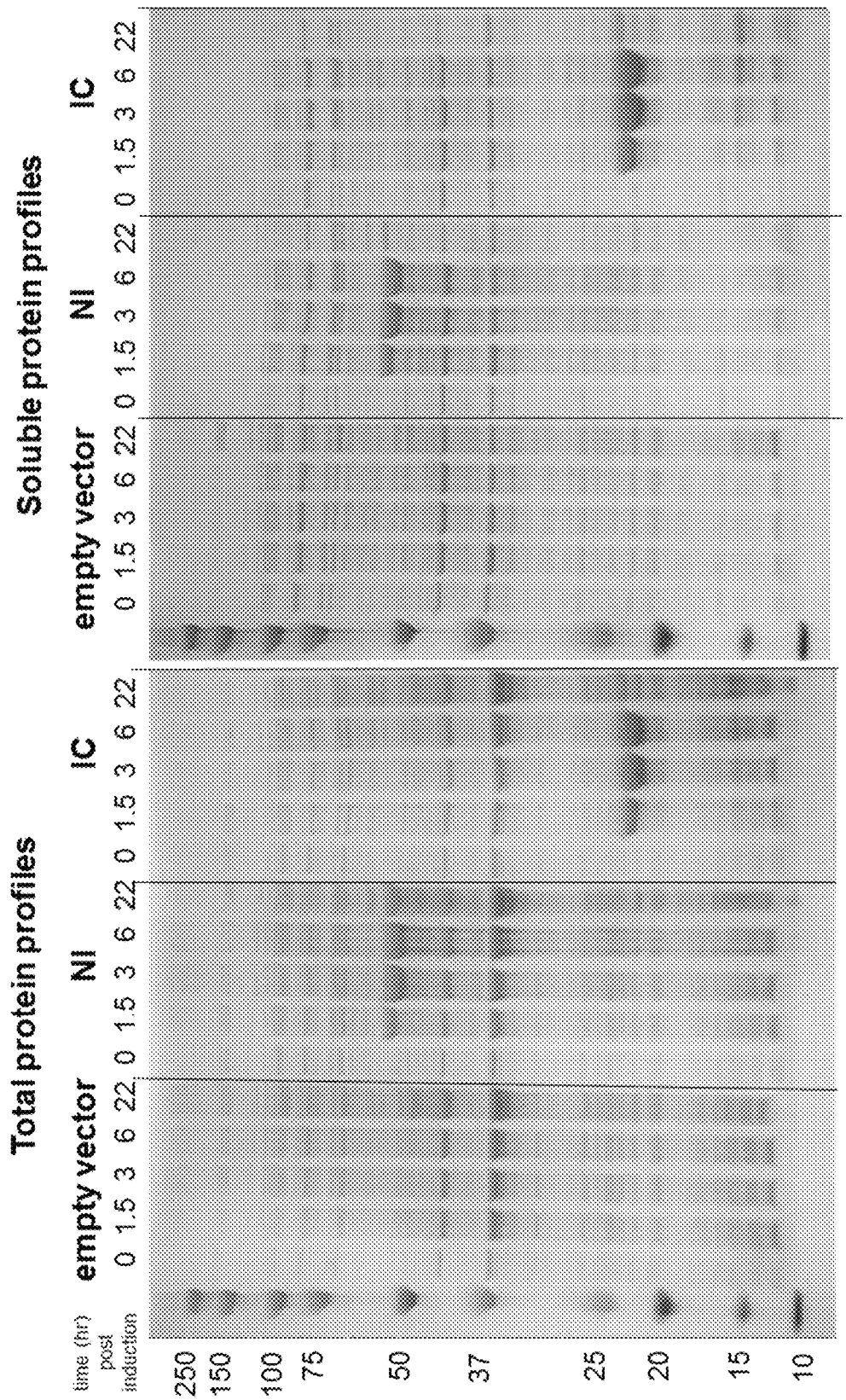
FIGS. 2A-2B illustrate expression of solubility optimized NI (SEQ ID NO: 1) and IC (SEQ ID NO: 2) (intein-modified precursors of iSavinase) in *E. coli*.

Most of the target proteins were produced during the first three hours of the induction in a time course typical to IPTG induced T7 promoter driven expression of recombinant proteins. Proteins expressed to comparable levels and predominantly accumulated to the soluble fraction. FIGS. 2A-2B illustrate expression of solubility optimized NI and IC in E. coli. FIG. 2A illustrates total protein profiles. FIG. 2B illustrates soluble protein profiles. In particular, FIG. 2B illustrates E. coli expression of solubility optimized NI and IC. Referring to FIGS. 2A-2B, expression was from the IPTG inducible T7 promoter of the pET Duet1 in E. coli BL21 Gold (DE3). Overnight cultures were diluted 40-fold into fresh LB+ Carbenicillin (100 mg/L) and grown at 30° C., 300 rpm to OD 0.6. IPTG was added to a final conc of 0.5 mg/L to induce expression and aliquots were taken at t=0, 1.5, 3.0, 6.0 and 22.0 hrs. Cells were harvested, lysed in $\frac{1}{10}^{th}$ culture volume of lysis buffer at 30° C., 300 rpm, 1 hr. Referring to FIG. 2A, to determine total protein profile the crude lysates were mixed with equal volume of 2×SDS loading dye+5% µME, heated at 95° C. for 5 min and 5 µL was separated on 12% SDS/PAGE and gels were Coomassie stained. Referring to FIG. 2B, to determine soluble protein profiles the crude lysates were clarified at 5000 g/5 min and the supernatant fraction was handled as above. It was observed that NI and IC predominantly expressed to the soluble fraction.

Example 4. Screening for Effectors of Dilution Induced iProtease Activity

The objective was to develop a liquid laundry detergent protease that can be stored in stable inactive state in the formulation and activated by dilution to water at the beginning of the wash cycle. The proof of concept demonstrated that Savinase can be split to two parts and expressed as intein modified inactive parts, and formulated them in liquid laundry detergent to restore activity by dilution into water. However, several challenges remained for the trans-splicing protease to meet application relevance, primarily in the robustness of dilution response to recover more than 80% activity (based on equal molar loadings with the intein unmodified enzyme), and in detergent storage stability in the induction competent state.

A major technical challenge was that while trans-splicing is a bimolecular, association driven and concentration dependent reaction, the application requires 400-fold dilution for induction that could counteract with post-dilution association of NI and IC for splicing. In addition for the trans-splicing to be robust, dilution induced splicing is expected to be fast and yield protease activity within minutes to be relevant for laundry detergent application. These requirements could be difficult to achieve by dilution when NI and IC are separate in the detergent, but conceivably could be better satisfied when the trans-splicing-parts are pre-associated but prevented from splicing.

Trans-splicing essentially progresses with the same mechanism as splicing (Perler FB, 2005), major difference is requirement for association of the intein parts. One possibility to associate trans-splicing precursors but prevent progression to splicing is to use splicing inhibitors, like $Zn^{++}$, $Cu^{++}$ or cistatin, that act in the post association step at the initiation of splicing (Nichols N M. et al, 2003; Sun P. et al, 2005: Zhang L. et al, 210; Zhang L. et al, 2011, all of which are incorporated by reference herein as if fully set forth). Although these inhibitors could satisfy requirement for controlled, dilution inducible splicing, they are not compatible with home use applications.

As an alternative, it was observed that the Detergent-1 suppressed iProtease activity in the formulations of NI and IC, but did not suppress activity of the intein unmodified Savinase suggesting that trans-splicing might be inhibited in the detergent. Modern liquid laundry detergents are complex formulations of a variety of ingredients including one or more ionic and nonionic surfactants, inorganic salts, electrolytes and adjuvants such as brighteners, perfumes and colorants and other compounds dispersed or dissolved in an aqueous medium that typically form structured liquids which could interact with formulated proteins in unpredictable ways. Inhibition may be the property of structured liquid or individual detergent components may also have suppression properties.

The effect of electrolytes on surface charge of proteins, and its isoelectric point, can be different in the presence of small electrolytes and for polymeric electrolytes Lyklema J, 2009; Martin-Molina A. et al., 2003; Besteman K., et al. 2004, all of which are incorporated by reference herein as if fully set forth). As opposed to monovalent salts, ion adsorption by polymeric ions by counterion interaction can even lead to effects such as charge inversion, and variance between isoelectric points measured via electrophoretic mobility, and the point of zero-surface charge (Besteman K. et al., 2004; Trulsson M. et al., 2006, all of which are incorporated by reference herein as if fully set forth).

Salts with monovalent ions were investigated, but also salts with large polyvalent/multivalent ions as detergent supplements for effecting dilution inducible iProtease activity of detergent formulated NI and IC, using detergent suppression and dilution induction assays. Detergent suppression measures activity of formulated NI and IC to yield iProtease in the detergent, dilution induction addresses the question whether suppression is reversible. To improve assay sensitivity, Detergent-2 have been selected. This detergent was compatible with NI and IC formulation, but had lower viscosity and showed lower detergent suppression activity than the Detergent-1. Supplements were selected for detergent compatibility and were industrial quality low cost chemicals. Concentrations were arbitrarily selected to be compatible with detergent formulation. The Detergent-2 was diluted to 50% (v/v) with deionized water with supplements to 2× concentration and no supplement in the control. 25 µL NI and 25 µL IC were then sequentially mixed to the detergents, and samples were exposed to suppression conditions overnight at 20° C. Samples were either diluted 20-fold to the corresponding detergent+supplement (detergent suppression assay) or diluted 20-fold to deionized water (dilution induction assay).

Figure 3A:
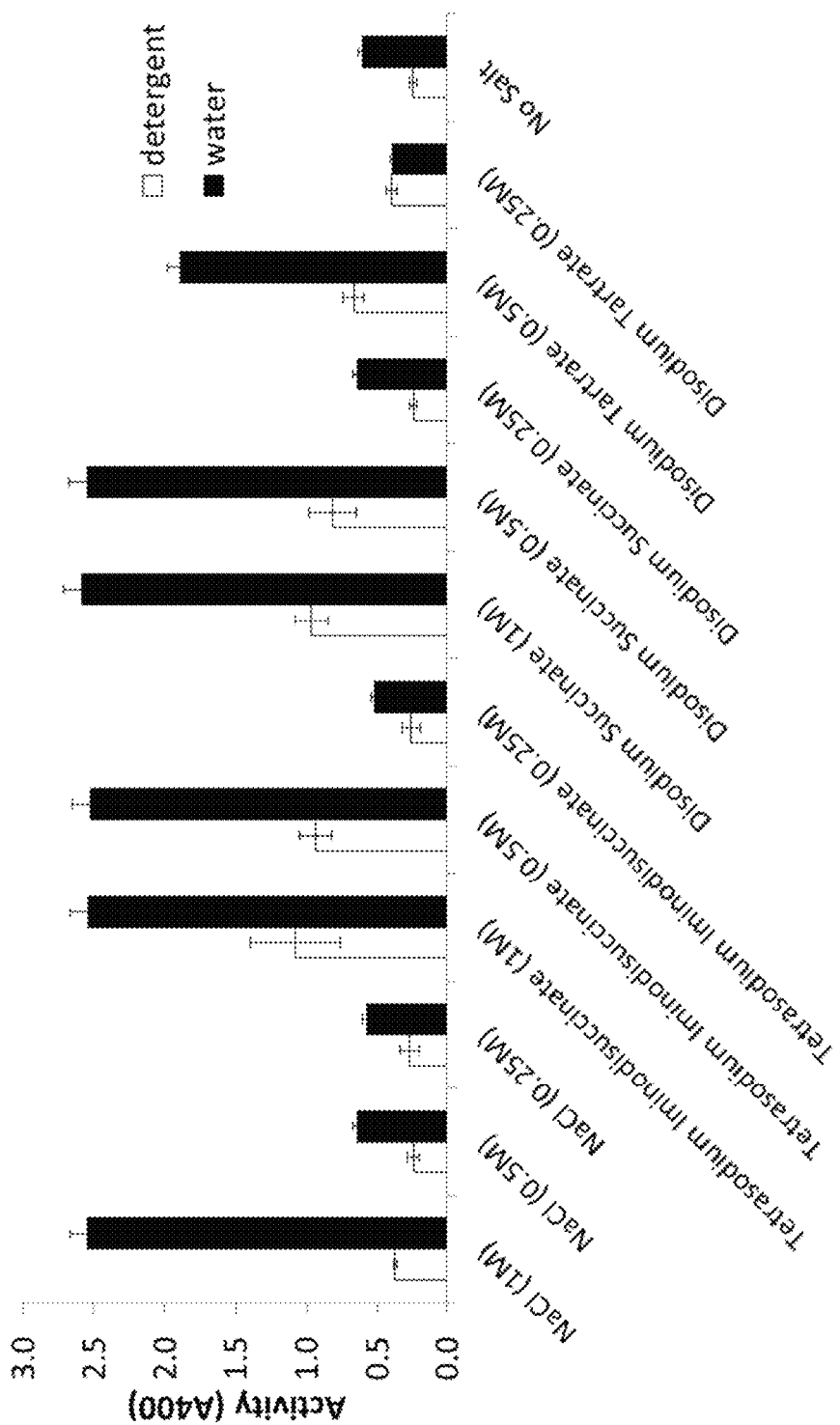
FIGS. 3A-3E illustrate results of detergent supplement screenings for dilution inducible iProtease (iSavinase; NI (SEQ ID NO: 1) and IC (SEQ ID NO: 2)) activity determined for sodium salt supplements (FIG. 3A), for potassium salt supplements (FIG. 3B), for ammonium and lithium salt supplements, (FIG. 3C), for charged polymeric salt supplements (FIG. 3D), and for polyol supplements (FIG. 3E).
Figure 3B:
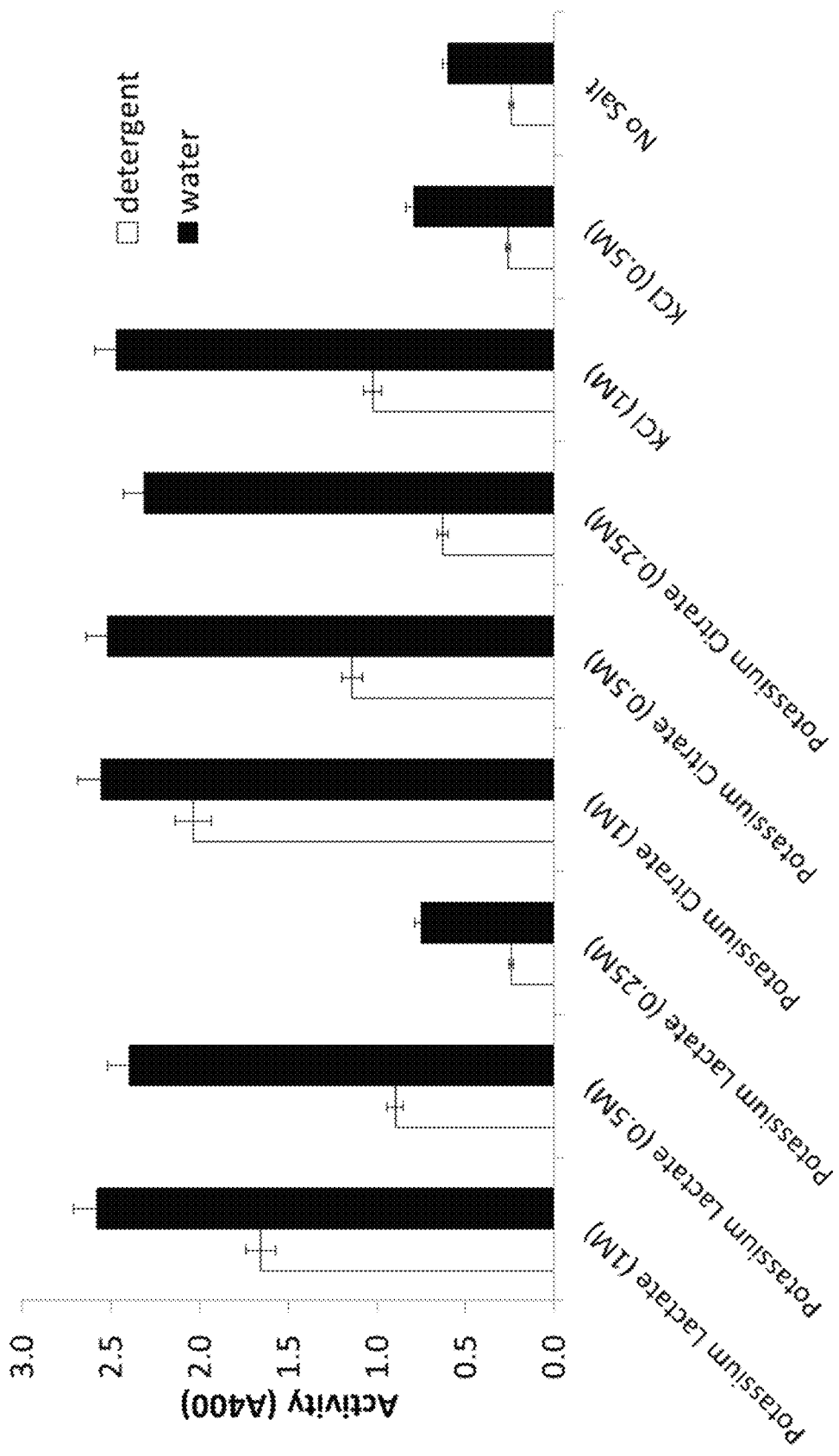
Figure 3C:
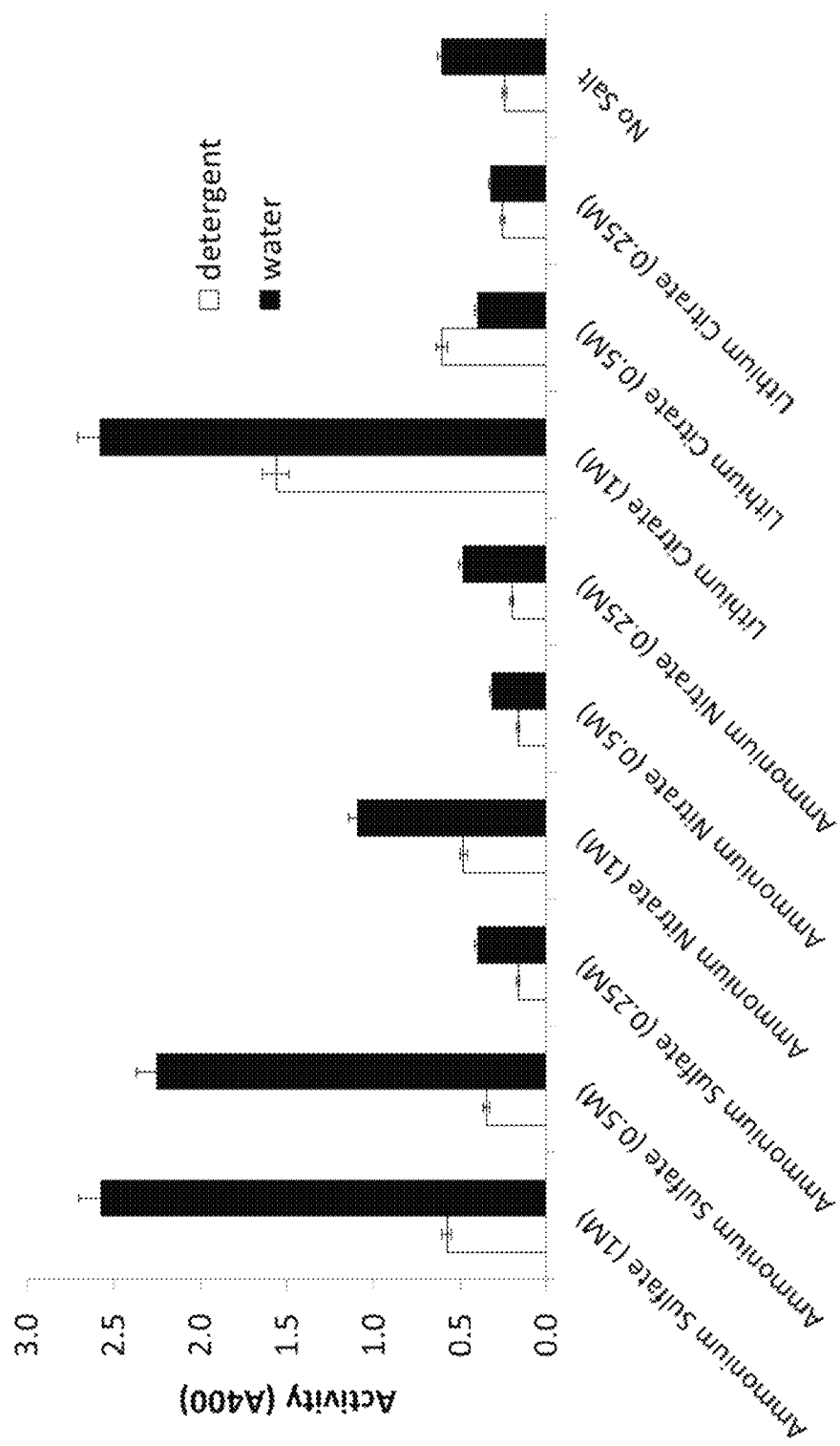
Figure 3D:
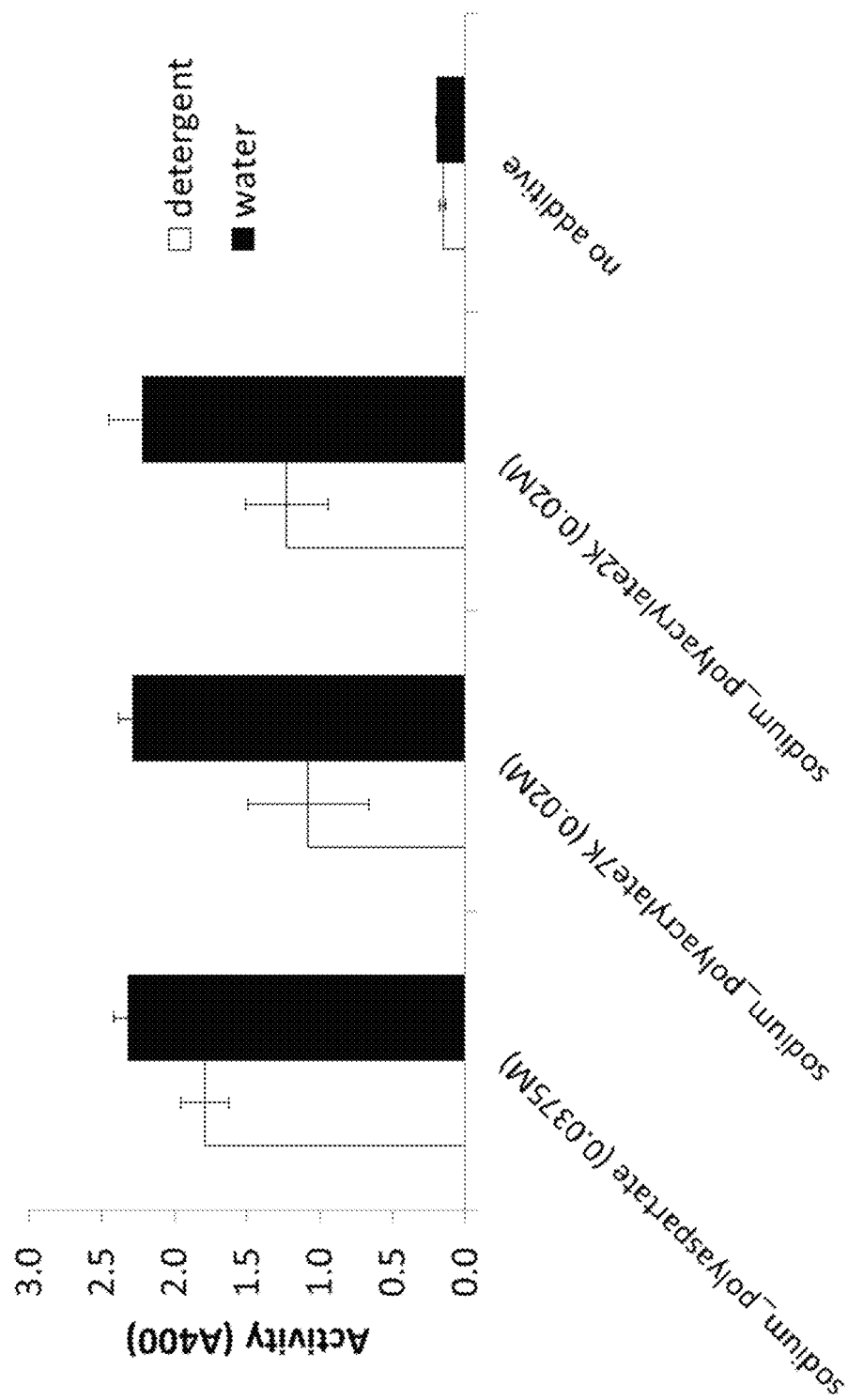
Figure 3E:
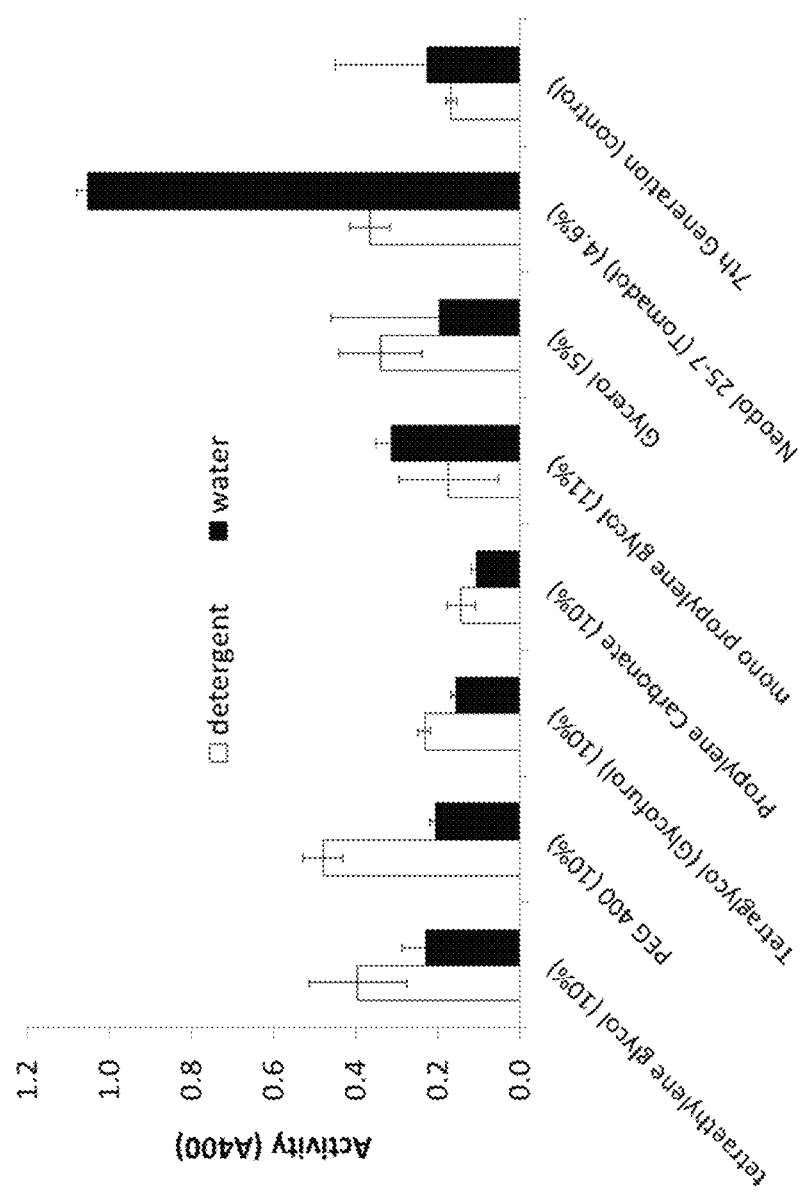

FIGS. 3A-3E illustrate effects of electrolytes and polyols on the detergent suppression and dilution induced activity of formulated trans-splicing NI and IC. Referring to these figures, supplements tested were as follows: sodium salt supplements (FIG. 3A), potassium salt supplements (FIG. 3B), ammonium salt supplements (FIG. 3C), charged polymeric salt supplements (FIG. 3D) and polyol supplements (FIG. 3E). The Detergent-2 was diluted to 50% (v/v) with deionized water and supplements were added to 2× concentration (e.g., 2M for 1M test). NI and IC were expressed in E. coli and clarified crude extracts were prepared as described in FIGS. 2A-2B. 25 μL NI and 25 μL, IC were then sequentially mixed to the supplemented detergents, or to detergent without the supplement in the controls, and formulations were incubated to expose the samples to suppression conditions overnight at 20° C. In the detergent suppression assay, samples were diluted 20× to detergent with 2× supplement, except that control which was diluted 20× to detergent without supplement. In the dilution induction assay, 20× dilutions were made to deionized water. Protease activity was determined in three replicate samples, by mixing 100 μL of the diluted sample with 100 μl of FAAF-pNA substrate (500 μM) and absorbance was read at 400 nm in a kinetic assay for 60 min (FIG. 3E, Polyol supplements) or until absorbance in the highest activity sample reached near the maximum of the linear range of the assay at ~2.8, and activities in detergent and water were graphed as shown in FIGS. 3A-3E.

A variety of salts, including alkali metals (lithium, sodium, potassium), ammonium with various counter ions including chloride, sulphate, nitrate, tartarate, succinate, disuccinate, iminodisuccinate, lactate, citrate, polyaspartate, polyacrylate increased iProtease activity upon dilution of the detergent formulated NI and IC to water. When dosed at different concentrations, the higher doses normally resulted in higher activity.

Polymeric salts that have more positive charge on a molar basis turned out to be potent enhancers of dilution inducible iProtease activity at a much lower concentration (0.02-0.0375M) than the monovalent salts (>0.25M). Sodium polyacrylate 7K (average MW 7300), and polyacrylate 2K (average MW 2100), carried, respectively about 100 and 30 sodium counter ions per molecule of polymer. Sodium polyaspartate, similarly carried about 35 of the sodium cations per molecule of polymer.

Electrolytes and polyelectrolytes listed, are non-limiting examples of chemicals that could possibly be suitable to control activity of detergent formulated NI and IC. Polyols, such as Neodol 25-7 represents yet another class of potential additives with similar properties.

Modern fabric detergents are concentrated structured liquids. Selection of a supplement for such a formulation would satisfy multiple criteria, such as suppression of activity of intein modified proteins in the undiluted concentrate, enhancement of enzyme activity upon dilution from intein modified parts, compatibility with the liquid formulation, fit-to-purpose as part of a household consumer product, including cost criteria.

Conceivably, supplements that may affect overall charge, charge distribution, hydration properties of the formulated trans-splicing proteins and/or alter protein association and crowding by other means in the detergent could have an effect on dilution inducible iProtease activity of the formulated trans-splicing NI and IC.

Detergent suppression and dilution induction assays described here enable quick screening for such effectors and could support formulation development for activity control of the intein modified proteins.

Example 5. Testing Effectors of Dilution Inducible iProtease Activity

Effectors Perform Similarly in Different Detergent Context

Figure 4A:
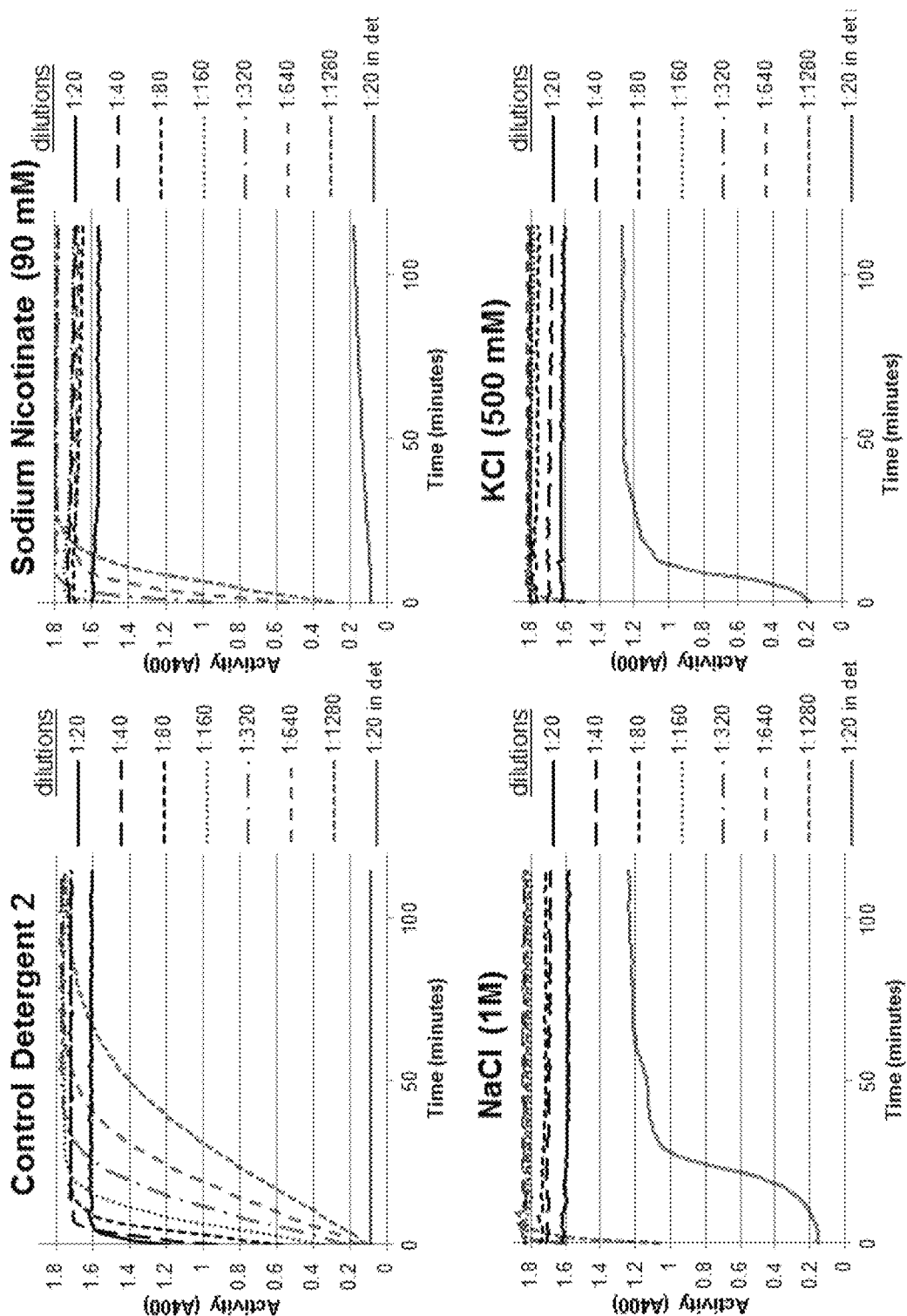
FIGS. 4A-4B illustrate the dilution inducible iSavinase (NI (SEQ ID NO: 1) and IC (SEQ ID NO: 2)) activities in detergents supplemented either with sodium nicotinate (90 mM), NaCl (1M) or KCl (500 mM). It was observed that salt supplements perform similarly in different detergent contexts: the Detergent-2 (FIG. 4A) and the Detergent-1 (FIG. 4B).
Figure 4B:
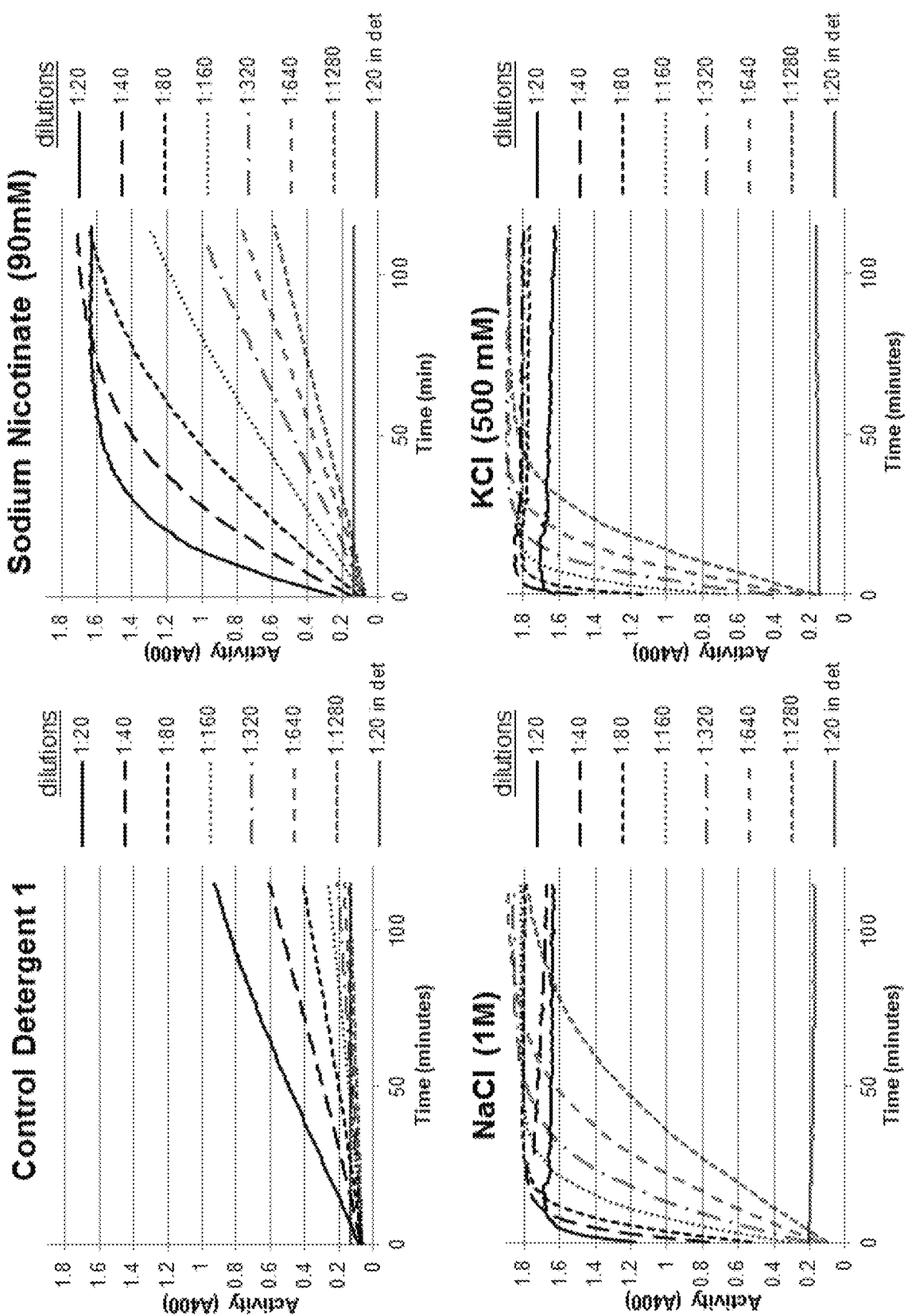

Supplements identified in the effector screen for activity enhancing effects in the in the Detergent-2 were found to perform similarly in the Detergent-1. FIGS. 4A-4B illustrate that effectors perform similarly in different detergent context. In particular, these figures compare dilution induction properties of three small molecule effectors, sodium nicotinate (90 mM), NaCl (1M) and KCl (500 mM) in the two detergents in quantitative protease assays. Assays were essentially the same as in the screen, but instead of cell lysates, purified proteins were used and activity was determined in a series of two fold dilutions in kinetic assays. Briefly, the trans splicing precursors in equal molar concentration were sequentially added to the salt supplemented detergents, incubated overnight at 20° C. to allow splicing to progress, then aliquots were serially diluted to assay buffer from 20 to 1280-fold (dilution induction assay), or 20-fold dilution were made to the corresponding supplemented detergent (detergent suppression assay) and protease activity was assayed with suc-FAAF-pNA (500 μM) substrate by measuring absorbance at 400 nm in a kinetic assay.

Referring to FIGS. 4A-4B, the Detergent-2 and Detergent-1 were supplemented either with sodium nicotinate (90 mM), or NaCl (1M) or with KCl (500 mM), NI and IC were added and dilution inducible iProtease activities were compared as follows:

Formulation: to 66.7 μL of Detergent-2, or Detergent-1 in a PCR tube, 20 μL of appropriate salt, or H$_2$O in the control, was added and mixed by pipetting and swirling. 4.42 μL of purified IC in mTSB buffer (50 mM Tris, 150 mM NaCl, 1 mM DTT, 2 mM CaCl$_2$, pH=7.5) was added into the salted detergent and after thorough mixing and stirring 8.86 μL of purified NI in mTSB buffer was mixed into the detergent+IC. NI and IC were combined at equimolar concentrations. Formulations were stored overnight at 20° C. to allow progression of splicing.

Detergent dilution assay was as follows. In a clear flat-bottomed 96 well plate (Corning 9017, Costar) row A wells were preloaded with 20 μL 1×BR buffer pH 9.0, and 160 μL H$_2$O. Rows B-G were preloaded with 10 μl 1×BR buffer pH 9.0, 90 μL H$_2$O. Twenty microliters of the formulation was added to row A, mixed by pipetting, then 1.00 μL of this 10× diluted sample was added to the 100 μL of water and buffer in row B and mixed. This results in 20× dilution. This 2× serial dilution process was repeated for rows C-G, discarding the excess 100 μL from row G for a final volume of 100 μL in each well. Final detergent concentration in row A, the 20-fold dilution, is 3.3%.

Detergent suppression assay (1:20 in det.) was as follows. In the same plate as above, row H was preloaded with 10 μl 1×BR buffer pH 9.0, 80 μL 100% detergent. 10 μL of the formulations were added individually to each well in row H and mixed. Final detergent concentration in the 20 fold diluted in the suppression assay is 43.3%.

For both assays (to the entire 96 well plate), 100 μL of the 2× suc-FAAF-pNA (500 μM in 20% DMSO) substrate was added and protease activity was assayed by reading absorbance at 400 nm at 30° C.

Detergent final concentration in the suppression assay is 43.3%, in the 20-fold water dilution assay is 3.3%. Referring to FIG. 4A, dilution inducible iProtease in the Detergent-2 supplemented either with sodium nicotinate (90 mM), or NaCl (1M), or KCl (500 mM). Referring to FIG. 4B, dilution inducible iProtease in Detergent-1 supplemented either with sodium nicotinate (90 mM) or NaCl (1M) or KCl (500 mM).

Referring to FIGS. 4A-4B, salt supplemented detergents invariably resulted in higher activity after dilution of formulated NI and IC, compared to their unsalted control. Referring to FIG. 4B, in the Detergent-1 dilution enhancement could be achieved without loss of suppression. However, possibly due to inherent differences in the iProtease activity suppression power of the two detergents, recovered total activities differed significantly in favor to the Detergent-2 (FIG. 4B). These results validated the utility of the detergent additive screen to uncover effectors of dilution inducible enzyme activity and suggested that at least some of the salts could be effective inducers of detergent formulated NI and IC independent from the detergent context.

Trans-splicing is initiated by association of the intein modified precursors. Studies on the DnaE split intein from *Synechocystis* sp. PCC6803 suggested that the split intein parts are disordered and undergo conformational transition from disorder to order upon association (Zheng Y. et al., 2012, which is incorporated herein by reference as if fully set forth). Recent report on the molecular mechanism of association of the model DnaE split intein of *Nostoc punctiforme* confirmed this hypothesis and showed that intein parts interact via a multi-step process initiated by electrostatic interactions followed by compaction and stabilization of the initially disordered intein parts onto a pre-folded region of the N-intein (Shah N H. et al 2013, which is incorporated herein by reference as if fully set forth). This mechanism of "capture and collapse" may be common in naturally split inteins and could be sensitive to effectors that influence charge, charge distribution and hydration properties of the molecules.

Therefore, the effect of changing of the ionic strength of salts identified in the effector screen on direct control dilution inducible iProtease activity independent of the detergent context and tested the KCl was examined.

Example 6. KCl have Dual Roles, Promotes Association of Splicing Precursors and Suppress Splicing Trans-splicing requires association of precursors to initiate a multi-step splicing reaction that eventually yields the active enzyme (Wu H. et al. 1998; Martin et al, 2001; Perler FB. 2005, all of which are incorporated herein by reference as if fully set forth). To have a better understanding at what stage KCl could play a role, KCl (0.125, 0.25, 0.5, 1.0 and 2.0 M) were added to the splicing precursors before the initiation of splicing keeping NI and IC constant and added 2M KCl after 2 hrs. incubation of the splicing mix after completion of splicing.

Cell lysates of NI and IC were separately treated with increasing conc. of KCl from 0.125, 0.25, 0.5, 1.0 and 2.0 M and incubated for 10 min/RT before precursors were mixed and incubated for another 2 hrs./RT to allow progression of splicing in increasing conc. of the salt. Samples were split to two aliquots, one was diluted to BR buffer pH 9.0 (dilution induction assay) the other was diluted to high salt (2M KCl in BR buffer pH 9.0; salt suppression assay) and iProtease was assayed.

Figure 5A:
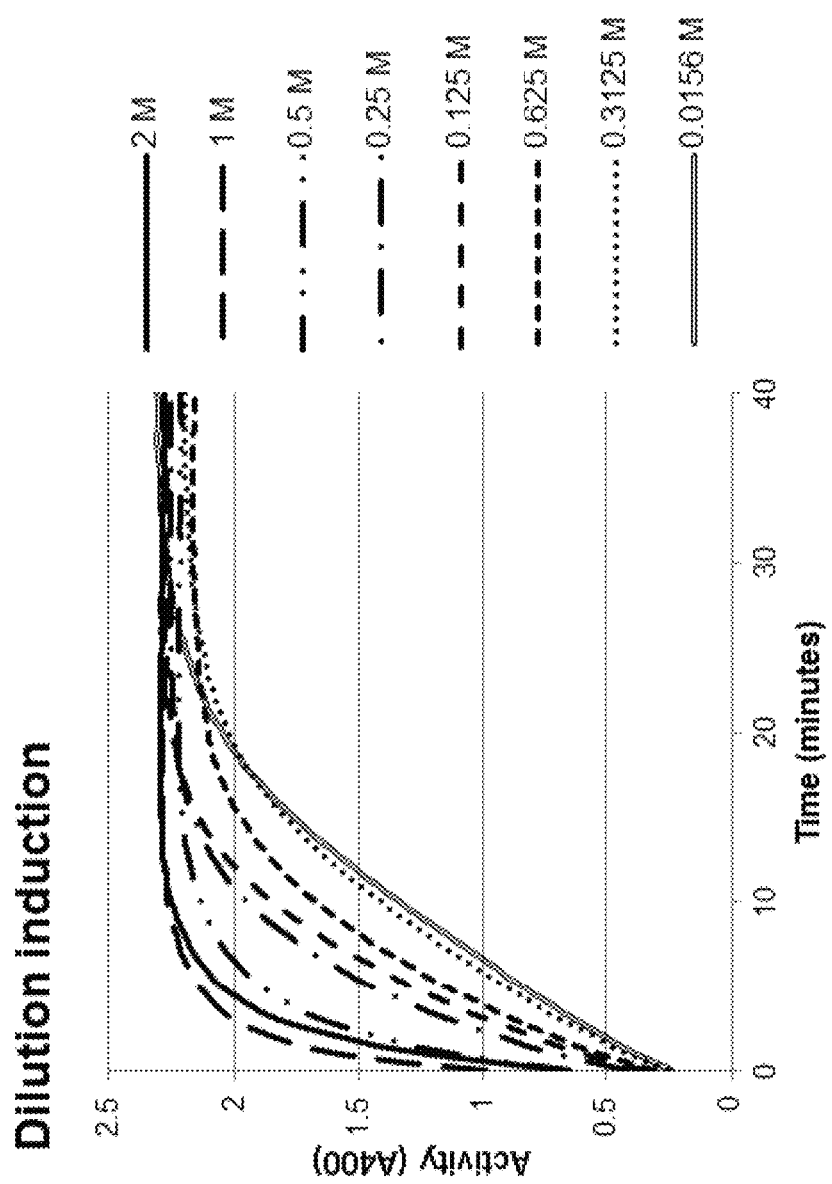
FIGS. 5A-5B illustrate that KCl reversibly inhibits iProtease (iSavinase; NI (SEQ ID NO: 1) and IC (SEQ ID NO: 2)) activity in aqueous buffer.
Figure 5B:
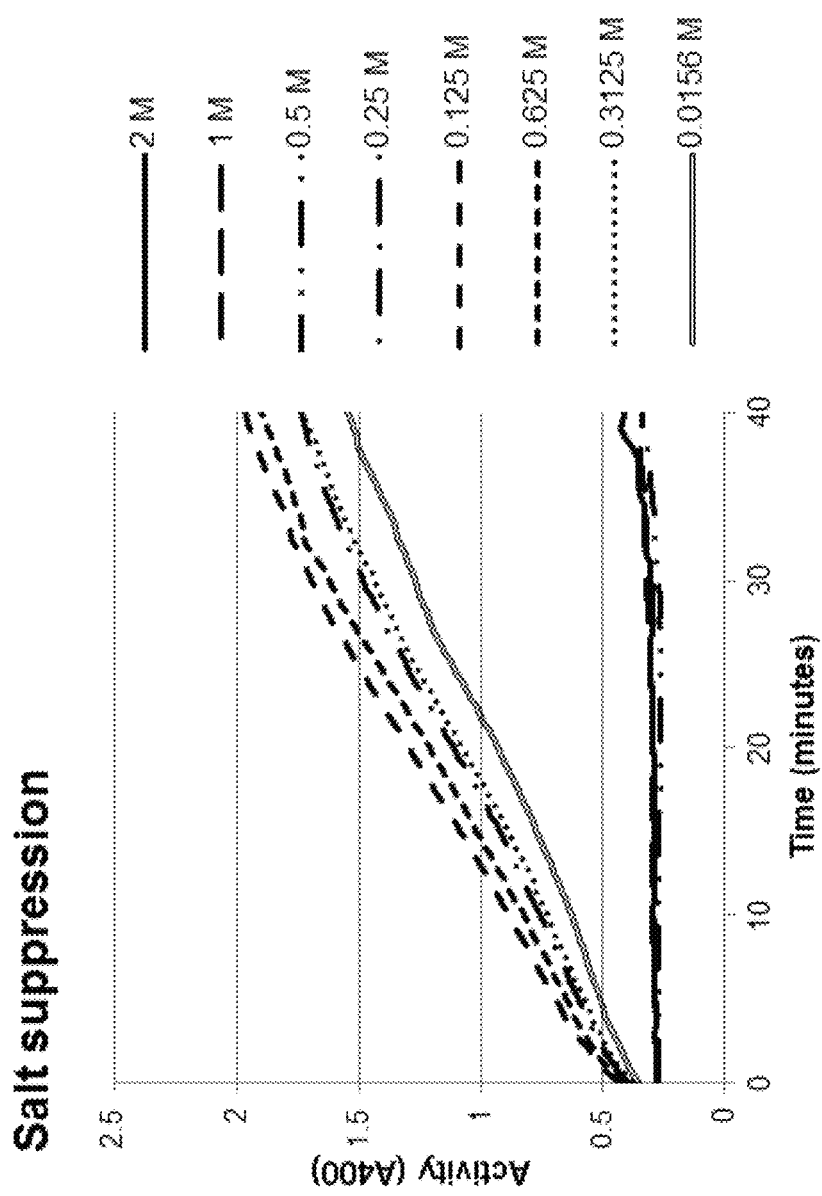

FIGS. 5A-5B illustrate that KCl reversibly inhibits iProtease activity in aqueous buffer. Referring to these figures, 4M KCl was 2-fold serially diluted from 4M to 0.03125M. Two sets of 15 µL aliquots were dispensed to PCR tubes. To one set, 15 µL clarified NI cell lysates were added, to the other set 15 µL clarified IC cell lysates were added and tubes were incubated at room temp for 10 min. Presalted NI and IC in the same conc. of KCl were mixed and incubated at room temperature for 10 min. FIG. 5A illustrates dilution induction assay. Referring to this figure, constant amounts of (NI+IC) premixes in serial dilutions of KCl were 20-fold diluted to BR buffer and assayed for iProtease activity as follows: 5 µL of (NI+IC) premixes were added to 95 µL BR buffer pH 9.0, then 100 µL of suc-FAAF-pNA (500 µM) substrate was added and absorbance was read at 400 nm at 30° C.

FIG. 5B illustrates salt suppression assay. Referring to FIG. 5B, constant amounts of (NI+IC) premixes in serial dilutions of KCl were 20-fold diluted to 2M KCl and assayed for iProtease activity as follows. 5 µL of (NI+IC) premixes were added to 95 µL 2M KCl in BR buffer pH 9.0, then 100 µL of suc-FAAF-pNA (500 µM) substrate was added and absorbance was read at 400 nm at 30° C. It was observed that dilution induction assay recapitulated the dilution induced salt enhancement effects in the detergent contexts. Referring to FIG. 5A, it was observed that the more salt was added to the precursors before mixing the higher the iProtease activity was in the dilutions. Salt suppression assays in 2M KCl revealed another correlation between salt concentration and activity. In samples where salt concentrations were initially high before mixing of the precursors (0.5-2.0 M KCl) and maintained high in the assay (2.0 M KCl), iProtease activity was inhibited. In samples where salt concentration were initially low before mixing the precursors (0.015-0.025 M KCl), iProtease activities increased in the high salt (2M KCl), albeit were below than in their corresponding aliquots diluted to buffer (compare enzyme activities of the same salt concentration buffer in FIG. 5A with FIG. 5B).

There appears to be a high salt regulated enzyme activity switch that requires pretreatment of the precursors with high salt (0.5-2.0 M KCl) before initiation of splicing and dilution of the salt to below 0.5 M KCl to recover activity. Adding high salt (2.0 M KCl) late in the splicing reaction is largely ineffectual, but is inhibitory when kept at high level (>0.5 M KCl) throughout the splicing reaction.

Since trans-splicing requires association of precursors for initiation of splicing, it was hypothesized that KCl may effect this association in two different ways: increase association but suppress splicing, reversibly in a concentration dependent manner.

Association of trans-splicing proteins is a concentration driven reaction which conceivably would be reduced by dilution of the precursors. To determine whether 2M KCl could promote association, precursors were combined in (NI+IC) premix in 2M KCl then sequentially diluted it in 2M KCl. Alternatively, NI and IC were first separately diluted in 2M KCl, then combined the sequentially diluted NI with the sequentially diluted IC to create NI-IC mixes. Samples were then assayed for dilution inducible iProtease.

Figure 6A:
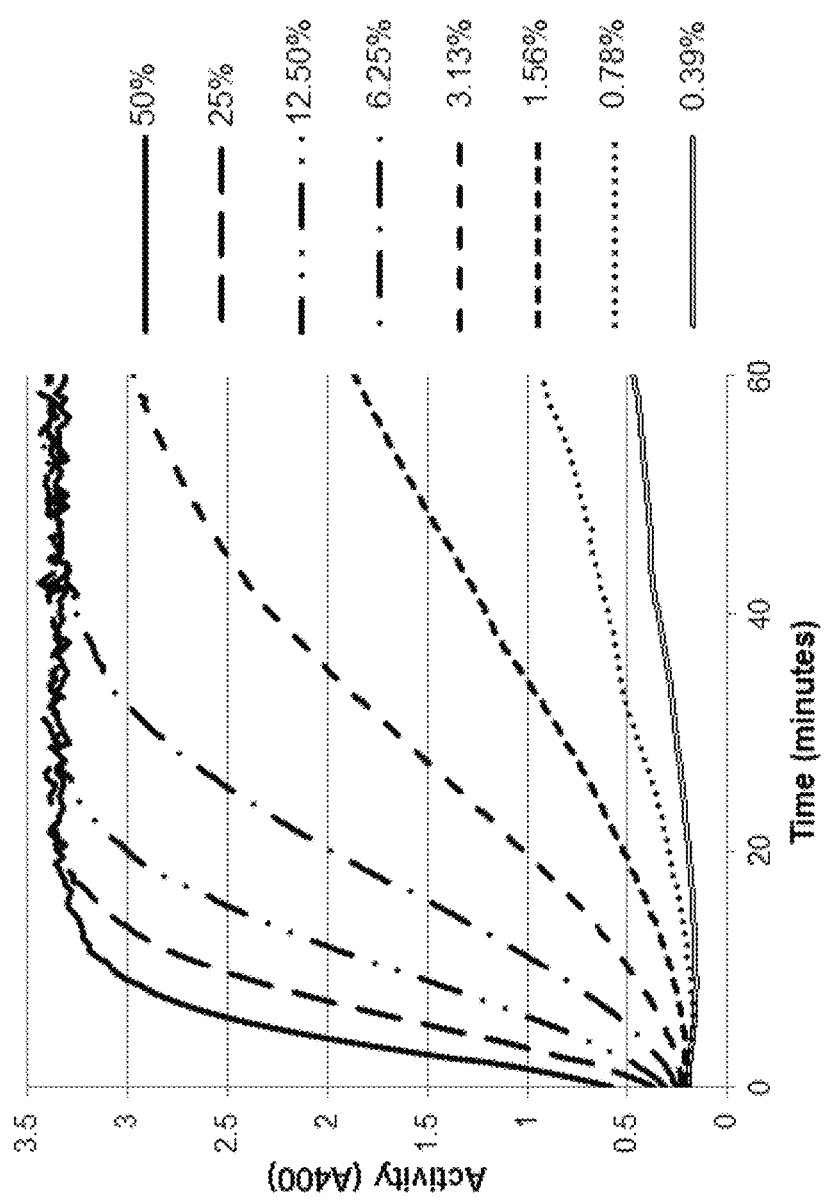
FIGS. 6A-6B illustrate that KCl promotes association of the splicing precursors.
Figure 6B:
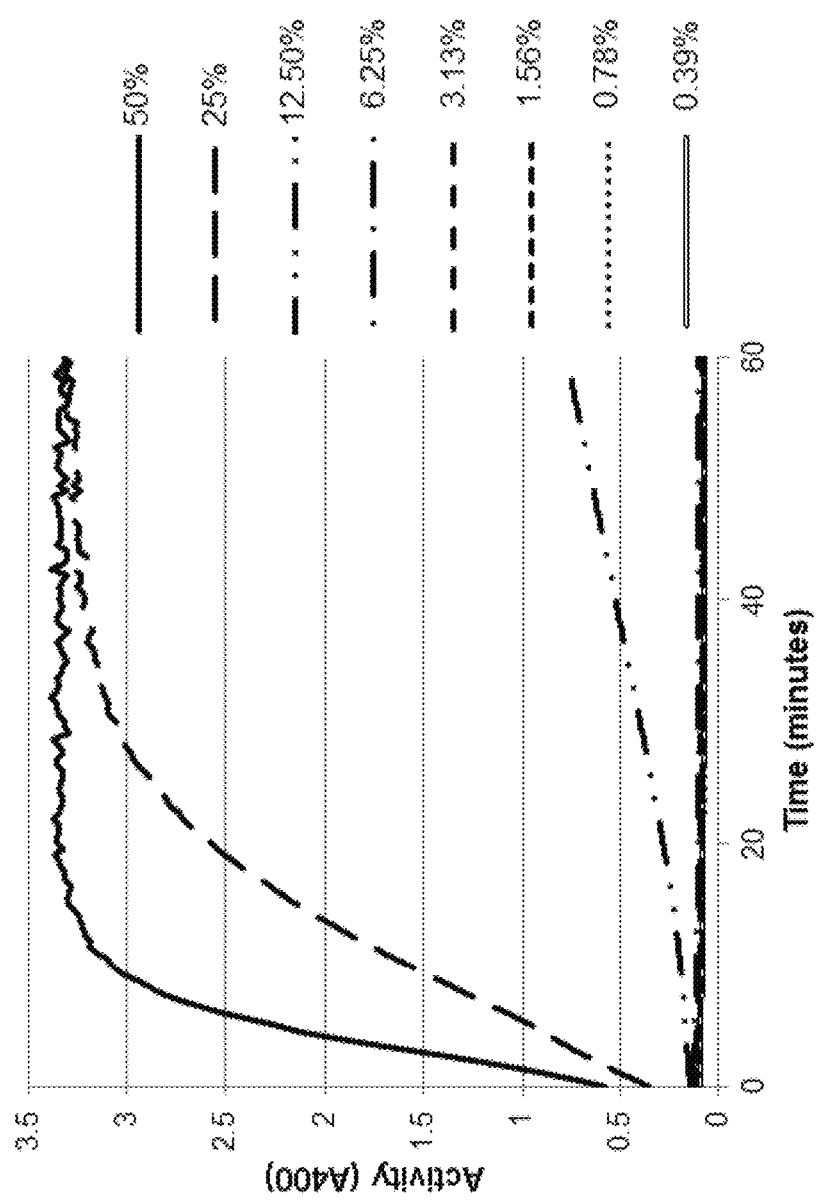

FIGS. 6A-6B illustrate that high concentration of KCl promotes association of the splicing precursors. FIG. 6A illustrates iProtease activity in serial dilutions of the high salt associated (NI+IC) premix in the BR buffer. FIG. 6B illustrates iProtease activity in mixes of separate serial dilutions of NI and IC (NI-IC) in the BR buffer.

Referring to FIG. 6A, the (NI+IC) premixes resulted in iProtease activity in all the 8 serial dilutions, and activity was proportional with the sequentially reduced amounts of NI and IC in the premix. Referring to FIG. 6B, in contrast, in dilutions of the NI-IC mixes iProtease activity quickly dropped below detection level after three dilution steps, indicating that NI and IC concentrations dropped below the level necessary for association and initiation of splicing. These results are consistent with the interpretation that pretreatment of the splicing precursors with high concentration of KCl promotes association of the splicing precursors in the (NI+IC) premix. Referring to FIGS. 6A-6B, assays were set up as follows. Three sets of tubes were set up: to a set of 8 PCR tubes, labeled as (NI+IC)1-8, 40 μL 2M KCl were dispensed. To two sets of 8 PCR tubes labeled NI 1-8 and IC 1-8, respectively, 20 μL 2M KCl were aliquoted.

(1) 50 μL clarified NI lysate was mixed with 50 μL 4M KCl and 50 μL of clarified IC lysate was mixed with 50 μL 4M KCl and incubated at RT for 10 min (2) 20 μL of the pre-salted NI and 20 μL of the pre-salted IC were mixed to tube (NI+IC)1, For controls 20 μL pre-salted NI was added to tube NI. 1; and 20 μL pre-salted IC to tube IC. 1 and mixed.

(3) 40 μL of (NI+IC) 1 was then added to tube marked (NI+IC) 2 and mixed; 20 μL of NI.1 was added to NI.2 tube, and 20 μL of IC.1 was added to IC.2 tube, and mixed. These steps were repeated to create stepwise dilutions of up to (NI+IC) 1-8, NI 1-8 and IC 1-8. Then NI 1 was mixed with IC 1, NI 2 with IC 2 to create the NI–IC 1-8 set.

(4) (NI+IC) and NI–IC sets were incubated at RT for 10 min.

(5) To assay dilution inducible iProtease activity, 5 μL aliquots of the (NI+IC) or NI–IC were mixed with 95 μL BR buffer pH 9.0 then 100 μL of suc-FAAF-pNA (500 μM) substrate was added and absorbance was read at 400 nm in a kinetic assay at 30° C.

FIG. 6A illustrates iProtease activity in serial dilutions of high salt associated (NI+IC) premix in dilutions to BR buffer.

FIG. 6B illustrates iProtease activity in mixes of separate serial dilutions of NI and IC (NI–IC) in BR buffer.

To determine whether iProtease is generated by splicing or via association driven protein complementation, splicing was evaluated. Due to concerns that the splice product may be difficult to detect because it has protease activity and may auto-degrade. Therefore, to protect the splice products from proteolytic auto-degradation, alanine was mutated the serine catalytic residue of the iProtease in the IC (S326A). Splicing was tested by mixing equal volumes of crude lysates of E. coli expressed splicing precursors. Two mixes were made, with or without salt treatment of the precursors. Salt treatment was by mixing separately equal volumes of NI and IC with equal volumes of 2M KCl, before mixing the precursors. In the unsalted sample, equal volume of $H_2O$ was added to each precursor before mixing. The unsalted and salted mixes of (NI+IC) and (NI+$IC^{S326A}$) were quickly diluted to aqueous buffer and aliquots were taken at t=0, 1 min and 30 min to 2×SDS loading dye+5% βME, and total protein profiles were analyzed on Coomassie stained 12% SDS/PAGE. Residual KCl concentration in salt pretreated (NI+IC) mix was 200 mM after dilution to aqueous buffer.

In dilutions of the unsalted (NI+IC) and (NI+$IC^{S326A}$), a new protein species accumulated at the expected size for the splice product, late in the splicing reaction at t=30 min. In the protease inactivated salted precursor mix of (NI+$IC^{S326A}$), splice product was instantly visible at t=0 and stayed at the same high level, and there were no sign of proteolytic degradation. In the salted precursor mix of wild type (NI+IC), splice product detection was weakened due to instant protein degradation, and most of the proteins were degraded by t=30 min. These observations are consistent with the interpretation that mixing of the precursors results in splicing and that pretreatment of the precursors with equal volume of 2M KCl before mixing results in splicing and ultra-fast protease activity.

Figures 7A, 7B:
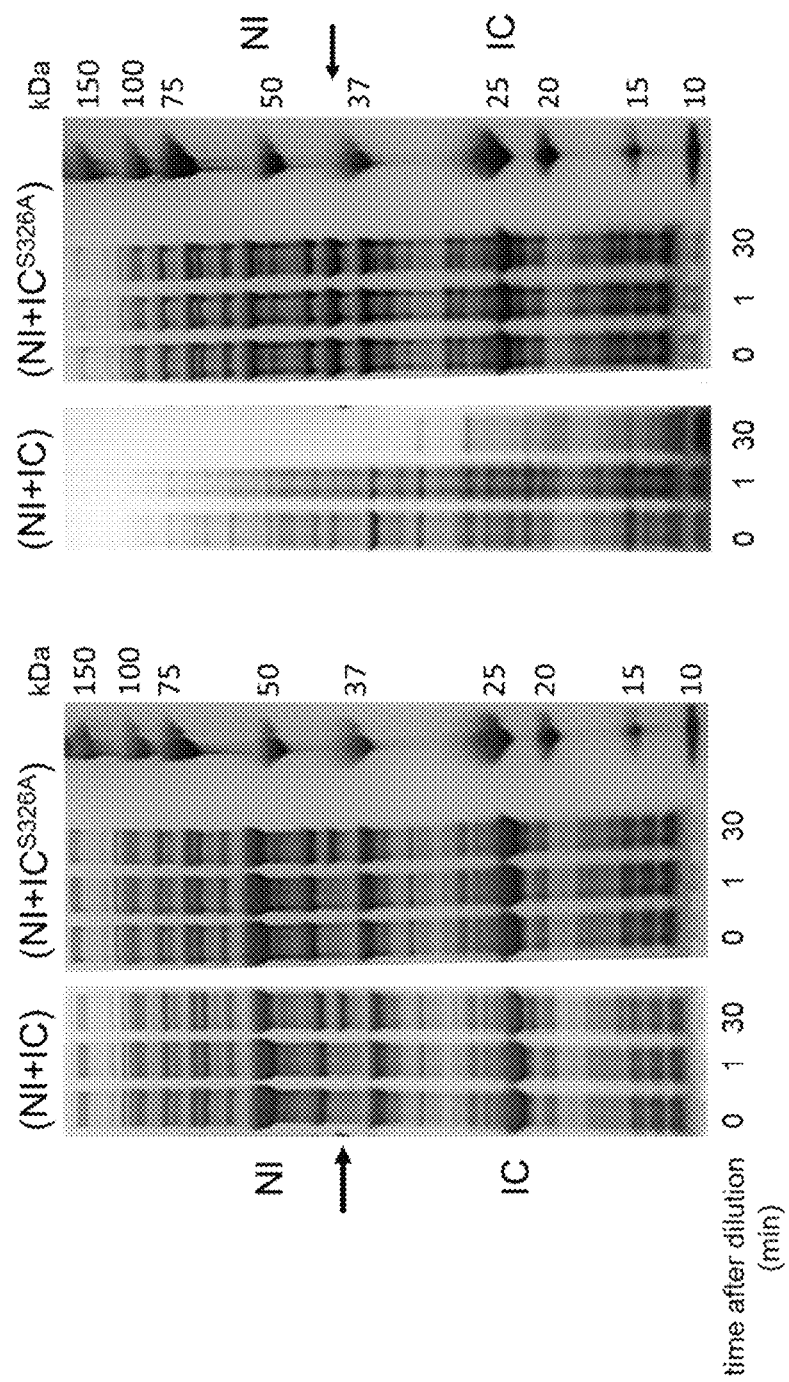
FIGS. 7A-7B illustrate Coomassie gels that show splicing after mixing of the splicing precursors (NI (SEQ ID NO: 1)+IC (SEQ ID NO: 2), intein-modified precursors of iSavinase, and NI (SEQ ID NO: 1)+IC$^{S326A}$ (SEQ ID NO: 58) intein-modified precursors of iSavinase, wherein in the IC precursor, alanine was mutated to the serine catalytic residue (S326A)).

FIGS. 7A-7B illustrate that a coomassie gel shows splicing after mixing the splicing precursors NI and IC. Referring to these figures, splicing was evaluated after mixing of the splicing precursors and following proteins profiles over 30 min on Coomassie stained 12% SDS/PAGE. To protect the splice products from proteolytic auto-degradation the serine catalytic residue in the IC were alanine mutated to create ($IC^{S326A}$). 2× concentrated cell lysates of NI, IC and the $IC^{S326A}$ were prepared as shown in FIG. 2A (total protein profiles) and FIG. 2B (soluble protein profiles). To prepare the salted premix, NI or IC or $IC^{S326A}$ were separately mixed with equal volume of 2M KCl. After 10 min at RT, 25 μL of NI in 1M KCl was mixed with 25 μL IC in 1M KCl, and in a separate sample 25 μL NI was mixed with 25 μL $IC^{S326A}$. Immediately after mixing, 20 μL of the (NI+IC) and (NI+$IC^{S326A}$) were diluted with 70 μL deionized water supplemented with 10 μL BR buffer pH 9.0, and at the t=0 time point 20 μL aliquots were immediately taken into 20 μL 2×SDS loading dye+5% βME, and samples were heated at 95° C./5 min. Further aliquots were taken at 1 min and at 30 min after dilution and were processed similarly. Residual KCl concentrations in the diluted samples were 200 mM, before adding the loading dye. 15 μL samples were separated on 12% SDS/PAGE and the gels were stained with Coomassie. To prepare the unsalted premixes, samples were handled by the same protocol but instead of 2M KCl, $H_2O$ was added to the 2× concentrated cell lysates. FIG. 7A illustrates protein profiles after dilution of unsalted premix to aqueous buffer. Referring to this figure, 30 min after mixing of precursors to initiate splicing a new protein species accumulated in both (NI+IC) and NI+$IC^{S326A}$) at the expected size for the splice product. FIG. 7B illustrates protein profiles after dilution of salted premix to aqueous buffer. Referring to this figure, in the (NI+IC) samples protein degradation was instantly visible after initiation of splicing in the t=0 time point and by t=30 min most of the proteins were degraded. In the protease inactivated (NI+$IC^{S326A}$) premix, there was no visible protein degradation and large amounts of splice product was detectable at t=0. Positions of the NI and IC and $IC^{S326A}$ are marked. Position of the splice product is marked by arrow.

KCl appeared to be a potent effector of NI and IC, promoted association of the splicing precursors into a splicing inactive form, suppressed iProtease activity at concentration higher than 0.5 M, which could be reversed by reducing KCl concentration bellow 0.5 M. By this measures, KCl is an inhibitor and conditional regulator of trans-splicing regulated iProtease.

Because of the shared structural features including disordered structures and charge distribution between the two intein halves and shared mechanisms for association among trans-splicing inteins, the high salt controlled association of split-intein modified protein fragments possibly is not restricted to NI and IC, but could be applicable to other split-intein modified proteins, and could have use in assembling two- or more trans-intein modified protein fragments for controlled activity. (Zheng Y. et al., 2012; Shah N H. et al 2013, Aranko A S. Et al., 2013, all of which are incorporated by reference as if fully set forth). Salt based conditional regulation, as exampled by the KCl regulated iProtease, could provide a simple and possibly more generic approach to regulate trans-splicing intein modified proteins for controlled activity. A major advantage of this strategy is reliance on wild type trans-splicing inteins and avoidance of the normally difficult genetic engineering of trans-splicing inteins for conditional regulation of target protein activity (Mootz et al, 2003; Selgrade et al. 2013, both of which are incorporated herein by reference as if fully set forth).

Effector screens for dilution inducible iProtease showed that compounds of diverse chemical nature, electrolytes, polyelectrolytes, polyols, hydrotropes (glycerol, monopropylene glycol, nonionic ex Shell (Neodol) could be effectors. Conceivably, chemicals with similar physicochemical characteristics could also perform similarly. Because effectors appear to be more numerous than splicing inhibitors, $Zn^{++}$, $Cu^{++}$ or cistatin and have diverse chemistry, possibly they could be better tailored to the needs of specific applications, including extreme chemical conditions, when activity of the target protein need to be conditionally regulated (Nichols N M. et al, 2003; Sun P. et al, 2005; Zhang L. et al, 210; Zhang L. et al, 2011, all of which are incorporated by reference as if fully set forth).

Examples 7-16 describe using an effector of detergent dilution inducible iProtease activity in liquid laundry detergent formulation for stable storage and dilution inducible efficient recovery of protease activity. The examples describe formulation of KCl stabilized. (NI+IC) premixes to aqueous solutions and to liquid laundry detergents for stable storage and efficient recovery of protease activity quickly, without loss of cleaning efficiency.

Example 7. Benchmarking of Dilution Induced iProtease to Savinase

Purified NI stock was 45 mg/mL (855.9 micromolar) in mTSB buffer (50 mM Tris, 150 mM NaCl, 1 mM DTT, 2 mM CaCl2, pH 7.5). Purified IC stock was 33.58 mg/mL (1460 micromolar) in mTSB buffer. To benchmark iProtease activity to 1% (vol/vol) Savinase (~103 g/L, Novozymes), each of purified NI and IC was used at 38.1 μmolar concentration. (NI+IC) premix for 7×200 μL volume formulations was made as follows: to 62.3 μL NI in Eppendorf tube 6.23 μL 100 mM DTT was added. After 10 min at room temperature (RT), equal volume (68.53 μL) of 4M KCl was added by mixing and the sample was incubated for 10 min at RT. To 36.4 μL IC in Eppendorf tube 3.64 μL of 100 mM DTT was added and mixed. After 10 min at RT, equal volume (40.0 μL) of 4 M KCl was added and the sample was incubated at RT for 10 min. To prepare 4× concentrated (NI+IC) premix in 2M KCl, 137 μL of NI in 2M KCl was mixed with 80 μL IC in 2M KCl, mixed by pipetting. After 10 min at RT, 133 μL of 2M KCl was added, that resulted in 350 μL (NI+IC) premix (4×). In aqueous formulations 50 μL of 4× concentrated (NI+IC) premix was added to 150 μL deionized water+KCl; KCl final concentration was 1M. When formulations were made to detergent, 50 μL of 4× concentrated (NI+IC) premix was added to 150 μL of KCl supplemented detergent. KCL final concentrations in the formulations were 1M, NI and IC final concentrations were 38.1 μmolar each.

Savinase (~103 g/L, inhibitor stabilized stock) was KCl treated essentially as NI and IC as follows. Savinase was diluted 3-fold in mTSB buffer. To 60 μL Savinase in mTSB, 190 μL deionized water and 250 μL of 4 M KCl was added to prepare 500 μL of 4× concentrated stock in 2M KCl, sufficient for 10×200 μL formulations of 1% (v/v) Savinase. In aqueous formulations, 50 μL of 4× Savinase in 2M KCl premix was added to 150 μL deionized water+KCl; KCl final concentration was 1M. When formulations were made to detergent, 50 μL of 4× Savinase in 2M KCl premix was added to 150 μL of the KCl supplemented detergent. Savinase was 1%, KCL final concentrations in the formulations were 1M.

Protease assays were performed in 96 well plates (Corning 9017, Costar, clear flat bottom). Row A wells were preloaded with 20 μL 1×BR buffer pH 9.0, and 160 μL $H_2O$. Rows B-H were preloaded with 10 μl 1×BR buffer pH 9.0, 90 μL $H_2O$. 20 μl of the formulation was added to row A, mixed by pipetting, then 100 μL of this 10× diluted sample was added to the 100 μl buffer and water in row B and mixed. This results in 20× dilution. This process of 2× serial dilutions was repeated for rows C-H. This is the detergent dilution assay. To 100 μL samples in the wells 100 μL of a 2× suc-FAAF-pNA (500 μM in 20% DMSO) substrate was added and iProtease activity was assayed by reading absorbance at 400 nm at 30° C.

Figure 8B:
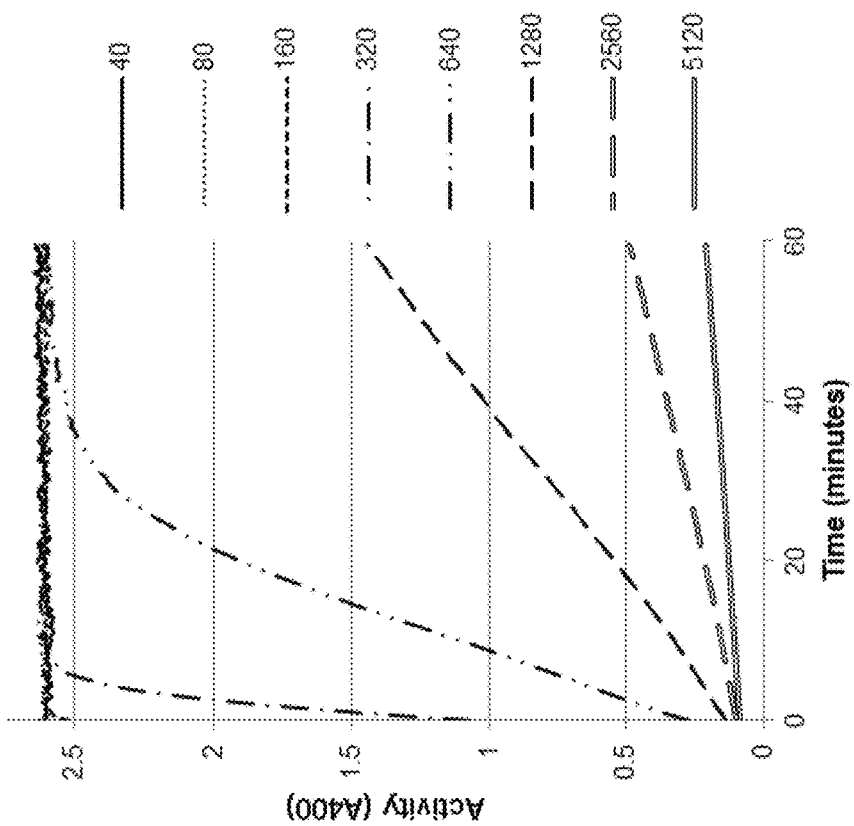
FIGS. 8A-8B illustrate benchmarks dilution inducible iProtease (iSavinase; NI (SEQ ID NO: 1) and IC (SEQ ID NO: 2)) activity to 1% Savinase (SEQ ID NO: 6).
Figure 8A:
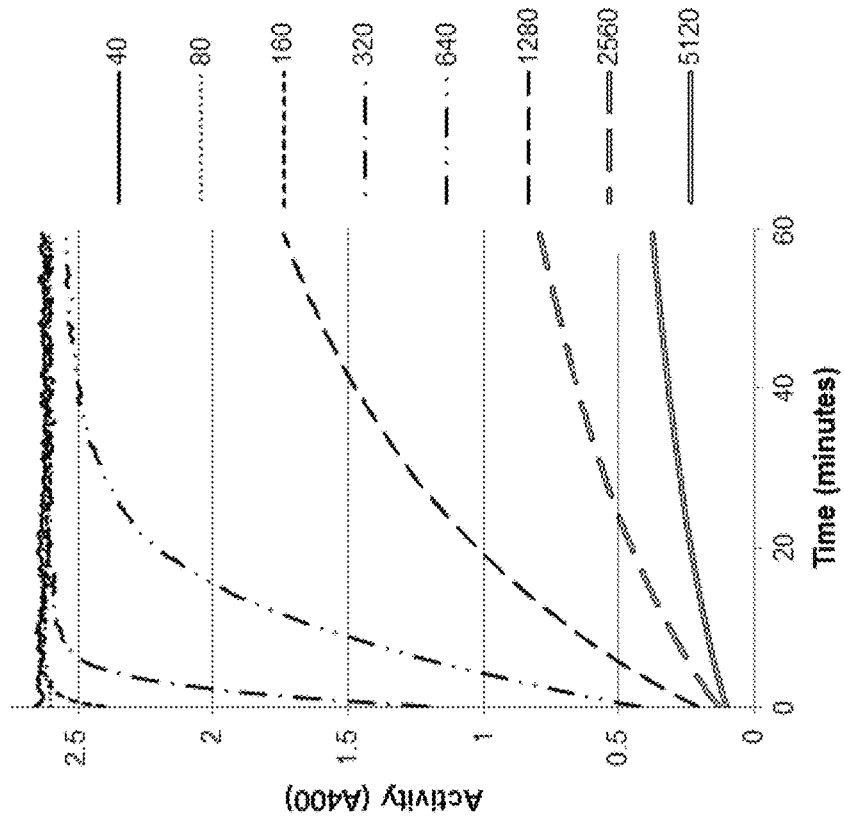

FIGS. 8A-8B illustrate benchmarking of dilution inducible iProtease activity to 1% Savinase. Referring to these figures, it was observed that iProtease (FIG. 8A) and Savinase (FIG. 8B) have comparable dilution activity profiles. Results demonstrated robust activity and ultra-fast recovery of iProtease activity with above 95% efficiency.

Example 8. KCl Stabilized (NI+IC) Premix had No Protease Activity iProtease activity was benchmarked to 1% (v/v) Savinase. Formulation of (NI+IC) and Savinase to 1M KCl aqueous buffer was the same as in Example 1, but enzyme activity was assayed in 2M KCl as follows: In a clear flat-bottomed half-volume 96 well plate, row A wells were preloaded with 10 μL 1×BR buffer pH 9.0, 50 μl 4 M KCl, and 35 μL $H_2O$. Rows B-H were preloaded with 5 μl 1×BR buffer pH 9.0, 25 μL 4 M KCl, and 20 μL $H_2O$. 5 μl (NI+IC) formulation was added to row A, mixed by pipetting, then 50 μL of this 20× diluted sample was added to the 50 μl salt, buffer, and water in row B and mixed. These resulted in 40× dilution. This process of 2× serial dilutions was repeated for rows C-H. All samples were diluted an addition 2× by adding 50 μL 500 μM suc-FAAVF-pNA (in 20% DMSO) substrate, yielding samples diluted from 40× in row A to 5120× in row H. Protease activity was assayed by reading absorbance at 400 nm at 30° C. FIGS. 9A-9B illustrate that KCl stabilized (NI+IC) premix has no enzyme activity. FIG. 9A illustrates iProtease activity of the 80-fold diluted (NI+IC) premix. FIG. 9A illustrates Savinase. It was observed that 1M KCl inhibited protease activity of (NI+IC) premix but did not inhibit protease activity of the intein unmodified reference enzyme, Savinase.

Figures 10A, 10B:
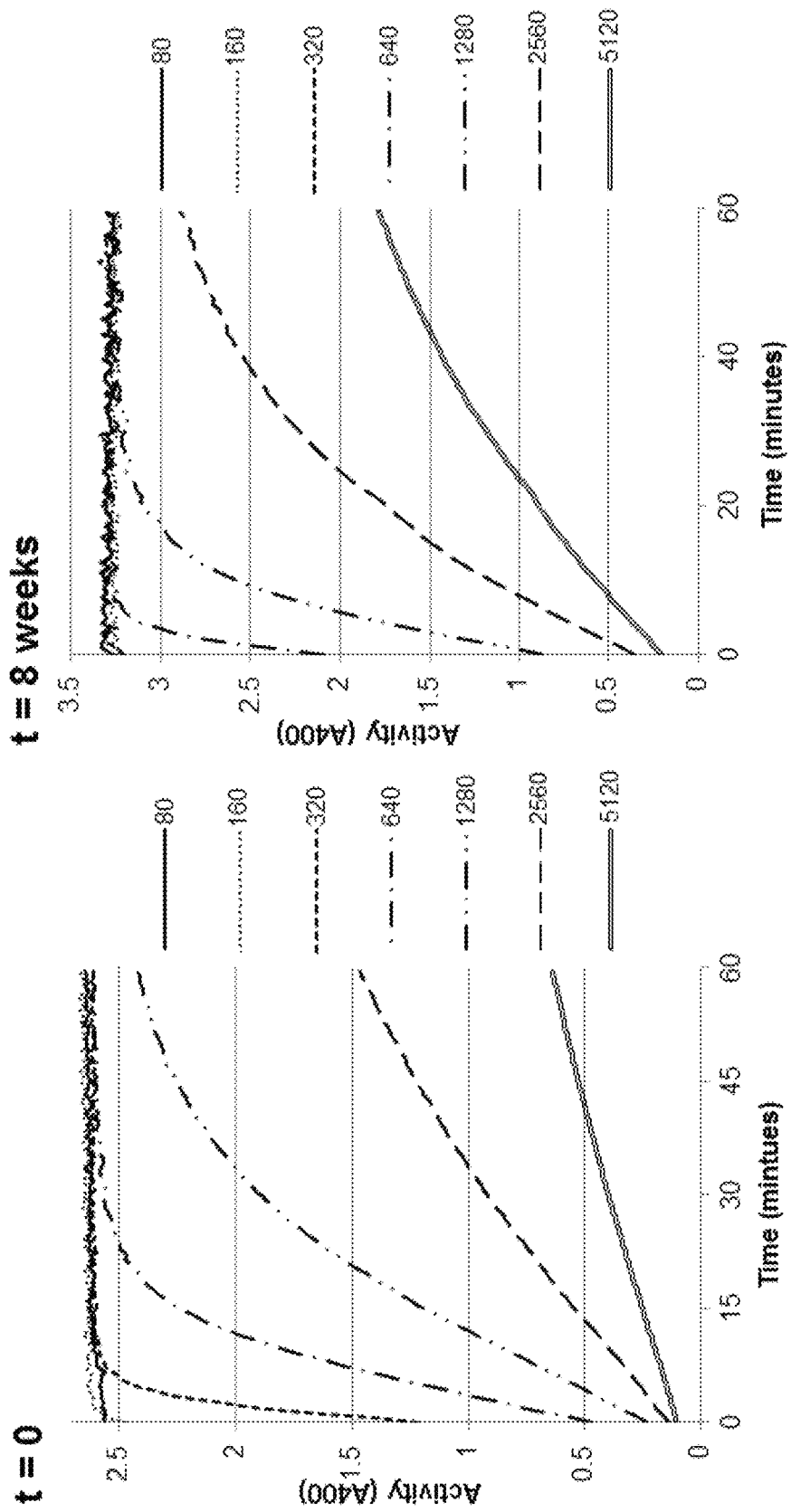
FIGS. 10A-10B illustrate storage stability of the KCl stabilized (NI (SEQ ID NO: 1)+IC (SEQ ID NO: 2), intein-modified precursors of iSavinase or iSav) premix in the aqueous buffer.

Example 9. KCl Stabilized (NI+IC) Premix can be Stored in Aqueous Buffer without Significant Loss of Activity 4× concentrated (NI+IC) premix was prepared in 2M KCL as in Example 1 and stored at 4° C. 4× (NI+IC) premix was formulated to aqueous buffer at t=0 and after 8 weeks storage at 4° C. and assayed for iProtease activity as described for Example 8. FIGS. 10A-10B illustrate storage stability of KCl stabilized (NI+IC) premix in aqueous buffer. Referring to these figures, comparison of dilution inducible activities at t=0 with t=8 weeks indicated no loss of dilution inducible iProtease activity. The slightly higher activity at t=8 possibly due to ambient temperature difference in the assay. Retention of inducible activity showed high storage stability.

Figures 11A, 11B:
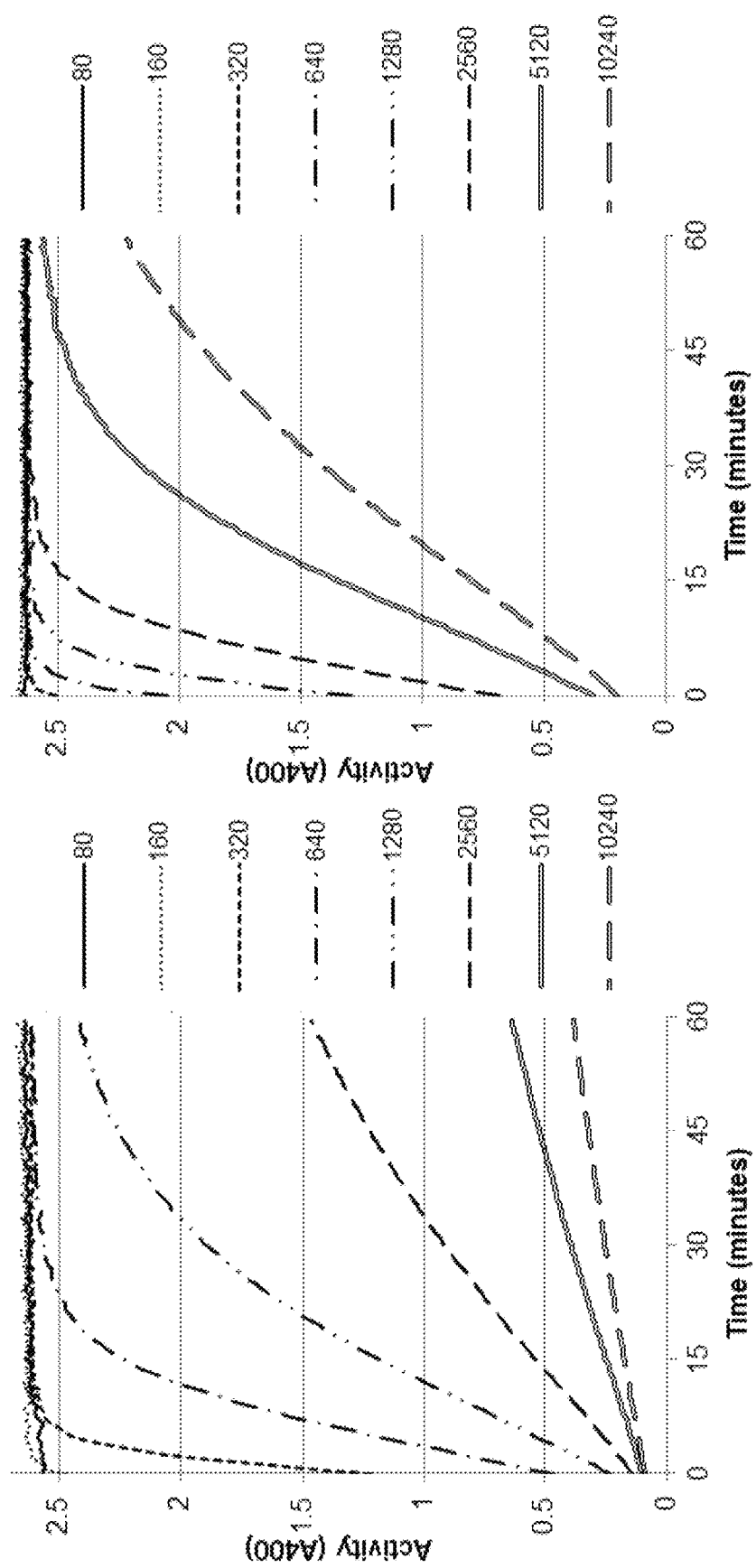
FIGS. 11A-11B illustrate that the KCl stabilized (NI (SEQ ID NO: 1) +IC (SEQ ID NO: 2), intein-modified precursors of iSavinase or iSav) premix can be formulated to the Detergent-1 without loss of the dilution inducible activity.

Example 10. KCl Stabilized (NI+IC) Premix can be Formulated to Detergent-1, without Loss of Dilution Inducible Activity This assay evaluated dilution induction efficiency of Detergent-1 formulated KCl stabilized (NI+IC) premix. Purified (NI+IC) premix was prepared at benchmarking concentrations and aliquots were formulated either to aqueous buffer with 1 M KCl or into 50% Detergent-1 supplemented with 1M KCl, as described in Example 8. iProtease activity was measured in sequential dilutions from 80- to 10240-fold dilutions to aqueous buffer. FIGS. 11A-11B illustrate that KCl stabilized (NI+IC) premix can be formulated to Detergent-1 without loss of dilution inducible activity. FIG. 11A shows dilution activities from 1 M KCl aqueous buffer. FIG. 11B shows dilution activities from 50% Detergent-1-1M KCl. Detergent-1 formulated premix retained full dilution inducibility. Dilution induction was ultra-fast and highly efficient.

Figure 12:
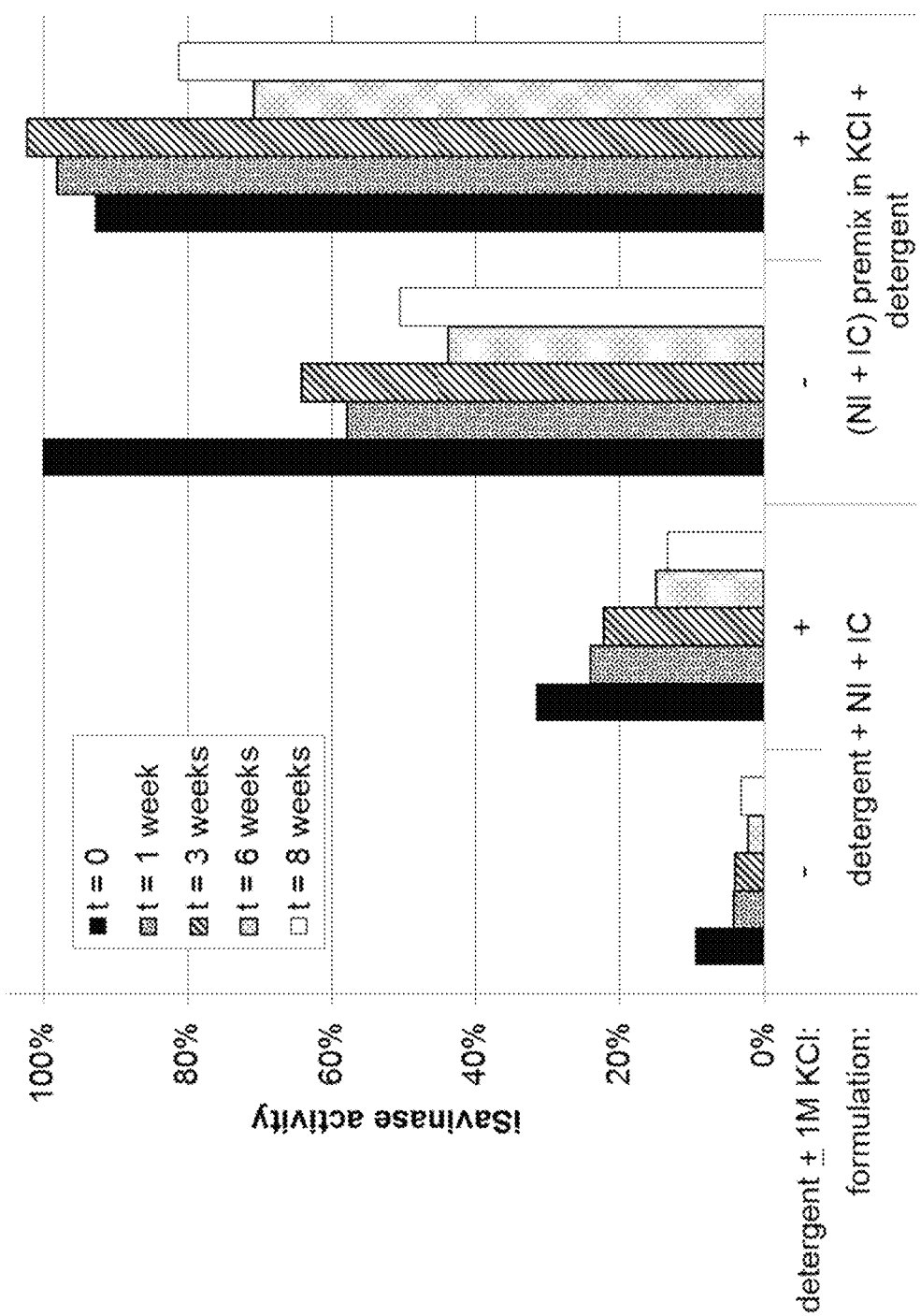
FIG. 12 illustrates that KCl has dual roles in detergent formulation: stabilize (NI (SEQ ID NO: 1)+IC (SEQ ID NO: 2), intein-modified precursors of iSavinase or iSav) premix for formulation and maintain stability in detergent.

Example 11. KCl has Dual Roles in Detergent Formulation: Stabilize (NI+IC) Premix for Formulation and Maintain Stability in Detergent FIG. 12 illustrates comparison of alternative protocols to detergent formulate NI and IC and evaluated formulations for long term stability. Two formulation protocols as follows were compared: 1) formulation by sequential mixing of unsalted NI and IC to the detergent (detergent+NI+IC) and 2) formulation of KCl stabilized (NI+IC) premix to detergent. Detergent-1 was used at 60% (v/v) in two formats, either without supplement (−), or KCl supplement was added to 1M final concentration (+). Purified NI and IC were each used at benchmarking conc. to 1% (v/v) Savinase, at 38.1 µmolar concentration each. (NI+IC) premix was prepared and formulated to the detergent essentially as described in Example 7. Formulations were stored at 37° C. under accelerated ageing conditions and storage stabilities were tested by assaying retention of dilution inducible iProtease activity over 8 weeks at t=0, 1, 3, 6 and 8 weeks in storage. Dilution inducible activity was assayed in sequential dilutions to assay buffer, from 40- to 5120-fold dilutions as described in Example 7. iProtease activities at the 2 min time point reads of the 1:1280-fold dilutions were normalized to dilution induced iProtease activity of the (NI+IC) premix in detergent without salt at t=0 and were plotted.

Results confirmed advantage of formulating 1M KCl stabilized (NI+IC) premix over formulation by sequential mixing of NI and IC to the detergent, and showed the benefit of having 1M KCL supplement in the detergent for long term storage. In the formulation made by sequential mixing of NI and IC into detergent without salt supplement, iProtease activity was low and quickly declined. Supplementing the detergent with 1M KCl boosted activity approximately 3-fold but inducible activity gradually declined over time.

Formulation of (NI+IC) premix resulted in high initial activity at t=0, but storage stability was weak in the unsupplemented detergent, and retention of dilution inducible activity gradually declined by approximately 50% over 8 weeks. Best results were obtained when the KCl stabilized (NI+IC) premix was formulated to 1M KCl supplemented detergent. This formulation retained dilution inducible full activity over 3 weeks and approximately 80% activity over 8 weeks, indicating that 1M KCl is important both in the formulation of trans splicing precursors and as a detergent additive to maintain reversible inhibition of dilution inducible activity.

FIG. 12 illustrates that KCl has dual roles in detergent formulation: stabilize (NI+IC) premix for formulation and maintain stability in detergent.

Figure 13:
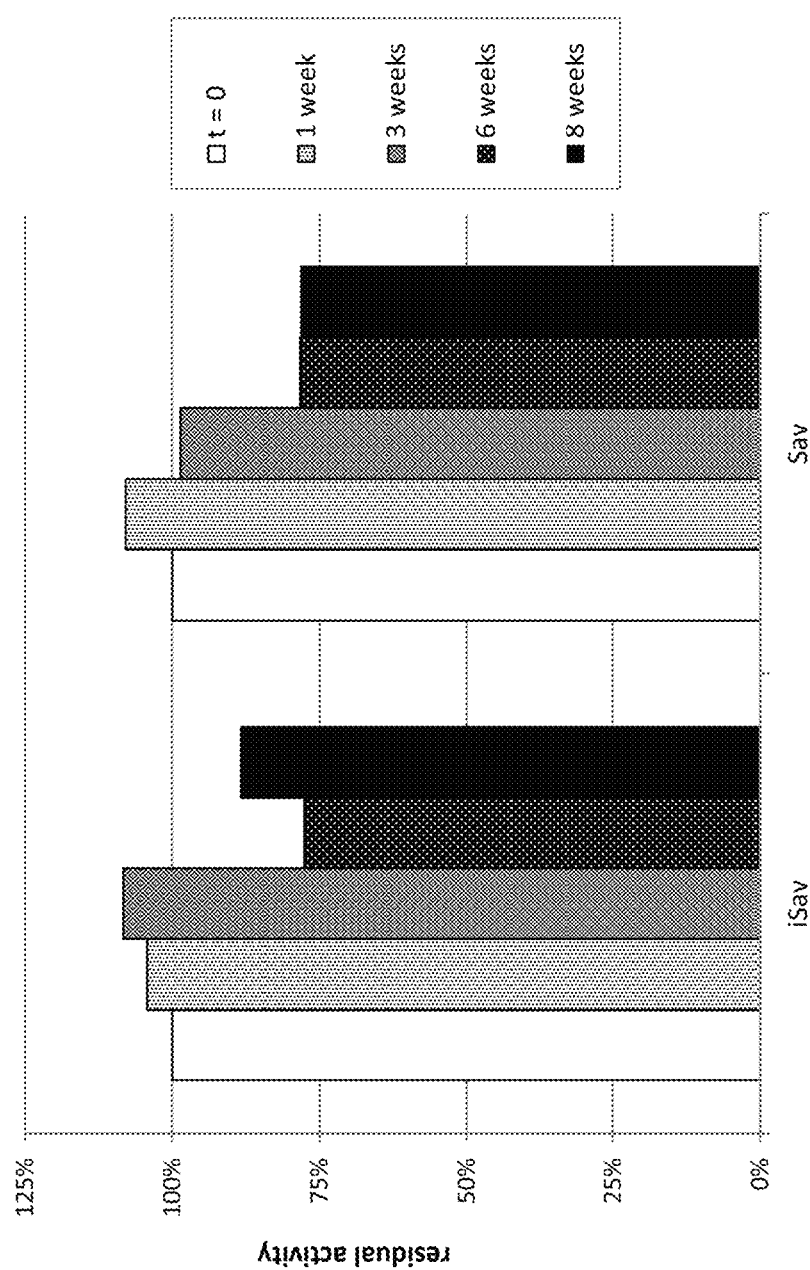
FIG. 13 illustrates that iProtease (also referred to herein as iSavinase; or iSav; NI (SEQ ID NO: 1) and IC (SEQ ID NO: 2)) storage stability in Detergent-1 is comparable with Savinase (Sav; SEQ ID NO: 6) under accelerated ageing conditions.

Example 12. iProtease Stability was Comparable with Savinase in Detergent-1 Under Accelerated Ageing Conditions Savinase was used at 1% (v/v) and formulated to 60% Detergent-1 supplanted with 1M KCl. Purified NI and IC were used at equimolar concentration to 1% (v/v) Savinase, at 38.1 µmolar concentration each. (NI+IC) premix was prepared and formulated to 60% Detergent-1 supplemented with KCl to 1 M final concentration of the KCl, as described in Example 11. Formulations were stored at 37° C. under accelerated ageing conditions and storage stability was tested by assaying retention of dilution inducible iProtease activity over 8 weeks at t=0, 1, 3, 6 and 8 weeks in storage. FIG. 13 illustrates iProtease storage stability in Detergent-1 is comparable with, Savinase under accelerated ageing conditions. Referring to this figure, protease activities were assayed in sequential dilutions to assay buffer as described before and iProtease and Savinase activities at the 2 min time point reads of the 1:1280-fold dilutions were normalized each to its t=0 as 100% and residual activities were graphed.

Residual activity profiles of iProtease were comparable with Savinase. Both formulations retained approximately 75-80% activity under accelerated ageing conditions after 8 weeks at 37° C. Results demonstrated that the trans-splicing intein technology can be effectively used for protease stabilization in liquid laundry detergent.

Figure 14:
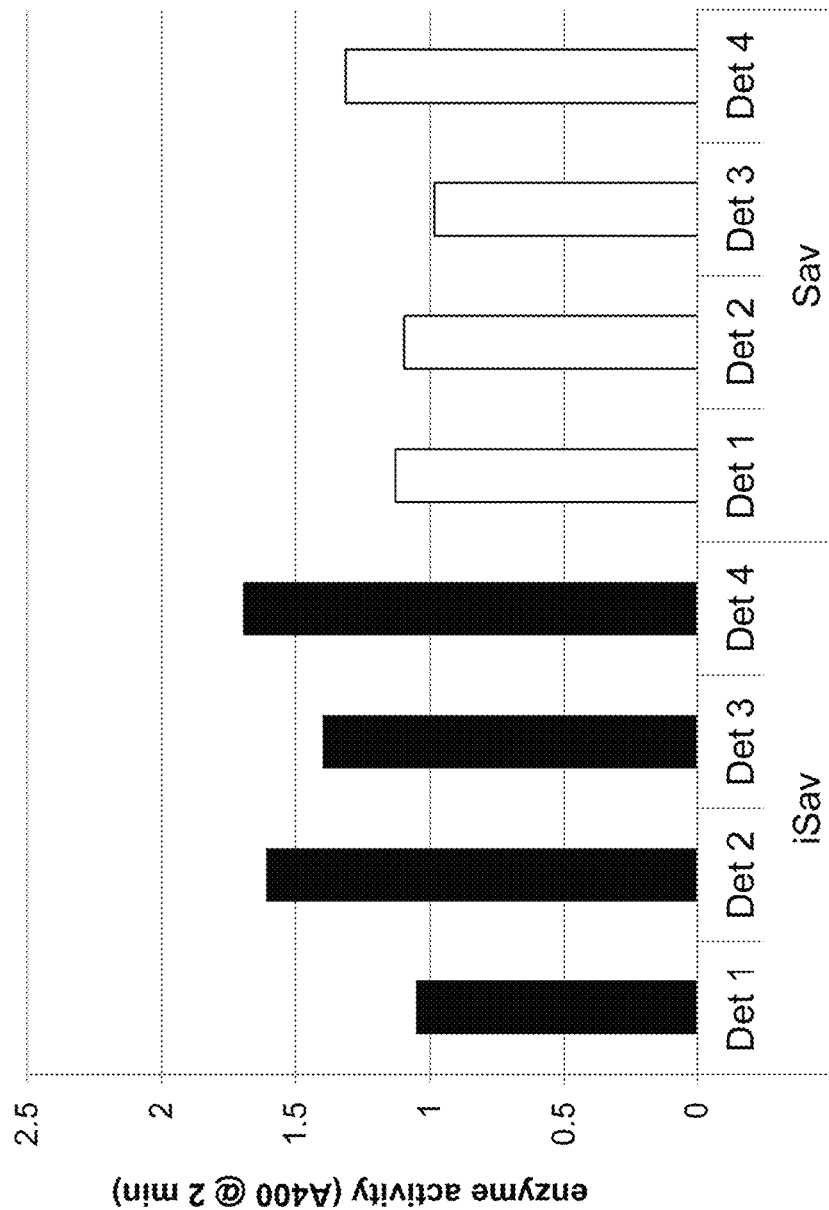
FIG. 14 illustrates in detergent dilution assays that KCl stabilized (NI+IC, shown as iSavinase (iSav); NI (SEQ ID NO: 1) and IC (SEQ ID NO: 2)) premix is compatible with four liquid laundry detergents compared with Savinase (Sav; SEQ ID NO: 6).

Example 13. KCl Stabilized (NI+IC) Premix was Compatible with Four Different Types of Detergents This assay evaluated four different types of liquid laundry detergents for dilution inducible iProtease activity: Detergent-1, Detergent-2, Detergent-3 and Detergent-4. Detergents were either enzyme free formulations (Detergent-1, Detergent-4) or commercial brand detergents (Detergent-2, Detergent-3) with formulated protease that were inactivated by heat treatment.

iProtease was benchmarked to 1% (v/v) Savinase. Preparation of KCl stabilized (NI+IC) premix and formulations to 1M KCl supplemented 50% detergents were made as described in Example 7. Savinase was formulated at 1% (v/v) to 1M KCl supplemented 50% detergent using the same protocol as in Example 8. FIG. 14 illustrates that detergent formulated KCl stabilized (NI+IC) premix retains full dilution inducible activity in different types of detergents: Detergent-1, Detergent-2, Detergent-3 and Detergent-4. Referring to this figure, protease activities were assayed in sequential dilutions to assay buffer as described before and iProtease and Savinase activity reads of the 2560-fold dilutions at 2 minutes were graphed. iProtease and Savinase activities were comparable across all the four detergents, indicating that dilution induction of KCl stabilized (NI+IC) premix was largely independent from the detergent.

Example 14. Stain Removal Efficacy of iProtease was Comparable with the Intein Unmodified Enzyme Savinase in Four Liquid Laundry Detergents Formulations made into four different types of detergents and assayed for protease activity (Example 13) were evaluated for stain removal activity as follows:

Soiled cloth standard was as follows. Swiss Standards Agency test fabric, EMPA 117 was used for the tests. The fabric was a polyester/cotton blend, 65/35, soiled with blood/milk/ink. Approx weight: 165 grams/meter$^2$ (4.86 ounces/yard$^2$). Approximate width was 58 inches (147 cm). Circular disks of the fabric were punched out to fit in a standard 96-well microplate. The punch size and the fabric circle diameter was 5.56 mm (7/32; 0.22 inch), with an area of 24.25 mm square.

Reagents were as follows: 120FH buffer (French Hardness Units, 10×) 8 mM calcium chloride (0.887 g CaCl2)+4 mM magnesium chloride (0.813 g MgCl$_2$.6 H$_2$O) in H$_2$O (1000 mL); 200 mM boric acid (10×). 12.37 g boric acid in 1 L H$_2$O; pH to 9.0 with NaOH; and 1.25% detergents in H$_2$O.

Washing:

Washings were run on three replicate fabric disks. Formulated enzyme (iProtease and Savinase) dilutions were made in 50% detergent stock (detergent in dH$_2$O). 1:40 dilutions with dH$_2$O were made for each formulation. Reagents were added to the flat bottom 96 well plate containing a blood stained cloth disk in the following order: 1.25% detergent in H$_2$O 20 µL; 200 boric acid 20 µL; 120FH 6 µL; H$_2$O 134 µL; and 2.5% formulation in H$_2$O 20 µL. The assay total volume was 200 µµL. The 96 well plate was covered with foil and incubated for 1 hour shaking at 200 RPM at 37° C. The foil was removed and 100 µL of the supernatant was pipetted before removing all liquid.

Rinse: the plate with stained disks was refilled with 200 µl dH$_2$O per well, and sealed with foil. Wash was performed with a Multitron shaker set to 900 rpm. The sealed plate was placed on the platform and the door was closed, allowing the shaker to spin up until it reached 890 rpm (about 60 seconds) before removing the plate. The rinse water was removed and discarded. A total of three washes were performed.

White Light Reflectance Reading.

The test fabric circles had a diameter of 5.56 mm (area 24.25 mm square). Of this the inner circle used for measuring white light reflectance had a diameter of about 4.16 mm corresponding to 40 pixels (area 13.64 mm square, corresponding to 1264 pixels). While light reflectance was quantified via a 16 bit/pixel grayscale image corresponding to the measurement area. The imager was pre-normalized for any source light variation over the imager pixels.

Figure 15:
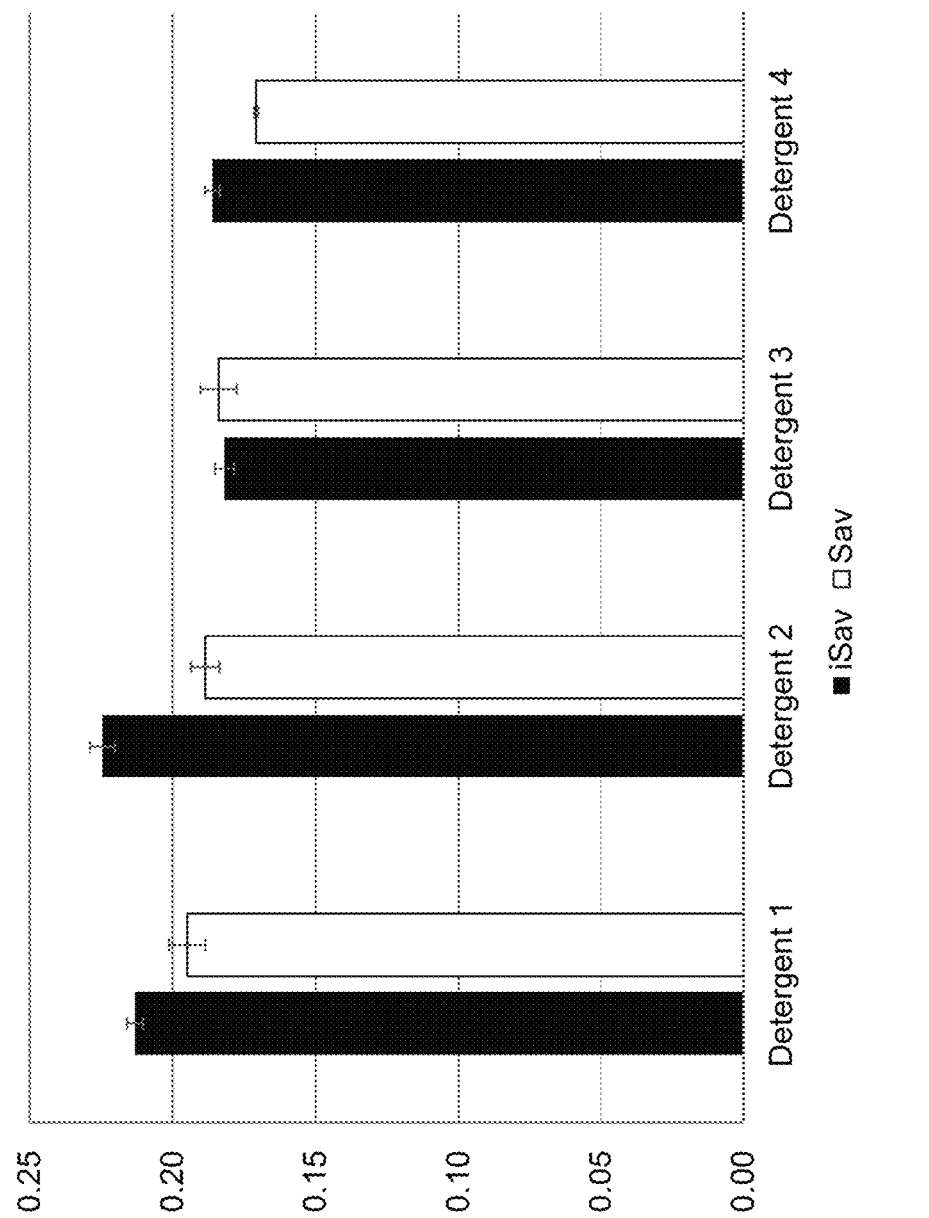
FIG. 15 illustrates that stain removal efficacy of detergent formulated iProtease (iSavinase; iSav; NI (SEQ ID NO: 1) and IC (SEQ ID NO: 2)) is comparable with Savinase (Sav; SEQ ID NO: 6) in four liquid laundry detergents.

FIG. 15 illustrates stain removal efficacy of detergent formulated iProtease is comparable with Savinase in four laundry detergents. This figure shows white light reflectance of washed EMPA 117 (blood/milk/ink stained) fabrics. Each graph is the average of the reflectance of three washed fabric. iProtease stain removal was comparable with Savinase in each of the detergent tested.

Example 15. Stability of Dilution Inducible iProtease Activity in Three Detergents Under Accelerated Ageing Conditions Detergents were: Detergent-1, Detergent-2 and Detergent-3. For benchmarking 1% (v/v) Savinase was used, but instead of formulating the inhibitor stabilized form, the inhibitor was first removed by three steps of overnight dialysis of 0.5 mL Savinase against 5 L mTSB buffer at 4° C. using a Tube-O-Dialyzer Medi (4000 Da; GBiosciences). Volume of dialyzed Savinase in mTSB were adjusted to 1.5 mL, and 3 µL dialyzed aliquot treated with equal volume of 4M KCL was used to formulate 100 µL detergent to get 1% (v/v) of the Savinase. Sample handling was essentially the same as in Example 8, except that formulations were made to 65% detergents supplemented with KCL to 1M final conc.

Purified NI and IC were used at equimolar conc. to 1% (v/v) dialyzed Savinase, at 38.1 µmolar concentration each. (NI+IC) premix in 2M KCl was prepared as described in Example 7, and formulations were made to 65% detergents supplemented with KCl to 1M final conc.

Figure 16:
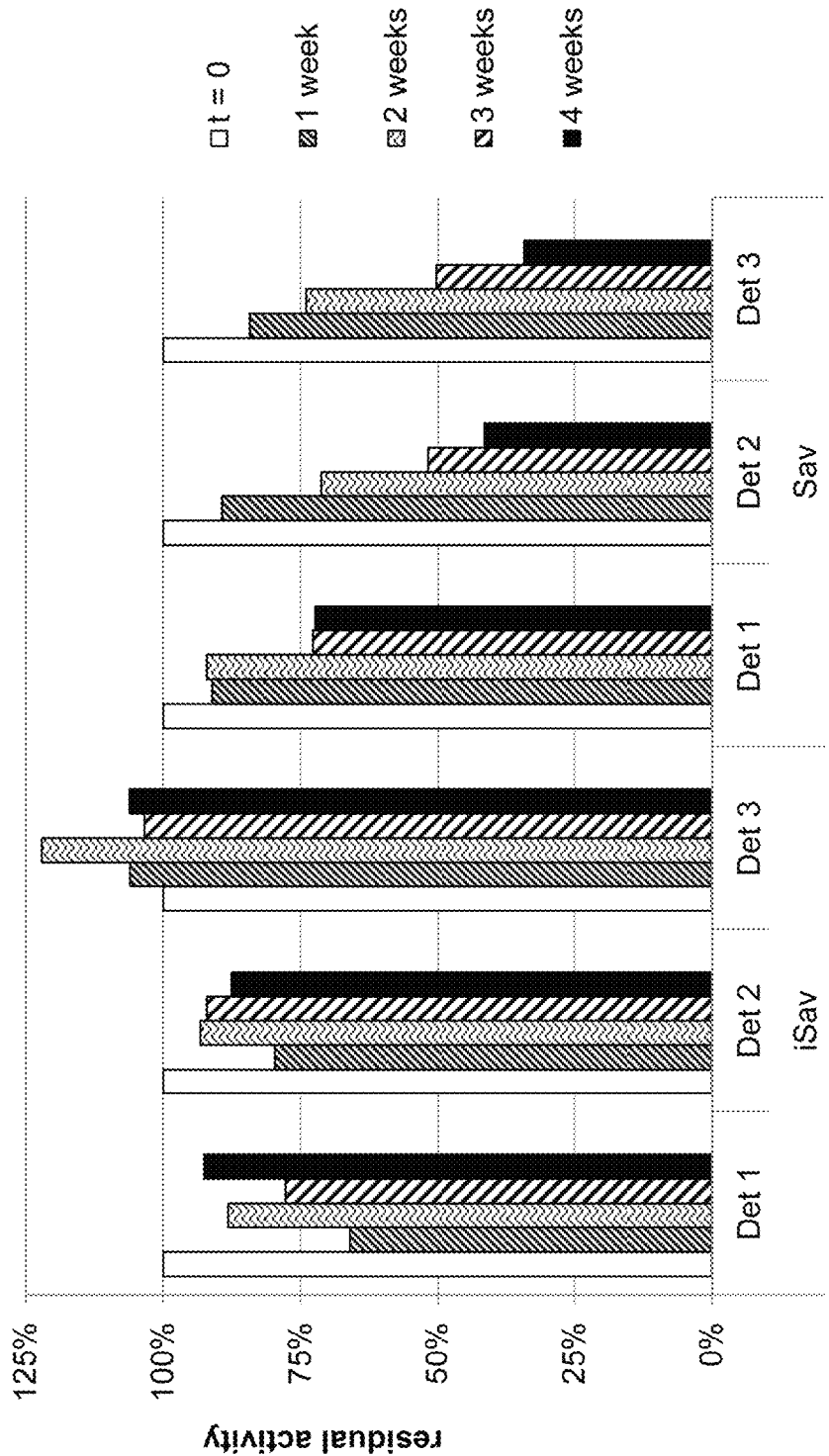
FIG. 16 illustrates stability of dilution inducible iProtease (iSavinase; iSav; NI (SEQ ID NO: 1) and IC (SEQ ID NO: 2)) activity in three liquid laundry detergents under accelerated ageing conditions compared to free Savinase (Sav; SEQ ID NO: 6).

Detergent formulations were stored under accelerated ageing conditions at 37° C. Residual protease activities were assayed at five time points, at t=0, 1, 2, 3, and 4 weeks, in serial dilutions to assay buffer as described before. The 2 min reads of 1:2560-fold dilutions of each formulation was normalized to the t=0 as 100% and graphed. FIG. 16 illustrates stability of dilution inducible iProtease activity in three detergents under accelerated ageing conditions. Data show that iProtease retained more activity than the inhibitor-stabilizer free Savinase, under accelerated ageing conditions at equal dosing of the proteases in each of the three detergents tested.

Example 16. Stability of Stain Removal Activity in Three Detergents Under Accelerated Ageing Conditions Formulations made for Example 15 were stored under accelerated ageing conditions at 37° C., and were evaluated for stain removal activity at five time points, at t=0, 1, 2, 3, and 4 weeks in storage.

Figure 17:
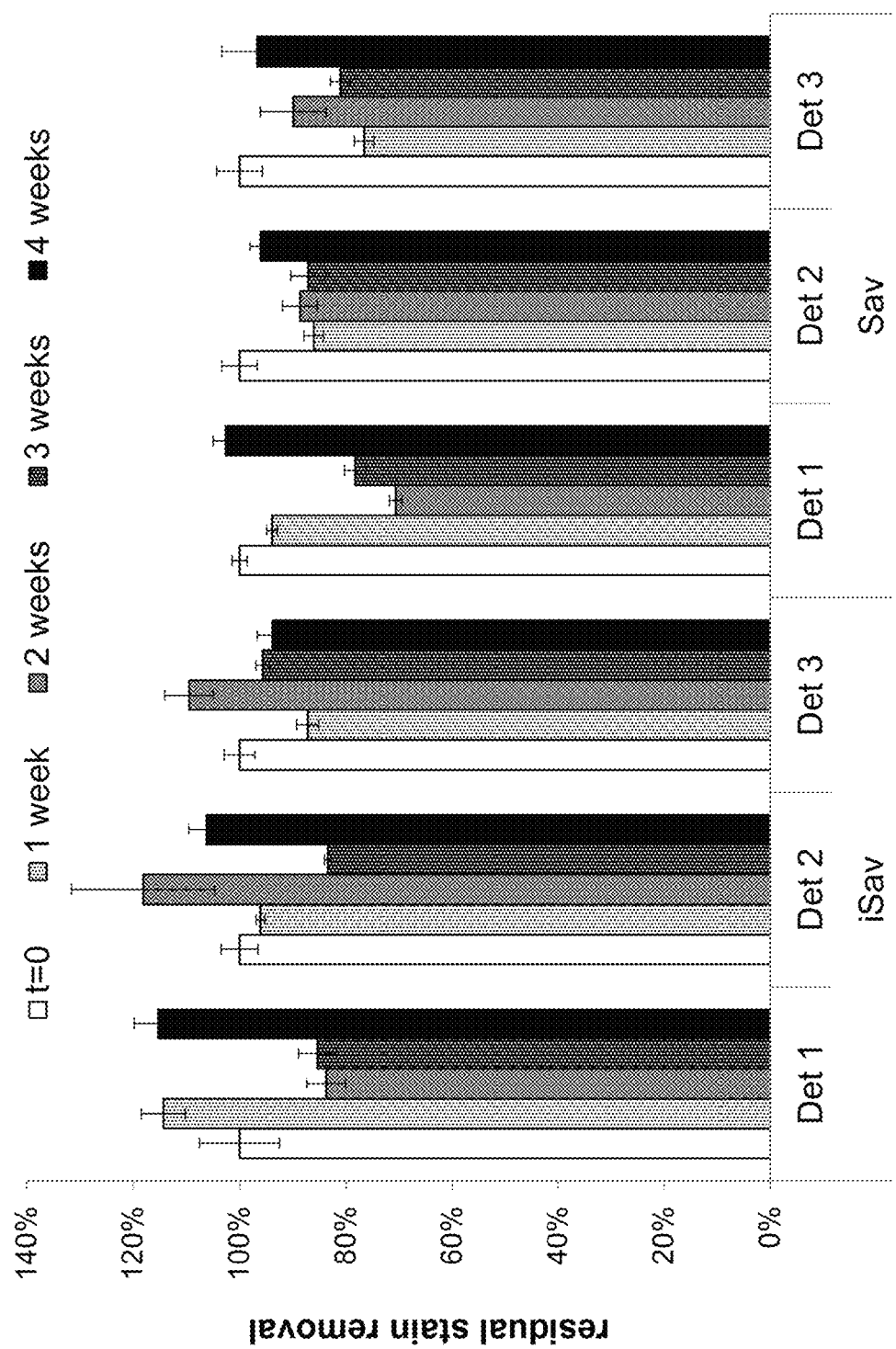
FIG. 17 illustrates stain removal stability under accelerated aging conditions in three liquid laundry detergents using iSavinase (iSav; NI (SEQ ID NO: 1) and IC (SEQ ID NO: 2)) and free Savinase (Sav; SEQ ID NO: 6).

The blood/milk/ink stained fabric of EMPA 117 was used in wash tests as described in Example 15. FIG. 17 illustrates stain removal stability under accelerated ageing conditions in three detergents. Three replicate washes were performed from each formulation at each time point. Referring to this figure, white light reflectance of the washed EMPA117 fabrics were normalized to their corresponding t=0 samples and were graphed.

Referring to FIG. 16, iProtease retained full stain removal activity in each of the three detergents, consistent with the stability of dilution inducible activity. Savinase, which without the stabilizer has lost between ~25-70% of initial enzyme activity also showed full stain removal activity. Possibly, proteases were dosed higher than necessary to achieve maximum stain removal within the confines of this assay.

Example 17. Division of Thermophilic Cis-Inteins into Trans-Inteins

The thermophilic cis-inteins were artificially split into trans-splicing intein pairs. Amino acid sequences of artificially split intein pairs are listed below by name of the cis intein as in the New England Biolab Intein Database followed by the splicing domain specifier (—N or —C). Abbreviated identifier of split intein parts are in parenthesis.

1. Cbu_DnaB (12)N-intein (SEQ ID NO: 16) and Cbu_DnaB (12)C-intein (SEQ ID NO: 17)
2. Mja_GF-6P(44)N-intein (SEQ ID NO: 18) and Mja_GF-6P-C (44)C-intein (SEQ ID NO: 19)
3. Mja_Hyp-1-N (#46-N) (SEQ ID NO: 20) and Mja_Hyp-1-C (#46-C) (SEQ ID NO: 21)
4. Mja_IF2-N (#47-N) (SEQ ID NO: 22) and Mja_IF2-C (#47-C) (SEQ ID NO: 23)
5. Mja_Pol-1-N (#50-N) (SEQ ID NO: 24) and Mja_Pol-1-C (#50-C) (SEQ ID NO: 25)
6. Pab_CDCl21-1-N (#79-N) (SEQ ID NO: 26) and Pab_CDCl21-1-C (#79-C) (SEQ ID NO: 27)

7. Pab_IF2-N (#81-N) (SEQ ID NO: 28) and Pab_IF2-C (#81-C) (SEQ ID NO: 29)

8. Pab_VMA-N(#92-N) (SEQ ID NO: 30) and Pab_VMA-C(#92-C) (SEQ ID NO: 31)

9. Pho_IF2-N (#103-N) (SEQ ID NO: 32) and Pho_IF2-C (#103-C) (SEQ ID NO: 33)

10. Pho_VMA-N(#110-N) (SEQ ID NO: 34) and Pho_VMA-C(#110-C) (SEQ ID NO: 35)

11. Rma_DnaB-N (#116-N) (SEQ ID NO: 36) and Rma_DnaB-C (#116-C) (SEQ ID NO: 37)

12. Sru_DnaB-N(#123-N) (SEQ ID NO: 38) and Sru_DnaB-C(#123-C) (SEQ ID NO: 39)

13. Tag_Pol-1 Tsp-TY_Pol-1-N (#128-N) (SEQ ID NO: 40) and Tag_Pol-1Tsp-TY_Pol-1-C(#128-C) (SEQ ID NO: 41)

14. Ter_RIR1-4-N (#135-N)(SEQ ID NO: 42) and Ter_RIR1-4-C (#135-C) (SEQ ID NO: 43)

15. Tko_IF2-N (#143-N) (SEQ ID NO: 44) and Tko_IF2-C (#143-C) (SEQ ID NO: 45)

16. Tth-HB27_DnaE-2-N (#150-N) (SEQ ID NO: 46) and Tth-HB27_DnaE-2-C (#150-C) (SEQ ID NO: 46)

The trans-splicing inteins described herein were further tested using bi-cistronic expression cassettes for restoration of protease activity.

Figure 18:
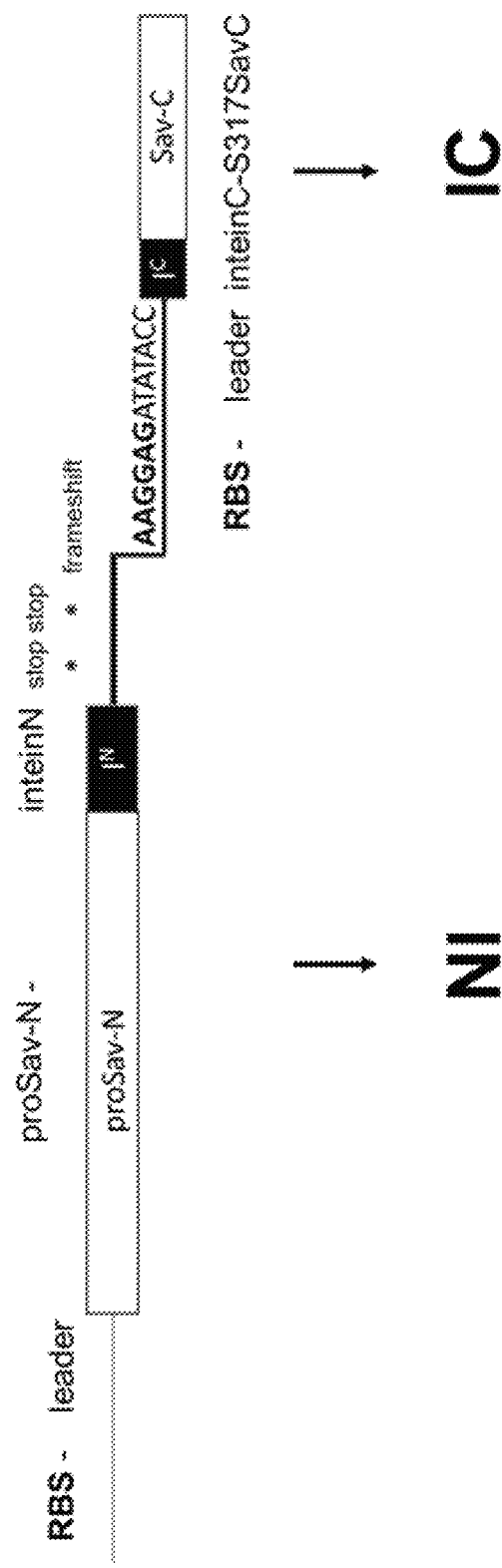
FIG. 18 illustrates a bi-cistronic expression cassette for expressing NI and IC and includes a nucleic acid sequence of the frameshifted RBS of SEQ ID NO: 48.

Example 18. Construction of Bi-Cistronic Expression Cassettes to Test Artificially Split Inteins in Savinase for Restoration of Protease Activity Savinase was split to two parts at the serine 317 aa residue (S317) to create proSav-N and Sav-C exteins. FIG. 18 illustrates a bi-cistronic expression cassette. Referring to FIG. 18, trans-splicing intein-N ($I^N$) was fused in frame with the C-termini of proSav-N creating NI, while trans-splicing intein-C ($I^C$) was fused in frame with the N-terminal serine (S317) residue of the C-extein (Sav-C) creating IC. NI and IC were assembled to a bi-cistronic expression cassette that encoded NI terminated by two stop codons followed by a frameshifted ribosome binding site (SEQ ID NO: 48) and leader sequence for the expression of IC. The assembled NI and IC were then cloned between the EcoRI and XhoI site of pBluescript and expressed in E. coli. This bi-cistronic construct express a single transcript with two separate translation products: NI and IC.

Example 19. Protease Activity from In Vitro Trans-Splicing Inteins

Figures 19A, 19B:
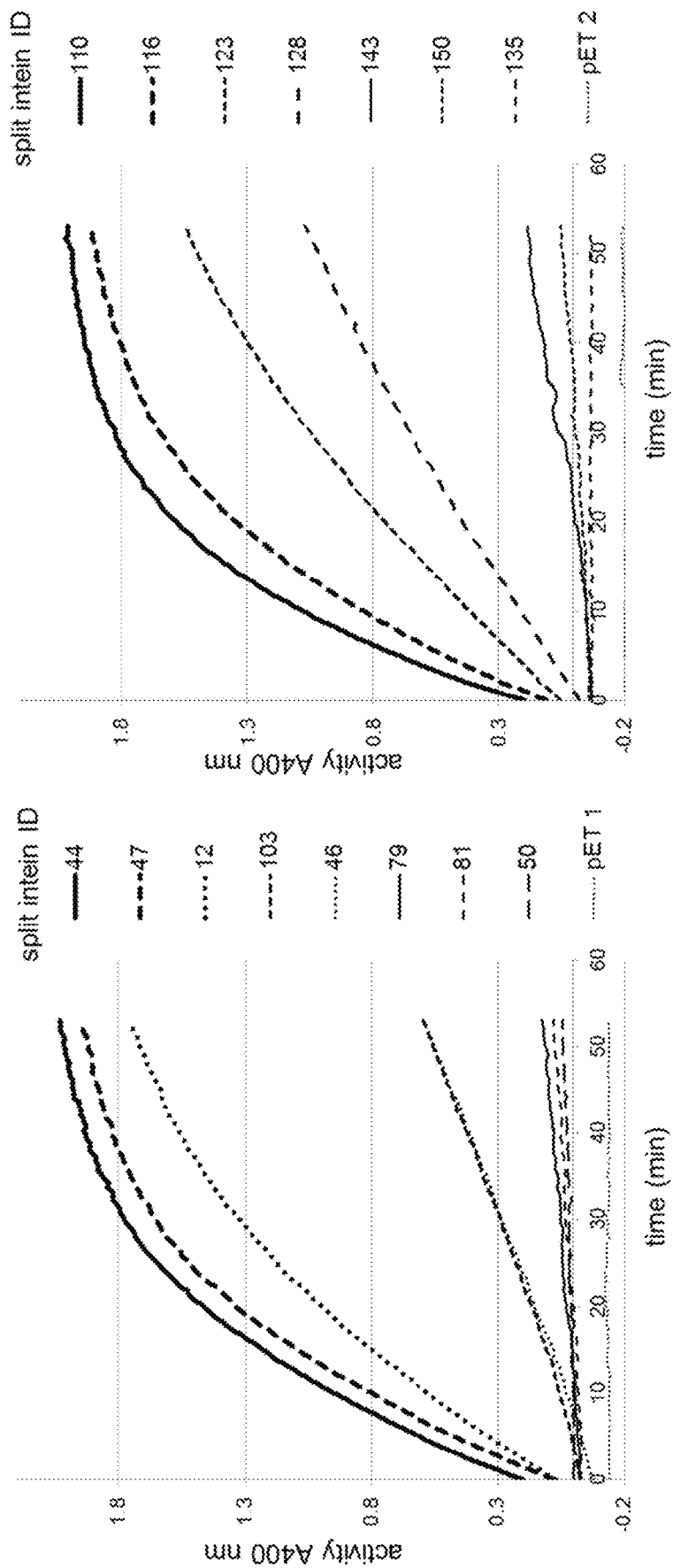
FIGS. 19A and 19B illustrate protease (iSavinase; NI (SEQ ID NO: 1) and IC (SEQ ID NO: 2)) activity from in vitro trans-splicing three hours after IPTG induction.

Bi-cistronic constructs of various trans splicing intein modified split Savinase were made as described above. Induction cultures, preparation of cell lysates and protease assays were performed as described before. Using the tester intein gp41-1, it was previously demonstrated that split Savinase NI and IC alone had no protease activity and that mixing of splicing disabled NI and IC did not restore protease activity. Protease activity requires trans-splicing mediated joining of inactive protease parts NI and IC and restoration of intact protease sequences (NC). FIGS. 19A and 19B illustrate protease activity from in vitro trans-splicing three hours after IPTG induction. FIG. 19 A illustrates protease activity following splicing of inteins 12, 12, 44, 46, 47, 50, 79, 81 and 103. FIG. 19B illustrates protease activity following splicing of inteins 110, 116, 123, 128, 135, 143, and 150. Variation in protease activity between constructs reflects sequence context specific differences in intein splicing.

REFERENCES

Aranko A S., Oeemig J S., Iwai H. (2013) Structural basis for protein trans-splicing by a bacterial intein-like domain protein ligation without nucleophilic side chains. FEBS J., 280(14):3256-69.

Besteman K., Zevenbergen M., Heering H. and Lemay S. (2004) Direct Observation of Charge Inversion by Multivalent Ions as a Universal Electrostatic Phenomenon. Phys. Rev. Lett. 93, 170802.

Evans T C., Martin D., Kolly R., Panne D., Sun L., Ghosh I., Chen L., Liu X.-Q. and XU M-Q. (2000) Protein trans-Splicing and Cyclization by a Naturally Split Intein from the dnaE Gene of Synechocystis Species PCC6803. J. Biol. Chem. 275, 9091-9094.

Lyklema J. (2009) Quest for ion-ion correlations in electric double layers and overcharging phenomena. Adv. Colloid Interface Sci. 147, 205-213.

Martin-Molina A., Quesada-Pérez M., Galisteo-González F. (2003) Looking into overcharging in model colloids through electrophoresis: asymmetric electrolytes. J. Chem. Phys. 118, 4183-89.

Martin D D., XU M-Q. and Evans T C. (2001) Characterization of a Naturally Occurring Trans-Splicing Intein from Synechocystis sp. PCC6803. Biochemistry, 40, 1393-1402.

Mootz H D., Blum E S., Tyszkiewicz A B. and Muir T W. (2003) Conditional protein splicing: a new tool to control protein structure and function in vitro and in vivo. J. Am. Chem. Soc. 125, 10561-9.

Nichols N M, Benner J S, Martin D D and Evans T C Jr (2003) Zinc ion effects on individual Ssp DnaE splicing steps: regulating pathway progression. Biochemistry, 42 (18), 5301-11.

Perler F B. (2005) Protein Splicing Mechanisms and Applications. IUBMB Life, 57(7), 469-476.

Selgrade D F., Lohmueller J J., Lienert F. and Silver P. (2013) Protein scaffold-activated protein trans-splicing in mammalian cells. J. Am. Chem. Soc. 135, 7713-19.

Shah N H., Eryilmaz E., Cowburn D. and Muir T W. (2013) Naturally split inteins assemble through a "capture and collapse" mechanism. J. Am. Chem. Soc. 135, 18673-81.

Shi J. and Muir T W J. (2005) Development of a tandem protein trans-splicing system based on native and engineered split inteins. J. Am. Chem. Soc. 127, 6198-206.

Shi J. and Muir T. W. (2006) Development of a Tandem Protein Trans-Splicing System Based on Native and Engineered Split Inteins. J. Am. Chem. Soc., 2005, 127 (17), 6198-6206.

Sun P., Ye S., Ferrandon S., Evans T. C., Xu M-Q., and Rao Z. (2005) Crystal Structures of an Intein from the Split dnaE Gene of Synechocystis sp. PCC6803 Reveal the Catalytic Model Without the Penultimate Histidine and the Mechanism of Zinc Ion Inhibition of Protein Splicing. J. Mol. Biol. 353, 1093-1105.

Topilina N I. And Mills K V. (2014) Recent advances in in vivo applications of intein-mediated protein splicing. Mobile DNA, (5) 5.

Trulsson M., Jonsson B., Akesson T. and Forsman J. (2006) Repulsion between Oppositely Charged Surfaces in Multivalent Electrolytes. Phys. Rev. Lett. 97, 068302.

Wu H., Hu Z, and Liu X-Q. (1998) Protein trans-splicing by a split intein encoded in a split DnaE gene of Synechocystis sp. PCC6803. Proc. Natl. Acad. Sci USA, 95, 9226-31.

Zhang L., Xiao N. n Pan Y., Zheng Y., Pan Z., Luo Z., Xu X., Liu Y. (2010) Binding and inhibition of copper ions to RecA inteins from *Mycobacterium tuberculosis*. Chemistry, 16(14), 4297-306.

Zhang L, Zheng Y., Callahan B, Bedfort M., Liu Y. (2011) Cisplatin inhibits protein splicing, suggesting inteins as therapeutic targets in mycobacteria. J. Biol. Chem. 286 (2), 1277-82.

Zheng Y., W U Q., Xu M-Q. and Liu Y. (2012) Mutual synergistic protein folding in split intein. Biosci. Rep. 32, 433-442.

The references cited throughout this application are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A method of regulating protease activity comprising forming the home care product by adding an intein-modified protease that comprises a first precursor and a second precursor:
   the first precursor comprises an N-extein of a target protease fused to a solubility enhanced N-intein of a trans-splicing intein, and the carboxy terminus of the N-extein is fused to the amino terminus of the solubility enhanced N-intein,
   the solubility enhanced N-intein comprises an N-intein and a first solubility enhancer, and the carboxy terminus of the N-intein is fused to the first solubility enhancer by a first linker;
   the second precursor comprises a solubility enhanced C-intein of the trans-splicing intein fused to a C-extein of the target protease, and the carboxy terminus of the solubility enhanced C-intein is fused to the amino terminus of the C-extein,
   the solubility enhanced C-intein comprises a C-intein and a second solubility enhancer, and the second solubility enhancer is fused to the amino terminus of the C-intein by a second linker;
   each of the first solubility enhancer and the second solubility enhancer comprises the thioredoxin domain Trx, and the first precursor is separated from the second precursor prior to trans-splicing;
   wherein the intein-modified protease has enhanced solubility and reduced activity compared to the target protease, and the activity of the target protease is at least partially restored upon trans-splicing of the intein-modified protease and fusion of the N-extein and the C-extein, and
   wherein the first precursor consists of an amino acid sequence with at least 90% identity to SEQ ID NO: 1, and
   the second precursor consists of an amino acid sequence with at least 90% identity to SEQ ID NO: 2.

2. The method of claim 1, wherein the first linker or the second linker is a DPNG linker.

3. The method of claim 1, wherein the first precursor comprises, consists essentially of, or consists of an amino acid sequence with 100% identity to SEQ ID NO: 1, and the first precursor comprises, consists essentially of, or consists of an amino acid sequence with 100% identity to SEQ ID NO: 2.

4. The method of claim 1, wherein the home care product further comprises at least one agent selected from the group consisting of: detergent, soap, industrial cleaner, dish washing liquid, water softeners, surfactants, bleach, enzymes, brighteners, fragrances, anionic surfactants, nonionic surfactants, builders to remove the hardness ions, antiredeposition agents, dye transfer inhibitors, soil release polymers, optical brighteners, enzyme stabilizers, viscosity control compounds, pH control compounds, soap and silicones to control excessive foaming, preservatives for microbial control, perfume and dye for scent and appearance, bleaching agents, water, solubilizers, alkylbenzenesulphonates, ethoxylated fatty alcohols, sodium citrate, tetrasodium EDTA or an acrylic polymer, PVP K-30, Chromabond S-100, Chromabond S-400, Sorez 100, Repel-O-Tex SRP-6, Tinopal CBS-X, calcium chloride, sodium tetraborate, propylene glycol, sodium formate, sodium citrate, monoethanolamine, propylene glycol, sodium xylene sulfonate, polymers, and citric acid.

5. The method of claim 1, wherein the home care product further comprises a fuel additive selected from the group consisting of: a long-chain amine or amide, polyisobuteneamine, polyisobuteneamide and succinimide.

6. The method of claim 1, wherein forming comprises combining the home care product with one or more effectors wherein the one or more effectors is capable of suppressing trans-splicing.

7. The method of claim 6, wherein the one or more effectors are selected from the group consisting of: sodium salt supplements, potassium salt supplements, ammonium salt supplements, charged polymeric salt supplements, polyol supplements, sodium chloride, tetrasodium iminodisuccinate, disodium succinate, disodium tartrate, potassium lactate, potassium citrate, potassium chloride, sodium nicotinate, ammonium sulfate, ammonium nitrate, lithium citrate, sodium polyaspartate, sodium polyacrylate, tetraethylene glycol, polyethylene glycol, tetraglycol, propylene carbonate, mono propylene glycol, glycerol, and tomadol.

8. The method of claim 7, wherein the one or more effectors includes potassium chloride.

9. The method of claim 8, wherein the potassium chloride concentration is in a range from 0.1 M to 5.0 M.

10. The method of claim 9, wherein the potassium chloride concentration is in a range from 0.5 M to 2.0 M.

11. The method of claim 6, wherein the one or more effectors is capable of suppressing trans-splicing.

12. The method of claim 11, wherein the suppressing is reversible.

13. The method of claim 1 further comprising causing splicing of the intein-modified protease.

14. The method of claim 13, wherein the step of causing splicing includes diluting the mixture with a liquid to a mixture:liquid ratio of less or equal to one selected from the group consisting of: 1:5, 1:10, 1:20, 1:50: 1:60, 1:70, 1:80, 1:90, 1:100, 1:150, 1:200, 1:250, 1:300, 1:350, and 1:400 of a mixture to liquid.

15. The method of claim 14, wherein the liquid is one of water and an aqueous buffer.

* * * * *